US012631644B2

(12) United States Patent
Tunac

(10) Patent No.: US 12,631,644 B2
(45) Date of Patent: May 19, 2026

(54) BIOMARKER PANEL TARGETED TO DISEASES DUE TO MULTIFACTORIAL ONTOLOGY OF GLYCOCALYX DISRUPTION

(71) Applicant: Arterez, Inc., West Bloomfield, MI (US)

(72) Inventor: Josefino B. Tunac, Oxford, MI (US)

(73) Assignee: ARTEREZ, INC., West Bloomfield, MI (US)

( * ) Notice: Subject to any disclaimer, the term of this patent is extended or adjusted under 35 U.S.C. 154(b) by 1047 days.

(21) Appl. No.: 17/762,703

(22) PCT Filed: Sep. 25, 2020

(86) PCT No.: PCT/US2020/052912
§ 371 (c)(1),
(2) Date: Mar. 22, 2022

(87) PCT Pub. No.: WO2021/062298
PCT Pub. Date: Apr. 1, 2021

(65) Prior Publication Data

US 2022/0390454 A1 Dec. 8, 2022

Related U.S. Application Data

(60) Provisional application No. 62/907,389, filed on Sep. 27, 2019.

(51) Int. Cl.
*G01N 33/575* (2026.01)
*A61K 31/381* (2006.01)
*A61K 31/4045* (2006.01)
*A61K 31/4985* (2006.01)
*A61K 45/06* (2006.01)
*A61P 9/10* (2006.01)

(52) U.S. Cl.
CPC ....... *G01N 33/5758* (2026.01); *A61K 31/381* (2013.01); *A61K 31/4045* (2013.01); *A61K 31/4985* (2013.01); *A61K 45/06* (2013.01); *A61P 9/10* (2018.01)

(58) Field of Classification Search
CPC ................................................ G01N 33/57484
USPC ........................................................ 434/7.23
See application file for complete search history.

(56) References Cited

U.S. PATENT DOCUMENTS

| | | | |
|---|---|---|---|
| 5,281,700 | A | 1/1994 | Schnitzer et al. |
| 5,453,359 | A | 9/1995 | Gargan et al. |
| 5,811,250 | A | 9/1998 | Solum et al. |
| 5,843,690 | A | 12/1998 | Gargan |
| 5,922,302 | A | 7/1999 | Goldenberg et al. |
| 6,156,530 | A | 12/2000 | Rånby |
| 8,759,095 | B2 | 6/2014 | Vink et al. |
| 9,086,412 | B2 | 7/2015 | Taylor et al. |
| 10,449,209 | B2 * | 10/2019 | Tunac ................ A61K 31/7052 |
| 11,143,659 | B2 | 10/2021 | Tunac |
| 11,707,475 | B2 * | 7/2023 | Tunac ................ A61K 31/4045 514/249 |
| 11,821,905 | B2 * | 11/2023 | Tunac .................... G01N 33/86 |
| 2001/0051351 | A1 | 12/2001 | Racis |
| 2002/0086282 | A1 | 7/2002 | Pillarisetti et al. |
| 2002/0106634 | A1 | 8/2002 | Adams et al. |
| 2002/0132370 | A1 | 9/2002 | Lassen et al. |
| 2002/0182587 | A1 | 12/2002 | Pillarisetti |
| 2003/0003515 | A1 | 1/2003 | Farrell et al. |
| 2003/0008911 | A1 | 1/2003 | Evans et al. |
| 2003/0036103 | A1 | 2/2003 | Pillarisetti et al. |
| 2003/0040505 | A1 | 2/2003 | Fogelman et al. |
| 2003/0124536 | A1 | 7/2003 | McCarthy |
| 2003/0166004 | A1 | 9/2003 | Gyuris et al. |
| 2003/0199000 | A1 | 10/2003 | Valkirs et al. |
| 2003/0219813 | A1 | 11/2003 | Yang et al. |
| 2004/0002124 | A1 | 1/2004 | Lau et al. |
| 2004/0038856 | A1 | 2/2004 | Chakravarty et al. |
| 2004/0047861 | A1 | 3/2004 | Kehrel et al. |
| 2004/0121343 | A1 | 6/2004 | Buechler et al. |
| 2004/0142334 | A1 | 7/2004 | Schacht |
| 2004/0142496 | A1 | 7/2004 | Nicholson et al. |
| 2004/0203083 | A1 | 10/2004 | Buechler et al. |
| 2004/0213789 | A1 | 10/2004 | Yacoby-Zeevi et al. |
| 2004/0215087 | A1 | 10/2004 | Genero et al. |
| 2004/0253637 | A1 | 12/2004 | Buechler et al. |
| 2005/0032140 | A1 | 2/2005 | Kurosawa et al. |
| 2005/0065184 | A1 | 3/2005 | Wolf |
| 2005/0069969 | A1 | 3/2005 | Berg et al. |
| 2005/0089914 | A1 | 4/2005 | Yamasaki |
| 2005/0107601 | A1 | 5/2005 | Loeb |
| 2005/0181386 | A1 | 8/2005 | Diamond et al. |
| 2005/0250156 | A1 | 11/2005 | Shebuski et al. |
| 2006/0003338 | A1 | 1/2006 | Deng et al. |
| 2006/0039863 | A1 | 2/2006 | Schirner et al. |
| 2006/0105323 | A1 | 5/2006 | Whitelaw et al. |
| 2006/0269552 | A1 | 11/2006 | Yacoby-Zeevi et al. |
| 2006/0275214 | A1 | 12/2006 | Gregor et al. |
| 2006/0286681 | A1 | 12/2006 | Lehmann et al. |
| 2007/0065879 | A1 | 3/2007 | Conover et al. |
| 2007/0134814 | A1 | 6/2007 | Kajander et al. |
| 2007/0141055 | A1 | 6/2007 | Kajander et al. |

(Continued)

FOREIGN PATENT DOCUMENTS

| | | | |
|---|---|---|---|
| CN | 1352029 | A | 6/2002 |
| CN | 102353789 | A | 2/2012 |

(Continued)

OTHER PUBLICATIONS

Tockman et al (Cancer Res., 1992, 52:2711s-2718s).*

(Continued)

*Primary Examiner* — Sean E Aeder
(74) *Attorney, Agent, or Firm* — Weaver Austin Villeneuve & Sampson LLP

(57) ABSTRACT

The present disclosure provides biomarkers useful as companion diagnostics for detecting glycocalyx-based disease that is amenable to treatment using compounds designed for improving the condition of the glycocalyx and/or reducing inflammation and/or oxidative damage, as well as related compositions, kits, and methods.

21 Claims, 14 Drawing Sheets

(56) References Cited

U.S. PATENT DOCUMENTS

2007/0141632 A1 6/2007 Xu et al.
2007/0196926 A1 8/2007 Soito et al.
2007/0213255 A1 9/2007 Hastings et al.
2007/0225222 A1 9/2007 Chiquet-Ehrismann et al.
2007/0225261 A1 9/2007 Miller et al.
2007/0239483 A1 10/2007 Chandler et al.
2007/0269836 A1 11/2007 McPherson et al.
2008/0009684 A1 1/2008 Corsetti et al.
2008/0010024 A1 1/2008 Diamond
2008/0057516 A1 3/2008 Saarma et al.
2008/0057590 A1* 3/2008 Urdea ................ G01N 33/6845 436/71
2008/0121025 A1 5/2008 Okazaki
2008/0124277 A1 5/2008 Arap et al.
2008/0160007 A1 7/2008 Powell
2008/0300797 A1 12/2008 Tabibiazar et al.
2008/0300798 A1 12/2008 McDevitt et al.
2008/0311606 A1 12/2008 Chapman-Montgomery et al.
2009/0011055 A1 1/2009 Lawrence et al.
2009/0054256 A1 2/2009 Dogulu et al.
2009/0104121 A1 4/2009 Madasamy
2009/0155827 A1 6/2009 Zeiher et al.
2009/0197344 A1 8/2009 Villard-Saussine et al.
2009/0215042 A1 8/2009 Sella-Tavor et al.
2009/0246810 A1 10/2009 Maier et al.
2009/0263827 A1 10/2009 Johansen
2010/0028335 A1 2/2010 Lu et al.
2010/0068705 A1 3/2010 Helgadottir et al.
2010/0105046 A1 4/2010 Epstein et al.
2010/0112587 A1 5/2010 Hare et al.
2010/0130403 A1 5/2010 Pfuetzner et al.
2010/0158896 A1 6/2010 Brown et al.
2010/0159474 A1 6/2010 Bergmann et al.
2010/0209350 A1 8/2010 Pfuetzner et al.
2010/0233085 A1 9/2010 Kwon et al.
2010/0248288 A1 9/2010 Hess et al.
2010/0249064 A1 9/2010 Singleton et al.
2010/0261284 A1 10/2010 Spanuth
2010/0267025 A1 10/2010 Young
2010/0267062 A1 10/2010 Frey et al.
2010/0286053 A1 11/2010 Kuan et al.
2010/0291614 A1 11/2010 Nitz et al.
2010/0304424 A1 12/2010 Vink et al.
2010/0310646 A1 12/2010 Oxvig et al.
2011/0003297 A1 1/2011 Liew
2011/0008346 A1 1/2011 Duckers
2011/0070601 A1 3/2011 Kastrup
2011/0076692 A1 3/2011 Sista et al.
2011/0083199 A1 4/2011 Essers et al.
2011/0104735 A1 5/2011 Buehrer et al.
2011/0107821 A1 5/2011 Hess et al.
2011/0111527 A1 5/2011 Hess et al.
2011/0117589 A1 5/2011 Bergmann et al.
2011/0136157 A1 6/2011 Cooper
2011/0137131 A1 6/2011 Adourian et al.
2011/0177610 A1 7/2011 Matsuo et al.
2011/0229911 A1 9/2011 Bergmann et al.
2011/0262444 A1 10/2011 Kim
2011/0274749 A1 11/2011 Gaillard et al.
2012/0003751 A1 1/2012 Bergmann et al.
2012/0028880 A1 2/2012 Pasqualini et al.
2012/0149131 A1 6/2012 Struck et al.
2012/0164669 A1 6/2012 Hess et al.
2012/0208715 A1 8/2012 McDevitt et al.
2012/0208762 A1 8/2012 Dudley
2012/0219943 A1 8/2012 Ky et al.
2012/0231472 A1 9/2012 Anderberg et al.
2012/0264636 A1 10/2012 Holm et al.
2013/0004487 A1 1/2013 Zeiher et al.
2013/0052637 A1 2/2013 Kovar et al.
2013/0137632 A1 5/2013 Pfuetzner et al.
2013/0164284 A1 6/2013 Lu et al.
2013/0171649 A1 7/2013 Mayr
2013/0190197 A1 7/2013 Liew
2013/0210041 A1 8/2013 Anderberg et al.
2013/0261177 A1 10/2013 Johansson et al.
2013/0273096 A1 10/2013 Daniels
2013/0302841 A1 11/2013 Struck et al.
2014/0024551 A1 1/2014 Mayr
2014/0044797 A1 2/2014 Johansson et al.
2014/0065648 A1 3/2014 Wienhues-Thelen et al.
2014/0100128 A1 4/2014 Narain et al.
2014/0141986 A1 5/2014 Spetzler et al.
2014/0147867 A1 5/2014 Arnold et al.
2014/0206698 A1 7/2014 Dudley
2014/0271464 A1 9/2014 Garcia-Martinez et al.
2014/0315752 A1 10/2014 Anderberg et al.
2014/0324460 A1 10/2014 Caffrey et al.
2014/0357505 A1 12/2014 Mohler, III et al.
2015/0010929 A1 1/2015 Anderberg et al.
2015/0057325 A1 2/2015 Johansson et al.
2015/0064139 A1 3/2015 Shoemaker et al.
2015/0079615 A1 3/2015 Wienhues-Thelen et al.
2015/0087727 A1 3/2015 Bergmann et al.
2015/0099311 A1 4/2015 Holmes et al.
2015/0160229 A1 6/2015 Schaal et al.
2015/0175979 A1 6/2015 Bottini et al.
2015/0268251 A1 9/2015 Zaugg et al.
2015/0308939 A1 10/2015 Oberleithner
2015/0346217 A1 12/2015 Spanuth
2015/0376704 A1 12/2015 Harrington et al.
2016/0084849 A1 3/2016 Chojkier et al.
2016/0109464 A1 4/2016 Horsch et al.
2016/0121023 A1 5/2016 Edelman et al.
2016/0169911 A1 6/2016 Block et al.
2016/0252526 A1 9/2016 Bergmann et al.
2016/0282362 A1 9/2016 Karsdal et al.
2016/0320411 A1 11/2016 Struck et al.
2016/0320416 A1 11/2016 Pugia et al.
2016/0327548 A1 11/2016 Crawford et al.
2017/0010280 A1 1/2017 Tanaka et al.
2017/0010283 A1 1/2017 Karl et al.
2017/0138961 A1 5/2017 Hess et al.
2017/0218091 A1 8/2017 Ambrosi
2017/0227552 A1 8/2017 Latini et al.
2017/0234853 A1 8/2017 Contant et al.
2017/0269106 A1 9/2017 Everett et al.
2017/0304389 A1 10/2017 Mann
2018/0000972 A1 1/2018 Lee
2018/0003685 A1 1/2018 Cummings et al.
2018/0003725 A1 1/2018 Kline
2018/0031483 A1 2/2018 Singamaneni et al.
2018/0036285 A1 2/2018 Tunac et al.
2018/0088131 A1 3/2018 Ostrowski et al.
2018/0100862 A1 4/2018 Goix et al.
2018/0291374 A1 10/2018 Bloch et al.
2018/0292414 A1 10/2018 Amir et al.
2018/0298341 A1 10/2018 Elliman
2018/0364257 A1 12/2018 Tunac
2019/0010223 A1 1/2019 Smith
2019/0112582 A1 4/2019 Redondo Moya et al.
2019/0224135 A1 7/2019 Struck et al.
2019/0227074 A1 7/2019 Denk et al.
2019/0227081 A1 7/2019 Struck et al.
2019/0250126 A1 8/2019 Hall et al.
2019/0369114 A1 12/2019 Van Eyk et al.
2020/0003759 A1 1/2020 Vath et al.
2020/0018747 A1 1/2020 King et al.
2020/0041496 A1 2/2020 Kershner et al.
2020/0049721 A1 2/2020 Bergmann
2020/0166523 A1 5/2020 Gill et al.
2020/0199510 A1 6/2020 Luo et al.
2020/0241019 A1 7/2020 Kim
2020/0271670 A1 8/2020 Block et al.
2022/0057410 A1 2/2022 Tunac
2022/0288110 A1 9/2022 Tunac

FOREIGN PATENT DOCUMENTS

CN 102863530 A 1/2013
CN 104914247 A 9/2015
CN 109055368 A 12/2018
DE 20220351 U1 8/2003
DE 10247356 A1 4/2004

(56) References Cited

FOREIGN PATENT DOCUMENTS

| | | | |
|---|---|---|---|
| DE | 10316059 | A1 | 11/2004 |
| EP | 2439535 | A1 | 4/2012 |
| EP | 2597467 | A1 | 5/2013 |
| JP | 2003227837 | A | 8/2003 |
| JP | 2006030183 | A | 2/2006 |
| JP | 2008188016 | A | 8/2008 |
| JP | 2010515023 | A | 5/2010 |
| JP | 2011038858 | A | 2/2011 |
| JP | 2014505259 | A | 2/2014 |
| JP | 2015047141 | A | 3/2015 |
| JP | 2018021797 | A | 2/2018 |
| JP | 2019158753 | A | 9/2019 |
| KR | 20060105654 | A | 10/2006 |
| KR | 20090048056 | A | 5/2009 |
| KR | 20180055319 | A | 5/2018 |
| RU | 2154977 | C1 | 8/2000 |
| RU | 2158532 | C1 | 11/2000 |
| RU | 2248744 | C1 | 3/2005 |
| RU | 2533836 | C1 | 11/2014 |
| RU | 2550722 | C1 | 5/2015 |
| RU | 2557916 | C1 | 7/2015 |
| RU | 2592237 | C1 | 7/2016 |
| RU | 2617418 | C1 | 4/2017 |
| RU | 2720672 | C1 | 5/2020 |
| UA | 57001 | U | 2/2011 |
| UA | 60581 | U | 6/2011 |
| UA | 92604 | U | 8/2014 |
| WO | WO-9310261 | A1 | 5/1993 |
| WO | WO-9810293 | A1 | 3/1998 |
| WO | WO-9826092 | A1 | 6/1998 |
| WO | WO-9826292 | A1 | 6/1998 |
| WO | WO-9918442 | A1 | 4/1999 |
| WO | WO-9948916 | A2 | 9/1999 |
| WO | WO-9964627 | A2 | 12/1999 |
| WO | WO-0050639 | A2 | 8/2000 |
| WO | WO-0111064 | A2 | 2/2001 |
| WO | WO-0123426 | A2 | 4/2001 |
| WO | WO-0173445 | A2 | 10/2001 |
| WO | WO-0202593 | A2 | 1/2002 |
| WO | WO-2004001421 | A2 | 12/2003 |
| WO | WO-2006052924 | A2 | 5/2006 |
| WO | WO-2006115047 | A1 | 11/2006 |
| WO | WO-2007070021 | A1 | 6/2007 |
| WO | WO-2008009869 | A1 | 1/2008 |
| WO | WO-2008040328 | A2 | 4/2008 |
| WO | WO-2009033095 | A2 | 3/2009 |
| WO | WO-2009058168 | A1 | 5/2009 |
| WO | WO-2009100907 | A1 | 8/2009 |
| WO | WO-2009128917 | A2 | 10/2009 |
| WO | WO-2010018203 | A1 | 2/2010 |
| WO | WO-2010026272 | A1 | 3/2010 |
| WO | WO-2010047767 | A2 | 4/2010 |
| WO | WO-2010054810 | A1 | 5/2010 |
| WO | WO-2010133173 | A1 | 11/2010 |
| WO | WO-2011115783 | A1 | 9/2011 |
| WO | WO-2012009547 | A2 | 1/2012 |
| WO | WO-2012020045 | A1 | 2/2012 |
| WO | WO-2012066140 | A1 | 5/2012 |
| WO | WO-2013045570 | A1 | 4/2013 |
| WO | WO-2013188787 | A1 | 12/2013 |
| WO | WO 2014/135488 | A1 * | 9/2014 |
| WO | WO-2015073709 | A2 | 5/2015 |
| WO | WO-2015110957 | A2 | 7/2015 |
| WO | WO-2016123163 | A2 | 8/2016 |
| WO | WO-2016126662 | A1 | 8/2016 |
| WO | WO-2016130802 | A1 | 8/2016 |
| WO | WO-2016164534 | A1 | 10/2016 |
| WO | WO-2016176089 | A1 | 11/2016 |
| WO | WO-2017136652 | A1 | 8/2017 |
| WO | WO-2018042072 | A1 | 3/2018 |
| WO | WO-2018136825 | A1 | 7/2018 |
| WO | WO 2018/164940 | A1 * | 9/2018 |
| WO | WO-2018178386 | A1 | 10/2018 |
| WO | WO-2018208846 | A1 | 11/2018 |
| WO | WO-2019183671 | A1 | 10/2019 |
| WO | WO-2020018005 | A1 | 1/2020 |
| WO | WO-2020053355 | A2 | 3/2020 |
| WO | WO-2020074777 | A1 | 4/2020 |
| WO | WO-2020081866 | A1 | 4/2020 |
| WO | WO-2020115288 | A1 | 6/2020 |
| WO | WO-2020146263 | A1 | 7/2020 |
| WO | WO-2020148769 | A1 | 7/2020 |
| WO | WO-2020167735 | A1 | 8/2020 |
| WO | WO-2021062298 | A1 | 4/2021 |

OTHER PUBLICATIONS

Alexander et al. (2011) "Association between y' fibrinogen levels and inflammation" Thromb Haemost 105:605-9 [NIH Public Access—Author Manuscript—10 pages].

Allender et al. (2008) "Patterns of coronary heart disease mortality over the 20th century in England and Wales: Possible plateaus in the rate of decline" BMC Public Health 8:148 (12 pages).

Appiah et al. (2015) "Association of Plasma y' Fibrinogen With Incident Cardiovascular Disease The Atherosclerosis Risk in Communities (ARIC) Study" Arterioscler Thromb Vasc Biol. 35(12):2700-2706.

Canadian Office Action dated Jan. 6, 2022 issued in CA 3,012,985 [P001CA].

Cosin-Sales et al. (2004) "Pregnancy-Associated Plasma Protein A and Its Endogenous Inhibitor, the Proform of Eosinophil Major Basic Protein (proMBP), Are Related to Complex Stenosis Morphology in Patients With Stable Angina Pectoris" Circulation 109(14):1724-1728.

Danesh et al. (2005) "Plasma Fibrinogen Level and the Risk of Major Cardiovascular Diseases and Nonvascular Mortality An Individual Participant Meta-analysis" JAMA 294(14):1799-1809.

International Preliminary Report on Patentability dated Apr. 7, 2022, in Application No. PCT/US2020/052912.

Kalousová et al. (2014) "Pregnancy-associated plasma protein A associates with cardiovascular events in diabetic hemodialysis patients." Atherosclerosis 236(2):263-269.

Lindahl, Bertil (2013) "The Story of Growth Differentiation Factor 15: Another Piece of the Puzzle" Clinical Chemistry 59(11):1550-1552.

Lovely (2010) "y' Fibrinogen: Evaluation of a New Assay for Study of Associations with Cardiovascular Disease" Clin Chem 2010; 56(5):781-8.

Lovely et al. (2011) "Assessment of Genetic Determinants of the Association of y' Fibrinogen in Relation to Cardiovascular Disease" Arterioscler Thromb Vasc Biol. 31(10): 2345-2352.

Mannila et al. (2007) "Elevated plasma fibrinogen gamma' concentration is associated with myocardial infarction: effects of variation in fibrinogen genes and environmental factors" J Thromb Haemost 5(4):766-73 doi: 10.1111/j.1538-7836.2007.02406.x. Epub Jan. 22, 2007.

Meh et al. (1996) "Identification and Characterization of the Thrombin Binding Sites on Fibrin" J Biol Chem 271(38):23121-23125.

Mueller et al. (2006) "Increased pregnancy-associated plasma protein-A as a marker for peripheral atherosclerosis: results from the Linz Peripheral Arterial Disease Study" Clin Chem 52(6):1096-1103.

Papageorgiou et al. (2017) "Coronary Artery Atherosclerosis in Hypertensive Patients: The Role of Fibrinogen Genetic Variability" Rev Esp Cardiol. 70:34-41.

Parveen et al. (2015) "Pregnancy Associated Plasma Protein-A (PAPP-A) Levels in Acute Coronary Syndrome: A Case Control Study in a Tertiary Care Centre" Indian J Clin Biochem. 30(2): 150-154.

PCT International Preliminary Report on Patentability and Written Opinion dated Aug. 1, 2017 issued in PCT/US2016/015015.

PCT International Search Report and Written Opinion dated Feb. 24, 2021 issued in PCT/US2020/052912.

PCT International Search Report and Written Opinion dated Jul. 18, 2016 issued in PCT/US2016/015015.

(56) References Cited

OTHER PUBLICATIONS

Robbers et al. (2013) "Magnetic resonance imaging-defined areas of microvascular obstruction after acute myocardial infarction represent microvascular destruction and haemorrhage" Eur Heart J. 34:2346-2353.
Rohatgi et al. (2012) "Association of Growth Differentiation Factor-15 with Coronary Atherosclerosis and Mortality in a Young, Multiethnic Population: Observations from the Dallas Heart Study" Clinical Chemistry 58(1):172-182.
Tunac (2021) "Curative and Preventive Treatment for Cardiovascular Disease (CVD) Targeting Multiple Etiology" Cardiology and Cardiovascular Research 5(2): 103-125.
US Notice of Allowance dated Feb. 18, 2021 issued in U.S. Appl. No. 16/060,840.
US Notice of Allowance dated Jun. 9, 2021 issued in U.S. Appl. No. 16/060,840.
US Office Action dated May 18, 2020 issued in U.S. Appl. No. 16/060,840.
Van den Herik et al. (2011) "y'/total fibrinogen ratio is associated with short-term outcome in ischaemic stroke" Thromb Haemost 105(3):430-4; doi: 10.1160/TH10-09-0569. Epub Dec. 6, 2010.
Van den Herik et al. (2012) "Fibrinogeny'levels in patients with intracerebral hemorrhage" Thrombosis Research 129(6): 807-809.
Wallentin et al. (2014) "Growth Differentiation Factor 15, a Marker of Oxidative Stress and Inflammation, for Risk Assessment in Patients With Atrial Fibrillation" Circulation 130:1847-1858.
Wiklund et al. (2010) "Macrophage inhibitory cytokine-1 (MIC-1/GDF15): a new marker of all-cause mortality" Aging Cell 9: 1057-1064.
Wollert et al. (2017) "Growth Differentiation Factor 15 as a Biomarker in Cardiovascular Disease" Clinical Chemistry 63(1): 140-151.
Wu et al. (2016) "Level of Pregnancy-associated Plasma Protein-A Correlates With Coronary Thin-cap Fibroatheroma Burden in Patients With Coronary Artery Disease: Novel Findings From 3-Vessel Virtual Histology Intravascular Ultrasound Assessment" Medicine (Baltimore) 95(3):e2563 (7 pages).
Zengin et al. (2015) "The utility of pregnancy-associated plasma protein A for determination of prognosis in a cohort of patients with coronary artery disease" Biomark Med. 9:731-741 ((Epub ahead of print—10.2217/BMM.15.41 ISSN 1752-0363 11 pages).
Zimmers et al. (2005) "Growth differentiation factor-15/ macrophage inhibitory cytokine-1 induction after kidney and lung injury" Shock 23(6): 543-8.
CA Office Action dated May 17, 2024 in CA Application No. 3012985.
EP Extended European Search report dated Dec. 22, 2023 in EP Application No. 20868963.8.
EP Partial Supplementary European Search report dated Sep. 18, 2023, in Application No. EP20868963.8.
JP Office Action dated Jul. 8, 2024 in JP Application No. 2022-519782 with English translation.
Li, J., et al., "Circulating Glycocalyx Shedding Products as Biomarkers for Evaluating Prognosis of Patients With Out-of-hospital Cardiac Arrest After Return of Spontaneous Circulation, "Scientific reports, 2024, vol. 14(1), pp. 1-12.
U.S. Non-Final Office Action dated Feb. 13, 2023 in U.S. Appl. No. 17/469,714.
U.S. Notice of Allowance dated Jul. 17, 2023, in U.S. Appl. No. 17/469,714.
Van Dijk, A.C., et al., "Association Between Fibrinogen and Fibrinogen γ And Atherosclerotic Plaque Morphology and Composition in Symptomatic Carotid Artery Stenosis: Plaque-At-RISK study," Thrombosis Research, 2019, vol. 177, pp. 130-135.
Wadowski, P.P., et al., "Sublingual Functional Capillary Rarefaction in Chronic Heart Failure," European Journal of Clinical Investigation, 2017, vol. 48 (2), pp. 1-8.
JP Office Action dated Jan. 7, 2025 in JP Application No. 2022-519782, with English Translation.

* cited by examiner

| Group | Mice | Diet | Day 1 | Day 3 | Day 6 |
|---|---|---|---|---|---|
| 1 | 9 | High fat | PCB-77 | | |
| 2 | 9 | High fat | PCB-77 | | $1.5 \times 10^9$ *P. gingivalis* |
| 3 | 9 | High fat | $5 \times 10^9$ *P. gingivalis* | PCB-77 | $1.5 \times 10^9$ *P. gingivalis* |
| 4 | 9 | High fat | PCB-77 | PCB-77 | PCB-77 |
| 5 | 9 | High fat | | | |
| 6 | 3 | Normal | | | |

*FIG. 1A*

| Group | Mice | Dose of *P. gingivalis* |
|---|---|---|
| 1 | 4 | $5 \times 10^9$ |
| 2 | 4 | $1 \times 10^9$ |
| 3 | 4 | $1 \times 10^8$ |
| 4 | 4 | $1 \times 10^7$ |

*FIG. 1B*

Pathology: Mouse Model of Atherosclerosis

Developed Embotricin™, which reversed and prevented plaque

- created a proprietary atherosclerotic mouse, *Tunac arterial plaque* (TAP™) mouse model, treated with:
  *1. High fat diet, to create low ESS*
  *2. Polychlorinated biphenyl (PCB), an oxidative agent*
  *3. P. gingivalis, inflammatory infectious agent*

- plaques identified by histopathology: hearts and aortic sinus frozen, sectioned *(10 μm)*

Plaque correlated with shedding of glycocalyx components:

- syndecan-1 (SDC-1)
- hyaluronan (HAS-1)
- Heparan (HS)
- plasminogen activator inhibitor (PAI-1)

*Developed GlycoCardia*$^{CVD}$ biomarker panel

*(brachiocephalic artery X-section)*

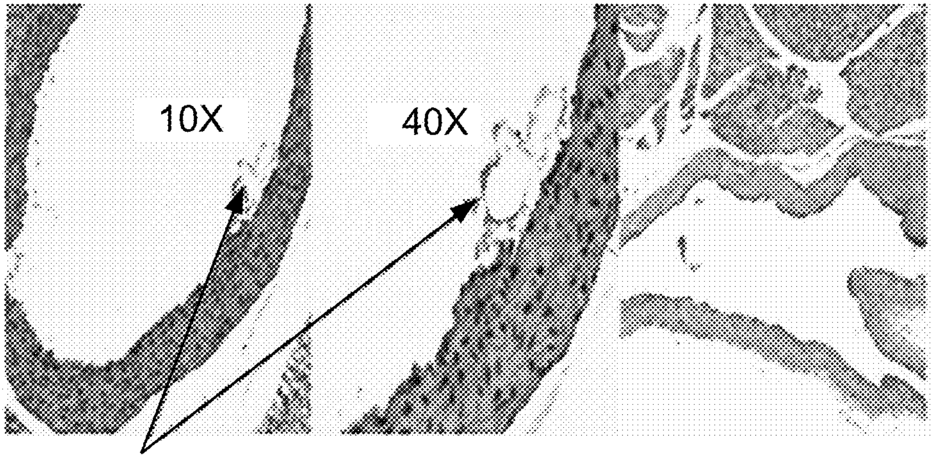

No drug = Plaque

Drug treated = no plaque

FIG. 10

Preventative

Compound B

Curative

Compound B

Preventative

Compound F

Curative

Compound F

Preventative

Compound I

Curative

Compound I

Preventative

Compound C

Curative

Compound C

Sample ‘fingerprints’ from a 7-biomarker panel

Blood levels of 7 biomarkers in 3 different CVD diseases (from published clinical data)

| Disease | (1) SDC-1 | (2) HAS-1 | (3) HS | (4) PAI-1 | (5) γ-fibrinogen | (6) GDF-15 | (7) PAPP-A |
|---|---|---|---|---|---|---|---|
| CHD | 780 ng/ml | 341 ng/ml | 590 ng/ml | 5,260 ng/ml | 2,800 ng/ml | 1.0 ng/ml | 650 ng/ml |
| HTN | 72 ng/ml | 325 ng/ml | 20,000 ng/ml | 39.8 ng/ml | 3,500,000 ng/ml | 0.813 ng/ml | 67.42 ng/ml |
| HF | 3.47 ng/ml | 0.36 ng/ml | trace | 41 ng/ml | 3,500,000 ng/ml | 1.3 ng/ml | 36.81 ng/ml |

FIG. 13

3-combo antiembolic™ drug

- *Drugs tested in 3-combo to address multifactor nature of CVD*
- *Drugs active individually, but curative/ preventive only in combo!*

| 3-combo drugs (FTX) | Blood Markers | | | | | |
|---|---|---|---|---|---|---|
| | 'Hyaluronan' | | "Heparan sulfate' | | 'PAI-1' | |
| | Preventive | Curative | Preventive | Curative | Preventive | Curative |
| A. 226/229/216 | | + | - | + | - | + |
| B. 226/229/214 | - | + | - | + | + | + |
| C. 226/229/218 | - | + | - | + | - | + |
| D. 226/229/219 | - | - | - | - | + | + |
| E. 226/229/230 | - | - | - | - | + | + |
| F. 224/216/214 | - | + | + | + | + | - |
| G. 224/216/219 | + | - | + | - | - | - |
| H. 224/216/219 | - | - | + | - | + | + |
| I. 216/214/218 | + | + | + | - | + | + |
| J. 216/214/219 | - | + | - | + | + | - |
| K. 214/218/219 | + | + | + | + | + | + |

Curative only (rows A–C)

- Curative: *atherosclerotic animal, then drug treatment*
- Preventive: *drug introduced before animal made atherosclerotic*

Curative/preventive (row K)

'Combo K' = Embotricin™ *(anti-embolic™ drug)*

*Anti-embolic™ – compound that prevents formation of emboli (clots) involving plaque reduction and/or restoration of disruptedendothelial glycocalyx*

*FIG. 14*

BIOMARKER PANEL TARGETED TO DISEASES DUE TO MULTIFACTORIAL ONTOLOGY OF GLYCOCALYX DISRUPTION

CROSS-REFERENCE TO RELATED APPLICATIONS

This application claims the benefit of U.S. provisional application No. 62/907,389, filed Sep. 27, 2019, which is hereby incorporated by reference in its entirety.

BACKGROUND

The epithelium is one of the four basic types of animal tissue, along with connective tissue, muscle tissue and nervous tissue. Epithelial tissues line the cavities and surfaces of structures throughout the body. Many glands are made up of epithelial cells. Functions of epithelial cells include secretion, selective absorption, protection, transcellular transport and detection of sensation. Cells of epithelial tissue are tightly packed and form a continuous sheet. Epithelial cells form glands and make up a major layer in mucosal membranes. Epithelial cells in mucosal surfaces are continuously faced with the critical function of forming a protective apical barrier that prevents cellular damage and infection while allowing the exchange of molecules with the extracellular milieu. Loss of barrier function is ascribed to numerous mucosal pathologies, such as dry eye, severe asthma, and inflammatory bowel disease. Epithelial tissue lines the mouth, lung alveoli, and kidney tubules. The lining of the blood and lymphatic vessels are of a specialized form of epithelium called endothelium.

The primary functions of epithelial tissues are: (1) to protect the tissues that lie beneath it from radiation, desiccation, toxins, invasion by pathogens, and physical trauma; (2) the regulation and exchange of chemicals between the underlying tissues and a body cavity; (3) the secretion of hormones into the blood vascular system, and/or the secretion of sweat, mucus, enzymes, and other products that are delivered by ducts; and (4) to provide sensation.

Most epithelial cells have a fuzz-like coat on the external surface of their plasma membranes called glycocalyx, a glycoprotein-polysaccharide covering that surrounds the cell membranes, including some bacteria. The existence of the glycocalyx was discovered about 40 years ago, when is was described as a thin layer at the endothelial surface (1966. Fed Proc 25:1773-1783). However, the significance of this structure was not recognized, partly because it is destroyed upon conventional tissue fixation and not seen in most light microscopic examinations. The glycocalyx is a protective lining at the surface of the endothelium found in every healthy blood vessel; it is made of proteoglycan, a complex network of protein (glycoprotein) and disaccharide sugar (glycosaminoglycan), which serve as backbone molecules for support. Generally, the carbohydrate portion of the glycolipids found on the surface of plasma membranes helps contributes to cell-cell recognition, communication, and intracellular adhesion. This complex network (originating from plasma and vessel wall) forms a dynamic layer between the flowing blood and the endothelium, continuously changing in thickness depending on shear or blood flow pressure. Thus, the shear generated by blood flow regulates the balance between biosynthesis and shedding of the various glycocalyx components. The core protein groups of this layer are syndecans and glypicans promiscuously bound with different glycosaminoglycan including heparan sulfate, chondroitin sulfate, dermatan sulfate, keratan sulfate, and hyaluronan (or hyaluronic acid). In the vasculature, heparan sulfate represents roughly 50-90% of the total amount of proteoglycans followed by chondroitin sulfate with a typical ratio of 4:1, respectively (2007.Pflugers Arch; 454:345-359).

The glycocalyx can also be found on the apical portion of the microvilli within the digestive tract, especially within the small intestine. It creates a meshwork 0.3 micrometers thick and consists of acidic mucopolysaccharides and glycoproteins that project from the apical plasma membrane of epithelial absorptive cells. It provides additional surface for adsorption and includes enzymes secreted by the absorptive cells that are essential for the final steps of digestion of proteins and sugars.

Each cell is surrounded by a glycocalyx. The glycocalyx layer of conjoined cells of a tissue form a glycocalyx layer of a tissue's surface and form a barrier. Once disrupted, the underlying cell is susceptible to disruption and immune attack by macrophages and the like. The glycocalyx of endothelial cells, such as the endometrium, the inner surface of the lungs, the microvilli of the kidney, the pancreas, etc., form a cellular seal.

Further, the glycocalyx at the cellular level supports the structural and functional integrity of the glycoproteins and other biomolecules passing there through. Biomolecules that form channels, receptors, and other functional components of the cell membrane structurally and functionally coexist with and through the glycocalyx. Disruption of the glycocalyx results in disruption of the structure and function of those biomolecules, thereby disrupting the structure and function of the cells, as well as the tissues, and organs comprised of those cells.

Other generalized functions effected by status of glycocalyx include protection (it cushions the plasma membrane and protects it from chemical injury), immunity to infection (it enables the immune system to recognize and selectively attack foreign organisms), defense against cancer (changes in the glycocalyx of cancerous cells enable the immune system to recognize and destroy them), transplant compatibility (it forms the basis for compatibility of blood transfusions, tissue grafts, and organ transplants), cell adhesion (it binds cells together so that tissues do not fall apart), inflammation regulation (glycocalyx coating on endothelial walls in blood vessels prevents leukocytes from rolling/binding in healthy states), fertilization (it enables sperm to recognize and bind to eggs), and embryonic development (it guides embryonic cells to their destinations).

SUMMARY

Various embodiments contemplated herein may include, but need not be limited to, one or more of the following:

- Embodiment 1: A kit including means for measuring at least two biomarkers selected from the group consisting of hyaluronan synthase-1 (HAS-1), heparan SO4 (HS), syndecan-1 (SDC-1), plasminogen activator inhibitor (PAI-1), gamma fibrinogen (GF), growth differentiation factor 15 (GDF-15), and pregnancy-associated plasma protein (PAPP-A), wherein at least one of the at least two biomarkers is selected from the group consisting of gamma fibrinogen (GF), growth differentiation factor 15 (GDF-15), and pregnancy-associated plasma protein (PAPP-A).
- Embodiment 2: The kit of embodiment 1, wherein the at least two biomarkers are selected from the group consisting of gamma fibrinogen (GF), growth differentiation factor 15 (GDF-15), and pregnancy-associated plasma protein (PAPP-A).

Embodiment 3: The kit of embodiment 2, wherein the kit includes means for measuring at least three biomarkers, the at least three biomarkers including gamma fibrinogen (GF), growth differentiation factor 15 (GDF-15), and pregnancy-associated plasma protein (PAPP-A).

Embodiment 4: The kit of any one of embodiments 1-3, wherein the means for measuring biomarkers comprise binding partners that specifically bind the biomarkers.

Embodiment 5: The kit of embodiment 4, wherein each binding partner in the kit is labeled with a different detectable label.

Embodiment 6: The kit of embodiment 4 or embodiment 5, wherein the binding partners comprise detectably labeled antibodies.

Embodiment 7: A method of treating a subject having disease characterized by disruption of the glycocalyx, the method including administering, or causing to be administered, to the subject one or more compositions characterized by Formulas I-XI:

(FORMULA I)

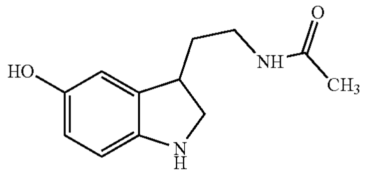

(FORMULA II)

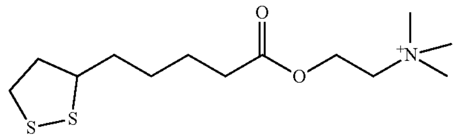

(FORMULA III)

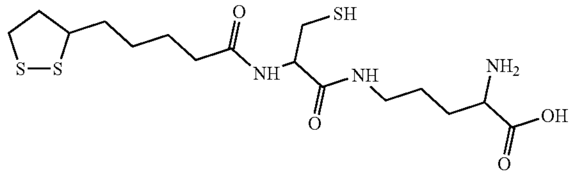

(FORMULA IV)

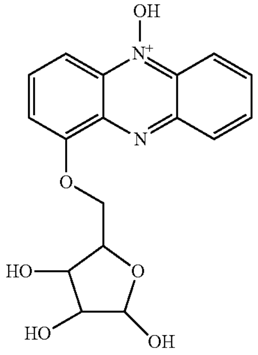

(FORMULA V)

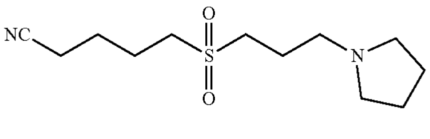

-continued (FORMULA VI)

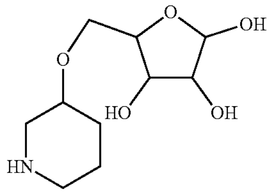

(FORMULA VII)

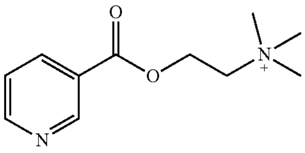

(FORMULA VIII)

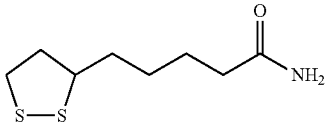

(FORMULA IX)

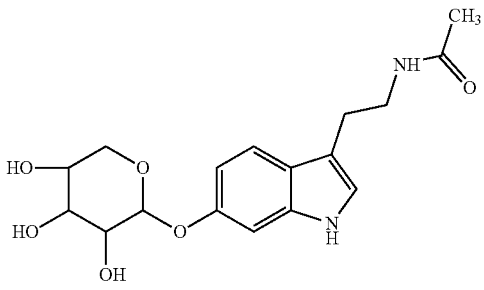

(FORMULA X)

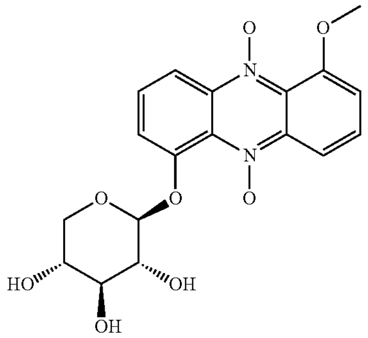

(FORMULA XI)

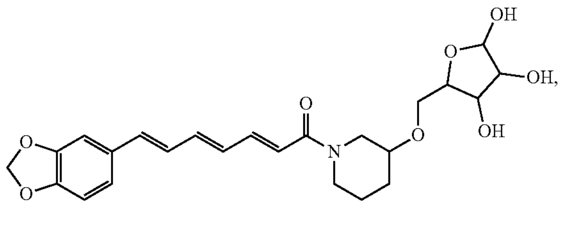

the subject being one previously identified as having a disease characterized by disruption of the glycocalyx by measuring at least two biomarkers selected from the group consisting of hyaluronan synthase-1 (HAS-1), heparan SO4 (HS), syndecan-1 (SDC-1), plasminogen activator inhibitor (PAI-1), gamma fibrinogen (GF), growth differentiation factor 15 (GDF-15), and pregnancy-associated plasma protein (PAPP-A).

Embodiment 8: The method of embodiment 7, wherein at least one of the at least two biomarkers measured is selected from the group consisting of gamma fibrinogen (GF), growth differentiation factor 15 (GDF-15), and pregnancy-associated plasma protein (PAPP-A).

Embodiment 9: The method of embodiment 8, wherein the at least two biomarkers measured are selected from the group consisting of gamma fibrinogen (GF), growth differentiation factor 15 (GDF-15), and pregnancy-associated plasma protein (PAPP-A).

Embodiment 10: The method of embodiment 9, wherein at least three biomarkers are measured, the at least three biomarkers including gamma fibrinogen (GF), growth differentiation factor 15 (GDF-15), and pregnancy-associated plasma protein (PAPP-A).

Embodiment 11: The method of any one of embodiments 7-10, wherein the method additionally includes measuring the biomarkers or causing them to be measured.

Embodiment 12: A method for detecting biomarkers of glycocalyx integrity in a subject, the method including measuring, or causing to be measured, the levels of at least two biomarkers in a biological sample obtained from the subject, the at least two biomarkers being selected from the group consisting of hyaluronan synthase-1 (HAS-1), heparan SO4 (HS), syndecan-1 (SDC-1), plasminogen activator inhibitor (PAI-1), gamma fibrinogen (GF), growth differentiation factor 15 (GDF-15), and pregnancy-associated plasma protein (PAPP-A), wherein at least one of the at least two biomarkers measured is selected from the group consisting of gamma fibrinogen (GF), growth differentiation factor 15 (GDF-15), and pregnancy-associated plasma protein (PAPP-A).

Embodiment 13: The method of embodiment 12, wherein the at least two biomarkers measured are selected from the group consisting of gamma fibrinogen (GF), growth differentiation factor 15 (GDF-15), and pregnancy-associated plasma protein (PAPP-A).

Embodiment 14: The method of embodiment 13, wherein at least three biomarkers are measured, the at least three biomarkers including gamma fibrinogen (GF), growth differentiation factor 15 (GDF-15), and pregnancy-associated plasma protein (PAPP-A).

Embodiment 15: The method of any one of embodiments 12-14, wherein the at least two biomarkers are measured.

Embodiment 16: The method of embodiment 15, wherein the biological sample is selected from the group consisting of blood, plasma, urine, saliva, tears, and cerebral spinal fluid.

Embodiment 17: The method of embodiment 15 or embodiment 16, wherein the biomarkers are measured using an immunoassay or mass spectrometry.

Embodiment 18: The method of any one of embodiments 12-17, wherein an elevated level of one of the at least two biomarkers, as compared to a predetermined normal level, indicates that the subject has a disease characterized by disruption of the glycocalyx.

Embodiment 19: The method of any one of embodiments 12-18, wherein the subject has one or more symptoms consistent with at least two possible diseases or two possible stages of one disease, and the method includes: measuring, or causing to be measured, at least two of said biomarkers to provide a biomarker signature; and identifying the subject as a candidate for treatment of one of at least two possible diseases or stages of disease, based on the biomarker signature.

Embodiment 20: The method of embodiment 19, wherein the method includes measuring, or causing to be measured, at least three of said biomarkers to provide a biomarker signature.

Embodiment 21: The method of embodiment 19, wherein the method additionally includes treating the subject for said one of at least two possible diseases or stages of disease.

Embodiment 22: A method of treating a subject having one or more symptoms consistent with at least two possible diseases or two possible stages of one disease, the subject being one previously identified as having one of the two possible diseases or stages of disease by measuring at least two biomarkers selected from the group consisting of hyaluronan synthase-1 (HAS-1), heparan SO4 (HS), syndecan-1 (SDC-1), plasminogen activator inhibitor (PAI-1), gamma fibrinogen (GF), growth differentiation factor 15 (GDF-15), and pregnancy-associated plasma protein (PAPP-A) to determine a biological signature indicative of said one of at least two possible diseases, the method including treating the subject for said one of at least two possible diseases or stages of disease.

Embodiment 23: The method of embodiment 22, wherein the method includes administering, or causing to be administered, to the subject one or more compositions characterized by one or more of Formulas I-XI:

FORMULA I)

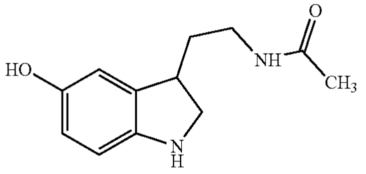

(FORMULA II)

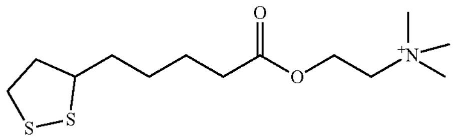

(FORMULA III)

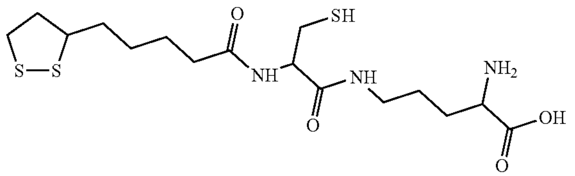

(FORMULA IV)

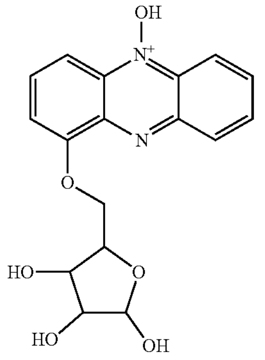

-continued (FORMULA V)

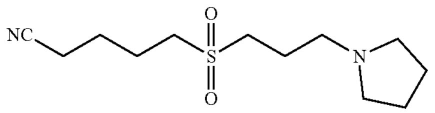

(FORMULA VI)

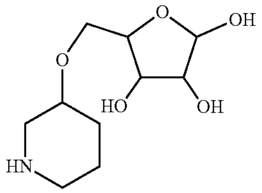

(FORMULA VII)

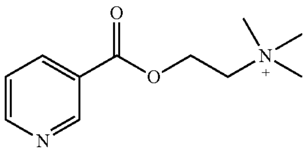

(FORMULA VIII)

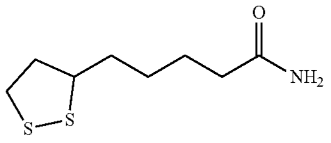

(FORMULA IX)

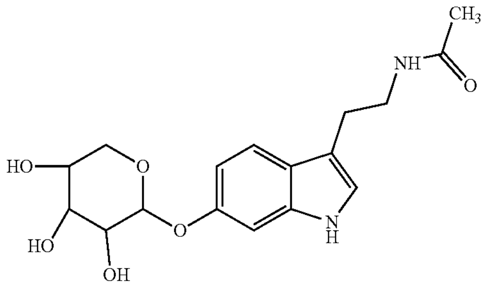

(FORMULA X)

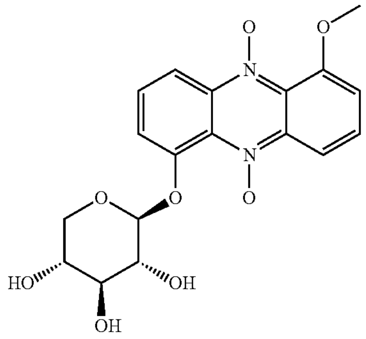

(FORMULA XI)

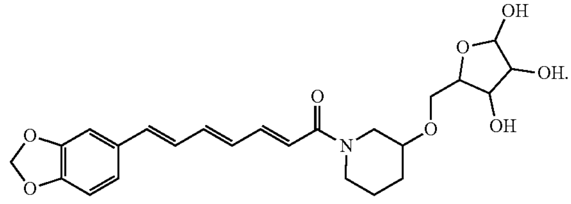

Embodiment 24: The method of any one of embodiments 12-17, wherein the subject includes a non-human test subject.

Embodiment 25: The method of embodiment 24, wherein the method includes administering a candidate drug to the test subject.

Embodiment 26: The method of embodiment 25, wherein the candidate drug is administered to the subject before measuring the levels of the biomarkers.

Embodiment 27: The method of any one of embodiments 24-26, wherein the test subject includes an animal model of a disease characterized by disruption of the glycocalyx, endothelial inflammation, oxidative damage to the endothelium.

Embodiment 28: The method of embodiment 27, wherein the condition includes arterial inflammation and/or plaque.

Embodiment 29: The method of any one of embodiments 24-28, wherein the test subject is produced from a mammal by one or more treatments selected from the group consisting of: administering a xenobiotic to the mammal; administering a pathogen to the mammal; and feeding the mammal an at least 21% (weight/weight) fat diet.

Embodiment 30: The method of embodiment 29, wherein the test subject is produced by: administering a polychlorobiphenyl (PCB) to the mammal; administering a bacterium to the mammal; and feeding the mammal an at least 50% fat diet.

Embodiment 31: The method of embodiment 30, wherein the test subject is a mouse test subject produced by: administering 3,3',4,4'-tetrachlorobiphenyl (PCB-77) to the mouse; administering *Porphyromonas gingivalis* to the mouse; and feeding the mammal an at least 60% fat diet.

Embodiment 32: The method of embodiment 31, wherein: PCB-77 is administered at a dose of at least 150 μmol/kg; and *Porphyromonas gingivalis* is administered at a dose of at least $3\times10^{11}$ bacteria per mouse.

Embodiment 33: The method of any one of embodiments 24-32, wherein the candidate drug has been demonstrated to have an activity selected from the group consisting of anti-inflammatory activity, anti-oxidant activity, activity in reducing disruption of the glycocalyx, and any combination thereof.

Embodiment 34: The method of embodiment 33, wherein the candidate drug has been has been demonstrated to have anti-inflammatory activity, anti-oxidant activity, and activity in reducing disruption of the glycocalyx, and the candidate drug includes a combination of FTX compounds.

Embodiment 35: The kit of any one of embodiments 1-5, wherein the kit includes means for measuring at least four biomarkers selected from the group consisting of hyaluronan synthase-1 (HAS-1), heparan SO4 (HS), syndecan-1 (SDC-1), plasminogen activator inhibitor (PAI-1), gamma fibrinogen (GF), growth differentiation factor 15 (GDF-15), and pregnancy-associated plasma protein (PAPP-A); or the method of any one of embodiments 7-34, wherein at least four biomarkers selected from the group consisting of hyaluronan synthase-1 (HAS-1), heparan SO4 (HS), syndecan-1 (SDC-1), plasminogen activator inhibitor (PAI-1), gamma fibrinogen (GF), growth differentiation factor 15 (GDF-15), and pregnancy-associated plasma protein (PAPP-A) are measured.

Embodiment 36: The kit of any one of embodiments 1-5, wherein the kit includes means for measuring the biomarkers hyaluronan synthase-1 (HAS-1), heparan SO4 (HS), syndecan-1 (SDC-1), plasminogen activator inhibitor (PAI-1), gamma fibrinogen (GF), growth differentiation factor 15 (GDF-15), and pregnancy-associated plasma protein (PAPP-A); or the method of any one of embodiments 7-34, wherein the biomarkers measured comprise hyaluronan synthase-1 (HAS-1), heparan SO4 (HS), syndecan-1 (SDC-1), plasminogen activator inhibitor (PAI-1), gamma fibrinogen (GF), growth differentiation factor 15 (GDF-15), and pregnancy-associated plasma protein (PAPP-A).

Embodiment 37: The kit of any one of embodiments 1-5, wherein the kit consists of means for measuring the biomarkers hyaluronan synthase-1 (HAS-1), heparan SO4 (HS), syndecan-1 (SDC-1), plasminogen activator inhibitor (PAI-1), gamma fibrinogen (GF), growth differentiation factor 15 (GDF-15), and pregnancy-associated plasma protein (PAPP-A); or the method of any one of embodiments 7-34, wherein the biomarkers measured consist of hyaluronan synthase-1 (HAS-1), heparan SO4 (HS), syndecan-1 (SDC-1), plasminogen activator inhibitor (PAI-1), gamma fibrinogen (GF), growth differentiation factor 15 (GDF-15), and pregnancy-associated plasma protein (PAPP-A).

Embodiment 38: The kit of any one of embodiments 1-5, wherein the kit includes means for measuring the biomarker gamma fibrinogen (GF); or the method of any one of embodiments 7-34, wherein at least one biomarker measured includes gamma fibrinogen (GF).

Embodiment 39: The kit or method of embodiment 38, wherein: the kit additionally includes means for measuring the biomarker growth differentiation factor 15 (GDF-15); or the method wherein at least one biomarker measured includes growth differentiation factor 15 (GDF-15).

Embodiment 40: The kit of any one of embodiments 1-5, wherein the kit includes means for measuring the biomarker growth differentiation factor 15 (GDF-15); or the method of any one of embodiments 7-34, wherein at least one biomarker measured includes growth differentiation factor 15 (GDF-15).

Embodiment 41: The kit or method of embodiment 38 or embodiment 40, wherein: the kit additionally includes means for measuring the biomarker pregnancy-associated plasma protein (PAPP-A); or the method wherein at least one biomarker measured includes pregnancy-associated plasma protein (PAPP-A).

Embodiment 42: The kit of any one of embodiments 1-5, wherein the kit includes means for measuring the biomarker pregnancy-associated plasma protein (PAPP-A); or the method of any one of embodiments 7-34, wherein at least one biomarker measured includes pregnancy-associated plasma protein (PAPP-A).

Embodiment 43: The kit or method of any one of embodiments 38-42, wherein: the kit additionally includes means for measuring the biomarker hyaluronan synthase-1 (HAS-1); or the method wherein at least one biomarker measured includes hyaluronan synthase-1 (HAS-1).

Embodiment 44: The kit or method of any one of embodiments 38-43, wherein: the kit additionally includes means for measuring the biomarker heparan SO4 (HS); or the method wherein at least one biomarker measured includes heparan SO4 (HS).

Embodiment 45: The kit or method of any one of embodiments 38-44, wherein: the kit additionally includes means for measuring the biomarker syndecan-1 (SDC-1); or the method wherein at least one biomarker measured includes syndecan-1 (SDC-1).

Embodiment 46: The kit or method of any one of embodiments 38-45, wherein: the kit additionally includes means for measuring the biomarker plasminogen activator inhibitor (PAI-1); or the method wherein at least one biomarker measured includes plasminogen activator inhibitor (PAI-1).

Embodiment 47: The method of any one of embodiments 7-11 and 23, wherein the composition characterized by Formula I is administered.

Embodiment 48: The method of any one of embodiments 7-11, and 23, wherein the composition characterized by Formula II is administered.

Embodiment 49: The method of any one of embodiments 7-11, and 23, wherein the composition characterized by Formula III is administered.

Embodiment 50: The method of any one of embodiments 7-11, and 23, wherein the composition characterized by Formula IV is administered.

Embodiment 51: The method of any one of embodiments 7-11, and 23, wherein the composition characterized by Formula V is administered.

Embodiment 52: The method of any one of embodiments 7-11, and 23, wherein the composition characterized by Formula VI is administered.

Embodiment 53: The method of any one of embodiments 7-11, and 23, wherein the composition characterized by Formula VII is administered.

Embodiment 54: The method of any one of embodiments 7-11, and 23, wherein the composition characterized by Formula VIII is administered.

Embodiment 55: The method of any one of embodiments 7-11, and 23, wherein the composition characterized by Formula IX is administered.

Embodiment 56: The method of any one of embodiments 7-11, and 23, wherein the composition characterized by Formula X is administered.

Embodiment 57: The method of any one of embodiments 7-11, and 23, wherein the composition characterized by Formula XI is administered.

Embodiment 58: The method of any one of embodiments 47-57, wherein a second composition is co-administered with the composition, the second composition being different from the composition, wherein the second composition is characterized by one of Formulas I-XI.

Embodiment 59: The method of embodiment 58, wherein a third composition is co-administered with the composition and the second composition, the third composition being different from the composition and the second composition, wherein the third composition is characterized by one of Formulas I-XI.

Embodiment 60: The method of embodiment 59, wherein: (a) the composition is characterized by Formula I, the second composition is characterized by Formula II, and the third composition is characterized by Formula III; (b) the composition is characterized by Formula I, the second composition is characterized by Formula VI, and the third composition is characterized by Formula VII; (c) the composition is characterized by Formula I, the second composition is characterized by Formula IV, and the third composition is characterized by Formula V; and (d) the composition is characterized by Formula II, the second composition is characterized by Formula VI, and the third composition is characterized by Formula VII.

Embodiment 61: The method of any one of embodiments 47-60, wherein the method includes administering, or causing to be administered, to the subject a therapeutic agent selected from the group consisting of an antihistamine, an anti-infective agent, an antineoplastic agent, an autonomic drug, a blood derivative, a blood formation agent, a coagulation agent, a thrombosis agent, a cardiovascular drug, a cellular therapy, a central nervous system agent, a contraceptive, a dental agent, a diagnostic agent, a disinfectant, an electrolytic agent, a caloric agent, a water balance agent, an enzyme, a respiratory tract agent, an eye preparation, an ear preparation, a nose preparation, a throat preparation, a gold compound, a heavy metal antagonist, a hormone or synthetic substitute therefor, an oxytocic, a radioFTX compound, a serum, a toxoid, a vaccine, a skin and/or mucous membrane agent, a smooth muscle relaxant, a vitamin, and combinations thereof.

Embodiment 62: The method of any one of embodiments 7-23, the kit or method of any one of embodiments 38-46, or the method of any one of embodiments 47-60, wherein the subject has a disease characterized by a disrupted glycocalyx, endothelial inflammation, oxidative damage to the endothelium, or any combination thereof.

Embodiment 63: The method of embodiment 62, wherein the subject has cardiovascular disease (CVD).

Embodiment 64: The method of embodiment 63, wherein the subject has a form of cardiovascular disease (CVD) selected from the group consisting of coronary heart disease, myocardial infarction, stroke, hypertension, atrial fibrillation, congestive heart failure, congenital heart condition, peripheral arterial disease, venous thrombosis, deep venous thrombosis, pulmonary embolism, and any combination thereof.

Embodiment 65: The method of embodiment 62, wherein the subject has a condition selected from the group consisting of cancer, diabetes, arthritis, Alzheimer's disease, or any combination thereof.

Embodiment 66: The method of any one of embodiments 62-65, wherein the subject is known to have, or be at risk for, said condition or disease.

Embodiment 67: The method of any one of embodiments 62-66, wherein the method includes improving the integrity of the glycocalyx, reducing endothelial inflammation or oxidative damage to the endothelium, or any combination thereof.

Embodiment 68: The method of any one of embodiments 62-67, wherein the method includes measuring the disruption of the glycocalyx, endothelial inflammation, oxidative damage to the endothelium or any combination thereof after administration of the composition.

Embodiment 69: The method of any one of embodiments 62-68, wherein the glycocalyx or endothelium is in a region of the body selected from the group consisting of a gland, mouth, lung, kidney, eye, blood vessel, and endometrial or digestive tract lining.

Embodiment 70: The method of any one of embodiments 62-69, wherein the composition is administered to the subject in an oral formulation.

Embodiment 71: The method of any one of embodiments 62-70, wherein the composition is administered at a dose ranging from 0.05 mg/kg to 200.0 mg/kg.

Embodiment 72: The method of embodiment 71, wherein the dose ranges from 0.1 mg/kg to 100 mg/kg.

BRIEF DESCRIPTION OF THE DRAWINGS

FIGS. 1A and 1B are charts of experimental protocols.

FIG. 10 shows a photograph of plaque at 10×, a photograph of plaque at 40×, and a photograph of a normal arterial wall.

FIG. 13 shows sample biomarker "signatures," defined by patterns of absolute or relative biomarker levels for three different cardiovascular diseases when clinical data are analyzed using a 7-biomarker combination.

FIG. 14 is a chart showing the effects of different three-drug combinations, as assessed using the biomarkers hyaluronan synthase-2 ("Hyaluronan"), heparan sulfate, and plasminogen activator inhibitor ("PAI-1").

DETAILED DESCRIPTION

Figure 2A:
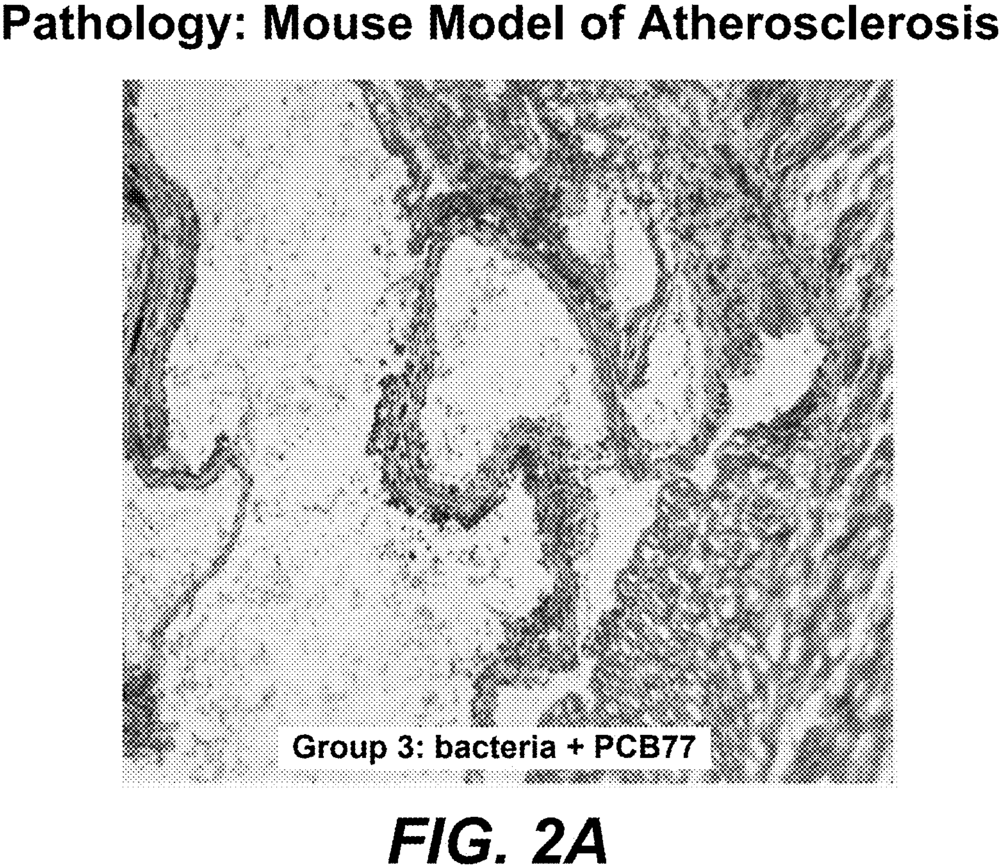
FIGS. 2A and 2B are photomicrographs of sections of group 3 and group 4 from Example 1.

In some embodiments, the present disclosure is generally directed to methods and compositions that restore the glycocalyx. Disruption of the glycocalyx is at the root of many diseases, especially cardiovascular disease. The compositions of the present disclosure maintain the integrity of glycocalyx in many different membranes.

Definitions

Terms used in the claims and specification are defined as set forth below unless otherwise specified.

"Vascular disease," as used herein, refers to any disease affecting the circulatory system of arteries, veins, capillaries, and lymph vessels in the body. Vascular disease can include, but is not limited to, peripheral artery disease, aneurysms, renal artery disease, Raynaud's disease, Buerger's disease, peripheral venous disease, varicose veins, blood clots (thromboembolism), blood clotting disorders, and lymphedema.

A "thrombus" is a solid mass consisting of platelets, fibrin and blood components.

An "embolus" is a piece of thrombus broken free and carried into the bloodstream.

A "thromboembolus is a floating embolus that becomes lodged in a blood vessel and blocks blood flow "Thromboembolism," as used herein, refers to obstruction of a blood vessel by a blood clot, which can occur in a family of vascular diseases including coronary heart disease (CHD), acute myocardial infarction (MI), stroke, hypertension, atrial fibrillation, congestive heart failure (CHF), congenital heart condition, peripheral arterial disease (PAD), chronic venous insufficiency (CVI), deep venous thrombosis (DVT), and pulmonary embolism (PE).

"Cardiovascular disease" (CVD) includes a family of diseases affecting both arteries and veins, as well as the heart: diseases in the arteries include coronary heart disease (CHD), myocardial infarction (MI), stroke, hypertension, atrial fibrillation, congestive heart failure (CHF), congenital heart condition, and peripheral arterial disease (PAD); diseases in the veins include venous thrombosis, deep venous thrombosis (DVT), and pulmonary embolism (PE).

"Coronary heart disease" (CHD) results from the effects of atherosclerotic plaque formation in coronary arteries. The reduction in blood supply to the heart muscles reduce the heart's efficiency and can cause heart failure. One of the first and major symptoms of this condition is angina (chest pain caused by reduced blood flow to the heart muscle).

"Myocardial infarction" (MI), commonly known as heart attack, is the irreversible necrosis of heart muscle due to prolonged interruption of blood supply (ischemia). The heart requires constant supply of oxygen and nutrients; if one of the arteries or branches becomes blocked suddenly, the heart is starved of oxygen, a condition called "cardiac ischemia." If cardiac ischemia lasts too long, the starved heart tissue dies, which is called heart attack (myocardial infarction), literally, "death of heart muscle."

"Stroke" occurs when brain cells die owing to a lack of blood supply, which may be classified as ischemic or hemorrhagic: ischemic stroke involves decreased blood supply to parts of the brain, leading to brain cell death and thus brain dysfunction; hemorrhagic stroke is due to rupture of a blood vessel or abnormal vascular structure, causing accumulation of blood in a part of the brain. The majority of strokes (80%) are ischemic in nature.

"Hypertension" or "high blood pressure" is defined as a condition wherein the pressure of the blood flowing through blood vessels remains high for a prolonged period, irrespective of the body's need. An increased blood pressure leads the heart to work harder, which makes the heart and arteries more susceptible to injury. Hypertension further increases the risk of incidents such as heart attack, heart failure, and atherosclerosis.

Cardiac arrhythmias are heart rhythm problems, which occur when heartbeats are not well coordinated owing to improper electric impulses. This may cause the heart to beat too fast (tachycardia) or too slowly (bradycardia). Arrhythmias are generally harmless and momentary, but frequent rhythm disturbances increase the risk of stroke and congestive heart failure. Atrial fibrillation is the most common sustained arrhythmia.

"Congestive heart failure" (CHF) is a condition wherein the heart fails to supply blood to the various parts of the body. This can be due to narrowed arteries, myocardial infarction, heart valve disease, high blood pressure, cardiomyopathy, or congenital abnormalities.

"Peripheral artery disease" (PAD) is a vascular disorder in which the thickening of arteries causes reduction in blood flow to limbs, leading to intermittent leg pain while walking. The disease is an indicator of atherosclerosis. It leads to sores (that do not heal) and gangrene.

"Deep Vein Thrombosis" (DVT) is a blood clot that usually forms in the deep veins of the lower leg or arm, which can block the venous return. A DVT may cause leg pain or swelling but can also present no symptoms. DVT is not usually life threatening, but it can become so if the blood clot breaks loose and lodges into the lungs. This is known as a "pulmonary embolism" (PE).

The term "healthy" as used herein refers to a state of an organ or individual that is free from disease (e.g., vascular disease), is in good health, and has no particular, known, physiologically based risk of developing the disease (e.g., vascular disease).

The term "compound," as used herein, refers to "a substance including atoms or ions of two or more different elements in definite proportions joined by chemical bonds into a molecule.

The term "composition," as used herein, refers to a substance that includes a compound, often in combination with other compounds or elements.

"Disrupting" or "disruption of" the glycocalyx, as used herein refers to any process or disease state that affects the glycocalyx such that it is not functioning normally. Disruption can be caused by inflammation or oxidation in the body. Disruption can cause the glycocalyx to thin and lose its component proteoglycans. For example, the dimensions or percentage of glycocalyx relating to blood vessels are:

| | Vessel Diameter (nm) | Glycocalyx Thickness (nm) | % Glycocalyx |
|---|---|---|---|
| Venules | 20,900 | 638 | 3.05 |
| Arterioles | 18,000 | 551 | 3.06 |
| Capillaries | 8,200 | 348 | 4.24 |

Thus, disruption means abnormal shedding of glycocalyx resulting in the loss of integrity and thickness, particularly a glycocalyx thickness less than 3.0% the diameter of venules or arterioles, and a glycocalyx thickness of less than 4.2% the diameter of capillaries.

An agent is said to have "activity in reducing disruption of the glycocalyx" if the agent reduces disruption of the glycocalyx as determined by any means described herein or known in the art.

"Inflammation," as used herein, refers to a protective response of tissue to injury or destruction in order to eliminate or cordon off any injurious agent and the injured tissue and initiate tissue repair. Inflammation can cause pain, heat, redness, swelling, and loss of function. Inflammatory mediators (cytokines and chemoattractants) can cause shedding of the glycocalyx. Inflammation can also cause leukocytes to degranulate, releasing enzymes that can degrade the glycocalyx.

"Anti-inflammatory," as used herein refers to a molecule, compound, or composition that inhibits any inflammatory process or symptom thereof, such as those described herein or otherwise known in the art. An anti-inflammatory is said to have "anti-inflammatory activity."

"Oxidative damage," "oxidative stress," or "oxidation," as used herein, refers to an imbalance of reactive oxygen species (ROS) and the body's ability to detoxify reactive intermediates and repair damage caused by ROS. Inflammation can cause the release of ROS. The presence of ROS can cause significant damage to cell structures, including the glycocalyx. On a molecular level, "oxidation" refers to the loss of electrons during a reaction by a molecule, atom or ion.

As used herein, the term "symptom" refers to a mental or physical manifestation that is regarded as indicating a disease or condition.

The term "symptom-targeted drug," as used herein refers to a drug that ameliorates a symptom of a disease or condition that may or may not address the underlying pathology.

The term "treat" when used with reference to treating, e.g., a disease or condition refers to the mitigation and/or elimination of one or more symptoms of that disease or condition, and/or a delay in the progression and/or a reduction in the rate of onset or severity of one or more symptoms of that disease or condition, and/or the prevention of that disease or condition. The term treat encompasses therapeutic treatment, as well as prophylactic treatment which includes a delay in the onset or the prevention of the onset of a disease or condition.

An amount of a therapeutic compound is said to be "s" when the amount is effective to achieve improvement including but not limited to improved survival rate or more rapid recovery, or improvement or elimination of a symptom and other indicator (such as a biomarker) as are selected as appropriate measures by those skilled in the art.

"Antioxidant," as used herein, refers to a molecule that inhibits the oxidation of other molecules and is able to neutralize or eliminate ROS. An antioxidant is said to have "anti-oxidant activity."

The term "assay," as used herein, refers to a procedure that determines the amount of a particular constituent of a mixture or sample. "Assay" is used interchangeably with the term "test" herein.

The term "biomarker," as used, herein refers to a substance, such as, but not limited to, a protein, DNA sequence, RNA sequence, or other biological substance or substances that, when detected, indicates a particular healthy or unhealthy state of an individual with respect to a disease (e.g., vascular disease).

The term "sample," as used herein, typically refers to a biological sample from an individual, and can be, but is not limited to, blood, plasma, urine, saliva, tears, or cerebral spinal fluid (CSF).

As used herein, the term "biomarker panel" generally refers to combination of reagents useful in detecting a plurality of biomarkers. A biomarker panel is typically provided in a kit for detecting two or more biomarkers. In the art, the term "biomarker panel" may be used to refer to a combination of biomarkers per se (as opposed to reagents for detecting the biomarkers); the sense in which this term is used herein will be readily apparent to those of skill in the art from the context in which this term is used.

"Detectable labels" include any composition detectable by spectroscopic, photochemical, biochemical, immunochemical, electrical, optical, or chemical means. Useful labels include magnetic beads (e.g., Dynabeads™), fluorescent dyes (e.g., fluorescein, Texas red, rhodamine, green fluorescent protein, and the like, see, e.g., Molecular Probes, Eugene, Oregon, USA), chemiluminescent compounds such as acridinium (e.g., acridinium-9-carboxamide), phenanthridinium, dioxetanes, luminol and the like, radiolabels (e.g., $^{3}H$, $^{125}I$, $^{35}S$, $^{14}C$, or $^{32}P$), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively.

A typical full-length (intact) immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments that can be produced, inter alia, by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $(Fab')_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes whole antibodies, antibody fragments either produced by the modification of whole antibodies or synthesized de novo using recombinant DNA methodologies. In certain embodiments antibodies include single chain antibodies (antibodies that exist as a single polypeptide chain), for example, single chain Fv antibodies (scFv) in which a variable heavy and a variable light chain are joined together (directly or through a peptide linker) to form a continuous polypeptide. In certain embodiments the single chain Fv antibody is a covalently linked $V_H$-$V_L$ heterodimer that may be expressed from a nucleic acid including $V_H$ and $V_L$ encoding sequences either joined directly or joined by a peptide-encoding linker (see, e.g., Huston, et al. (1988) Proc. Nat. Acad. Sci. USA, 85:5879-5883). While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example, Fab molecules can be displayed on phage if one of the chains (heavy or light) is fused, for example, to g3 capsid protein and the complementary chain exported to the periplasm as a soluble molecule. The two chains can be encoded on the same or on different replicons. The important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405, and 4,956,778). Accordingly, in certain embodiments, anti-Fc receptor antibodies include, but are not limited to all that have been displayed on phage or yeast (e.g., scFv, Fv, Fab and disulfide linked Fv (see, e.g., Reiter et al. (1995) Protein Eng. 8: 1323-1331)).

Antibodies also include "single-domain" antibodies (sdAbs), also known as a nanobodies. Single-domain antibodies consist of a single monomeric variable antibody domain. Like a common "whole antibody," it is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain). Some species, such as camelids, produce single-domain antibodies naturally.

The term "monoclonal antibody" refers to an antibody obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are typically highly specific, being directed against a single epitope. In contrast to polyclonal antibody preparations which typically include different antibodies directed against different determinants (epitopes), each monoclonal antibody is directed against a single determinant on the antigen. The term "monoclonal" indicates the character of the antibody as being obtained from, or one of, a substantially homogeneous population of antibodies, and is not to be construed as requiring production of the antibody by any particular method. For example, monoclonal antibodies may be made by a variety of techniques, including, but not limited to, the hybridoma method (see, e.g., Kohler and Milstein. (1975) *Nature,* 256:495-497; Hongo et al. (1995) *Hybridoma,* 14 (3): 253-260; Harlow et al. (1988) *Antibodies: A Laboratory Manual* (Cold Spring Harbor Laboratory Press, 2d ed.); Hammerling et al. (1981) In: *Monoclonal Antibodies and T-Cell Hybridomas* 563-681 (Elsevier, N.Y.)), recombinant DNA methods (see, e.g., U.S. Pat. No. 4,816,567), phage-display technologies (see, e.g., Clackson et al. (1991) *Nature,* 352:624-628; Marks et al. (1992) *J. Mol. Biol.* 222:581-597; Sidhu et al. (2004) *J. Mol. Biol.* 338(2): 299-310; Lee et al. (2004) *J. Mol. Biol.* 340(5): 1073-1093; and the like), and technologies for producing human or human-like antibodies in animals that have parts or all of the human immunoglobulin loci or genes encoding human immunoglobulin sequences (see, e.g., PCT Patent Publication Nos: WO 1998/24893; WO 1996/34096; WO 1996/33735; and WO 1991/10741; U.S. Pat. Nos. 5,545,807; 5,545,806; 5,569,825; 5,625,126; 5,633,425; and 5,661,016; Jakobovits et al. (1993) *Nature* 362:255-258; Bruggemann et al. (1993) *Year in Immunol.* 7:33; Marks et al. (1992) *Bio/Technology* 10:779-783; Lonberg et al. (1994) *Nature* 368:856-859; Morrison (1994) *Nature* 368:812-813; Fishwild et al. (1996) *Nature Biotechnol.* 14:845-851); Neuberger (1996) *Nature Biotechnol.* 14:826; Lonberg and Fluszar (1995) *Intern. Rev. Immunol.* 13:65-93; and the like).

As used herein, the phrase "causing to be measured" refers to any action resulting in a measurement being taken. For example, a physician causes a biomarker to be measured when the physician orders a test for that biomarker to be performed on a sample from a given subject.

As used herein, a "biomarker signature" refers to a pattern of absolute or relative biomarker levels for two or more biomarkers that is characteristic of a particular disease or condition or stage of disease or condition.

As used herein with reference to a disease or condition, the term "stage" refers to the level of biological severity of the disease or condition. Many diseases have well-defined staging criteria.

As used herein, the term "xenobiotic" refers to a substance, typically a chemical, that is foreign to a body, wherein chronic exposure to the body results in a deleterious effect (on the body), manifested as one or more chronic diseases, herein defined as "xenodiscases."

A "pathogen" is a microorganism (e.g., a bacterium or virus) that can cause infectious disease.

As used herein, the term "differential diagnosis" refers to the determination of which of two or more diseases with similar symptoms is likely responsible for a subject's symptom(s), based on an analysis of the clinical data.

The term "prognosis" is used herein to refer to the likely course of a disease or condition.

The Glycocalyx and Disease

The glycocalyx is a key structure for maintaining vascular wall integrity and the proper function of many organs. Disruptions in the glycocalyx can be due to: contact with fluid flow or low shear stress particularly at arterial bends and bifurcations; physical damage or injury; infections or exposure to xenobiotics; oxidation and inflammation; and loss of protective enzymes and proteins. An unimpeded blood flow, particularly on straight segments of arterial vessels with high shear stress is typically characterized by a thick glycocalyx layer and the absence of plaque. A thin glycocalyx promotes plaque buildup, especially where there is whirlpool blood flow with low shear in vascular bends. Plaques are essentially patches that cover tiny gaps to maintain osmotic balance of membranes. The tiny gaps in the membrane leak electrolytes both into (Na+Cl−, Ca+, HCO3) and out of (K+, PO4−, Mg+) cells, which can lead to a family of cardiovascular diseases. Disruptions can also be caused by debris trapped in the stagnant blood flow, which triggers oxidation and inflammation.

Figure 11:
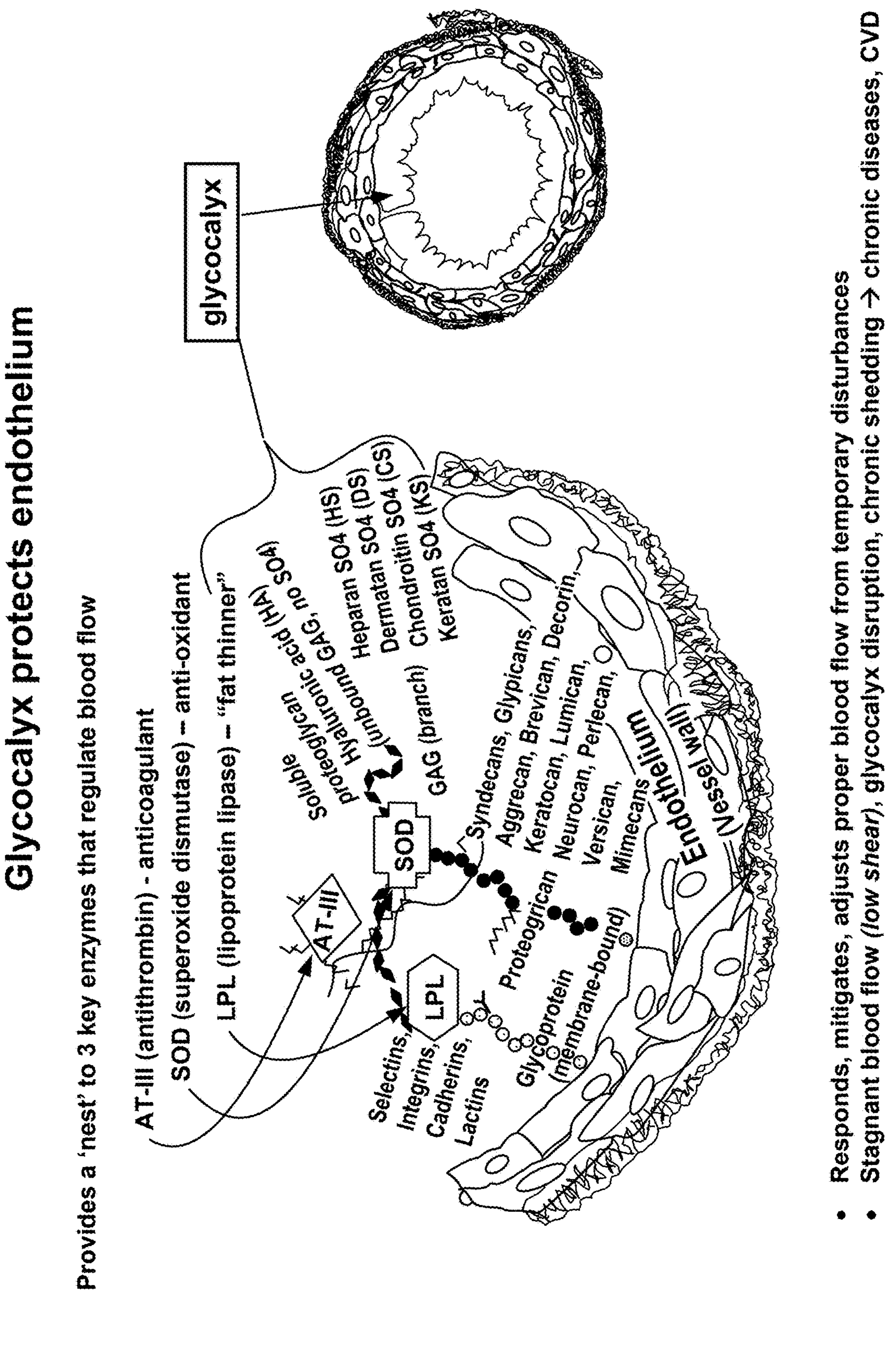
FIG. 11 is a depiction of three enzymes associated with the glycocalyx that regulate blood flow.
Figure 12A:
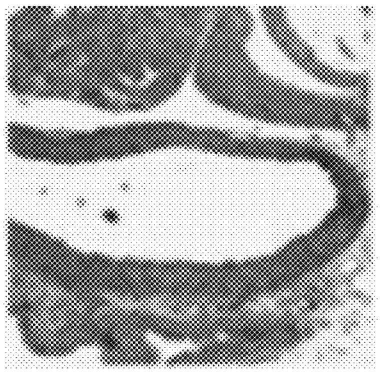
FIGS. 12A-12H are photographs of curative and preventive histopathology of arterial vessels in compound combinations designated B, F, I, and C (compounds in each combination are identified in FIG. 14): Preventative (A) and Curative (B) results for combination B ("Compound B"); Preventative (C) and Curative (D) results for combination F ("Compound F"); Preventative (E) and Curative (F) results for combination I ("Compound I"); and Preventative (G) and Curative (H) results for combination C ("Compound C").
Figure 12B:
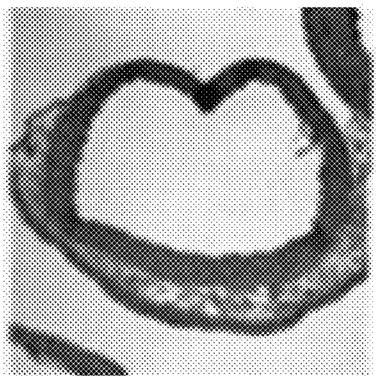
Figure 12C:
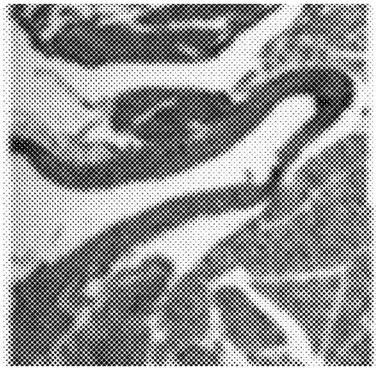
Figure 12D:
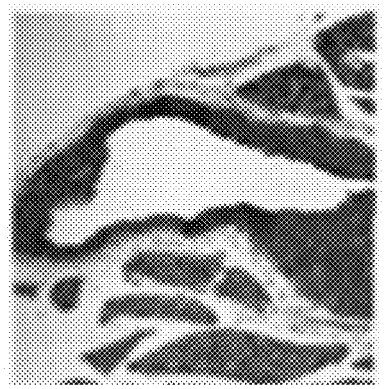
Figure 12E:
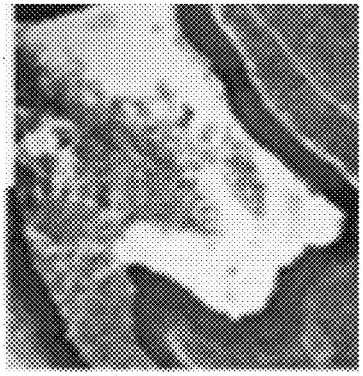
Figure 12F:
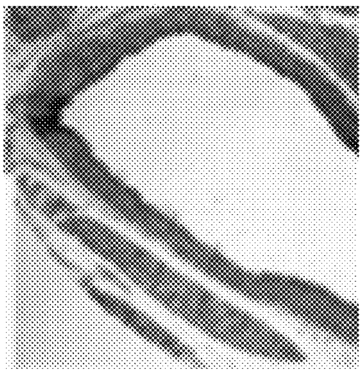
Figure 12G:
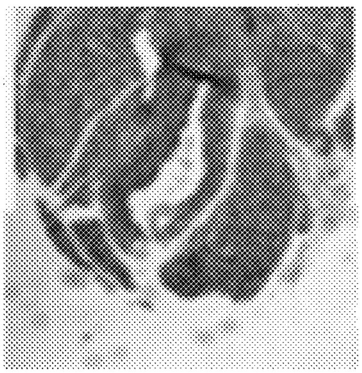
Figure 12H:
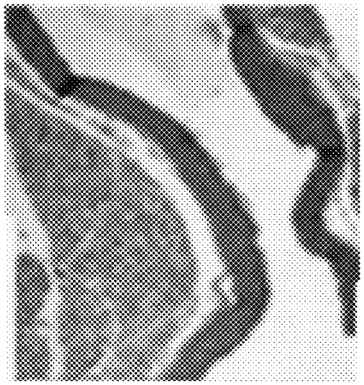

Any disruption or decrease in thickness of the glycocalyx can result in many different conditions, including chronic vascular disease (2010. Cardiovascular Research. Volume 87, Issue 2 pp. 300-310). For example, chronic stagnant blood flow, common in bifurcated sections of the arteries, triggers glycocalyx shedding and plaque formation. In the heart, disrupted glycocalyx in the coronaries result in poor blood flow (coronary perfusion); at the arteriolar level, a damaged glycocalyx slows down blood flow and decreases nitric oxide (NO) production, constricting vessels; and, at the capillary level, disrupted glycocalyx reduces blood flow to tissues or muscles. In addition, the glycocalyx harbors a wide array of enzymes that regulate proper blood flow including superoxide dismutase (SOD), an enzyme which neutralizes reactive oxygen species; antithrombin (AT-III), a natural anticoagulant (blood thinner); and, lipoprotein lipase (LPL), an enzyme that releases triglycerides from chylomicrons and very low-density lipoproteins (VLDL) for energy. See FIG. 11.

In case of cardiac ischemia/reperfusion injury (heart muscle damage due to blood flow obstruction, then re-establishment of blood supply), disrupted glycocalyx results in coronary constriction, poor blood flow, and edema. However, pre-treatment of the heart with antithrombin reduces glycocalyx shedding and restores coronary functions (2009. Cardiovascular Research. Volume 83, Issue 2Pp. 388-396).

Other more general consequences of a disrupted glycocalyx include osmotic gradient shifts, leakage between cells (such as vascular, kidney, and lung cells), macrophage infiltration and inflammation, and tissue dysfunction. Eventually, glycocalyx dysfunction can lead to blockage of flow in vasculature, the kidneys, the pancreas, and other organs and tissue.

Cardiovascular Disease

Cardiovascular disease (CVD) is the leading disease killer in the world and because of its complexity and manifested clinical sequelae, it continues to be the main subject in pathology research. Although members of the CVD family are totally different in clinical presentations, they are basically atherosclerosis-related and share a common feature, which is vascular damage, particularly to the endothelial glycocalyx. Once the vasculature is damaged, the thromboembolism cascade ensues. Thromboembolism as a process leading to the formation of thrombus (blood clot); once this thrombus dislodges from its origin, it forms an embolus, which flows downstream in the blood vessel tree as a thromboembolus and obstructs blood flow, which can be fatal.

The blood pressure generated by the pumping heart fluctuates and blood flow particularly slows down at arterial forks and bends, notably in the coronary arteries. A high-fat diet increases blood viscosity and further stagnates blood flow; this stagnation creates low shear and consequently shedding or disruption of the endothelial glycocalyx. Glycocalyx thickness range from 2 to 3 μm in small arteries to 4.5 μm in carotid arteries (2007. J Vasc Res 44:87-98), and shedding or damage to this layer decreases its function as a protective shield, leading to leakage of nutrients (extravasation) and tissue edema, loss of nutritional blood flow, and an increase in coagulability due to platelet and leucocyte clumping (adhesion).

The endothelial glycocalyx offers a "nest" for protective enzymes including anticoagulant anti-thrombin (AT-III), anti-oxidant (SOD), and anti-high blood viscosity lipoprotein lipase (LpL). Thus, the loss of endothelial glycocalyx results in a build-up of fibrin, a suppression of fibrinolysis, and the promotion of plaque formation. Further inflammation predisposes the plaque to rupture, and ruptured plaque triggers clots formation: this clot can be exacerbated by a seed clot formed by Roleaux cells and thus becoming a significant thrombus. Loose thrombi can wedge on a rigid vessel narrowed by plaque, particularly in individuals who already have atherosclerosis, causing a stroke (clogged artery to the brain), heart attack (clogged artery to the heart), or PAD (clogged artery to the arms or legs).

Thus, protection and/or restoration of the endothelial glycocalyx presents a promising therapeutic target both in an acute critical care setting and in the treatment of chronic vascular disease. Drugs that can specifically increase the synthesis of glycocalyx components, refurbish it, or selectively prevent its enzymatic degradation have not been widely available. (2010. Cardiovascular Research, Volume 87, Issue 2 pp. 300-310). However, compounds aimed at restoring and maintaining the glycocalyx have been described in U.S. Pat. No. 9,867,842 (issued Jan. 16, 2019 to Tunac), which is incorporated by reference herein for this description.

Under inflammatory conditions the integrity of the endothelial glycocalyx deteriorates to varying degrees particularly during generalized inflammatory responses, but glycocalyx can regain its original thickness after proper treatment of inflammatory condition (2008. Circulation Research, vol. 102, no. 7, pp. 770-776). Thus, therapeutic strategies can be directly aimed at preserving, supporting, or reconstituting the glycocalyx structure or strategies, either indirectly by down-regulating inflammatory processes or directly by inhibition of glycocalyx degradation with antioxidants (2006. American Journal of Physiology: Heart and Circulatory Physiology, vol. 290, no. 6, pp. H2247-H2256). An example of an anti-inflammatory drug is etanercept (Enbrel), which inhibits TNF-α, and reduces the shedding of glycocalyx constituents, coagulation activation, and functional vessel function in humans (2009. Atherosclerosis, vol. 202, no. 1, pp. 296-303).

Another approach to improving the condition of the glycocalyx is antithrombin therapy, since thrombin is known to cleave the syndecan component of glycocalyx (2009. Circulation Research, vol. 104, no. 11, pp. 1313-1317). Indeed, antithrombin therapy protects the glycocalyx from TNF-α and ischemia/reperfusion-induced shedding in hearts (2009. Basic Research in Cardiology, vol. 104, no. 1, pp. 78-89; 2010. Shock, vol. 34, no. 2, pp. 133-139), which can result in reduced post-ischemic leukocyte adhesion in hearts, reduced vascular permeability, reduced coronary leak, and reduced interstitial edema (2009. Basic Research in Cardiology, vol. 104, no. 1, pp. 78-89).

Biomarkers of Cardiovascular Disease

Biomarkers have been identified that can be useful for identifying individuals at risk of vascular diseases. For example, biomarkers of inflammation can indicate the presence of atherosclerosis or plaques (e.g., C-reactive protein, IL-18, IL-6). Biomarkers of lipid accumulation can indicate the presence of plaques (e.g., lipoprotein-associated phospholipase A2). Biomarkers of thrombosis can indicate the presence of plaque instability or carotid disease progression (e.g., tissue plasminogen activator (t-PA), fibrinogen, plasminogen activator inhibitor-1 (PAI-1)). However, no such biomarkers are currently in use by medical practitioners as a diagnostic tool.

U.S. Patent Application No. 2007/0269836 to McPherson, et al. discloses methods and compositions for diagnosis of venous thromboembolic disease, pulmonary embolism, and/or deep vein thrombosis, and for risk stratification in such conditions. An assay can be performed from test samples obtained from a subject to diagnose a subject, including markers used individually or in combination, such as thrombin-antithrombin complex (TAT), antithrombin III (ATIII), and PAI-1.

U.S. Pat. No. 8,759,095 to Vink, et al. discloses diagnostic and therapeutic tools for diseases altering vascular function. In particular, endothelial glycocalyx perturbation can be diagnosed in samples from subjects by detecting heparan sulfate (HS) (heparan sulphate therein), hyaluronidase (HAD), and syndecan-1.

U.S. Patent Application No. 2013/0273096 to Daniels discloses methods of treating disorders affecting the endothelial glycocalyx. Characteristics of the endothelial glycocalyx can be determined by detecting markers in a sample from a subject, such as heparan sulfate (HS), hyaluronidase (HAD), and syndecan-1.

Biomarkers Having Particular Utility in the Methods Described Herein

Biomarkers useful in the methods described herein include those described in PCT Pub. No. WO 2016/123163 (filed Jan. 27, 2016 by Tunac), as well as biomarkers that are newly described for this purpose. The biomarkers described herein can be used individually or in any combination, depending on the particular type of condition or disease to be detected. Illustrative combinations of biomarkes have been developed, as described below and in the Examples.

Biomarkers Described in PCT Pub. No. WO 2016/123163

In certain embodiments, the disclosure of U.S. patent application Ser. No. 16/060,840 is directed to "panels" of biomarkers used to detect a disease characterized by disruption of the glycocalyx, endothelial inflammation, and/or oxidative damage to the endothelium (e.g., vascular diseases), and especially biomarkers that indicate abnormal biochemical elements responsible for the blood clotting cascade and biomarkers that indicate abnormal levels of enzymes and structural components of the blood vessel surface (e.g., due to vascular oxidative damage; PCT Pub. No. WO 2016/123163 is incorporated by reference herein for this description).

Most generally, the biomarker panels include of a set of chemical, immunochemical and/or enzymatic assays or tests that can be used together for monitoring the levels of a set of biomarkers. The biomarker panels can be used to determine the presence of disease, or the propensity of an individual to develop disease. The biomarker panels can also be used to mark the progression of disease. Evaluation of different stages or components of vascular disease is important for intervention or reversal of the effects of the disease. For each of the biomarkers discussed herein, a baseline level for the biomarker is known or can be established that reflects the levels in a healthy individual. A healthy individual should have lower levels of the biomarker than an individual suffering from a disease characterized by disruption of the glycocalyx endothelial inflammation, and/or oxidative damage to the endothelium. If a biomarker level is above the baseline level in a sample from a subject, it can be determined that the subject has a disease characterized by disruption of the glycocalyx, endothelial inflammation, and/or oxidative damage to the endothelium (e.g., vascular disease) or is at risk of developing such a condition. Other levels can determine the stage or progression of the disease.

4-Marker Panel: Soluble Fibrin, Thrombin-Antithrombin Complex, Antithrombin III, and Plasminogen Activator Inhibitor In some embodiments, the biomarker panel can include a four-marker test for endothelial glycocalyx health that detects soluble fibrin (SF), thrombin-antithrombin complex (TAT), antithrombin III (ATIII), and plasminogen activator inhibitor (PAI-1). These markers are aimed at assessing clotting or clotting risk in a subject.

Soluble fibrin (SF) is composed of fibrin monomer and fibrinogen derivatives, existing in the circulating blood in patients with thrombosis. Its detection and quantification are useful for obtaining information about the condition and degree of intravascular coagulation in early-stage thrombosis. The level of SF increases on coagulation, which is related to the production of blood factor VIII. Thus, factor VIII circulates in the plasma bound to von Willebrand factor (vWf). Thrombin cleaves and activates factor VIII and releases vWf. The vWf is then free to bind to ruptured endothelial cell surfaces where it activates platelet aggregation. The released FVIIIa acts as a cofactor of factor IXa to generate factor Xa. In the presence of Ca2+ and phospholipids, FX is activated to FXa by FIXa. Since FVIIIa is a cofactor to FIXa, it greatly stimulates the reaction. A healthy individual should have lower levels of SF than a diseased individual. If levels are detected with the biomarker panel that are above the baseline level, it can be determined that the individual has vascular disease or is at risk of developing vascular disease and especially thrombosis. Other levels can determine the stage or progression of vascular disease.

Another blood component that reflects blood coagulation is the formation of thrombin-antithrombin complex (TAT). TAT complex is a parameter of coagulation and fibrinolysis. Elevated concentrations have been associated with vascular disease. Antithrombin deficiency promotes clot formation in the arteries and/or veins and is associated with a high risk of thromboembolic disorders. TAT can conveniently be detected using commercially available microtiter plates. These microtiter plates precoated with antibody specific to thrombin. Calibrators or samples are added to the appropriate microtiter plate wells with a biotin-conjugated polyclonal antibody preparation specific for ATIII. Next, avidin-conjugated to horseradish peroxidase (HRP) is added to each microplate well and incubated. Then, an HRP TMB substrate solution is added to each well. Only those wells that contain TAT, biotin-conjugated antibody and enzyme-conjugated avidin will exhibit a change in color. The enzyme-substrate reaction is terminated by the addition of a sulfuric acid solution, and the color change is measured spectrophotometrically at a wavelength of 450 nm±10 nm. The concentration of TAT in the samples is then determined by comparing the O.D. of the samples to the calibration curve.

Antithrombin III (AT III) is a non-vitamin K-dependent protease enzyme, which serves as a natural blood thinner and inhibits coagulation. AT III deficiency leads to increased risk of developing life-threatening clots that block blood flow. For example, deep vein thrombosis (DVT) occurs when a clot, or thrombus, develops in one of the deep veins, most common in the legs. The level of AT III is reduced when blood coagulates, which is determined by commercially available test kits. One such example of a test kit is the LS-F13067, which is a 96-well enzyme-linked immunosorbent assay (ELISA) for the quantitative detection of bovine antithrombin-III in samples of plasma and serum. It is based upon a sandwich assay principle and can be used to detect levels of Antithrombin-III as low as 78 picograms per milliliter. Another example is the AssayMax Mouse AT III ELISA kit (LSBio, Seattle WA 98121): this is designed for detection of mouse AT III in plasma, serum and cell culture supernatants. This assay employs a quantitative sandwich enzyme immunoassay technique, which measures AT III in 4 hours. Thus, a microtiter plate pre-coated with polyclonal antibody specific for mouse AT III is commercially available. Mouse AT III in standards and samples is sandwiched by the immobilized antibody and biotinylated polyclonal antibody specific for mouse AT III, which is recognized by a streptavidin-peroxidase conjugate. All unbound material is then washed away, and a peroxidase enzyme substrate is added. The color development is stopped and the intensity of the color is measured. A baseline level for AT III can be established that reflects the levels in a healthy individual. A healthy individual should have lower levels of AT III than a diseased individual. If levels are detected with the biomarker panel that are above the baseline level, it can be determined that the individual has vascular disease or is at risk of developing vascular disease. Other levels can determine the stage or progression of vascular disease.

Plasminogen activator inhibitor (PAI-1) is a protein, also known as endothelial plasminogen activator inhibitor or serpin E1, and is a central regulator of the blood fibrinolytic system and its production precedes thrombosis. In other words, increased PAI-1 levels increase the risk for thrombosis, whereas decreased levels cause recurrent bleeding. PAI-1 is the main inhibitor of the plasminogen activators and thus an important component of the coagulation system that down-regulates fibrinolysis. Reduced PAI-1 levels result in increased fibrinolysis and an associated bleeding diathesis.

The other PAI, plasminogen activator inhibitor-2 (PAI-2), is secreted by the placenta and only present in significant amounts during pregnancy. Test kits for PAI-1 are available commercially (a kit for human PAI-1 is commercially available from Sigma-Aldrich) in which free, latent or complex PAI-1 present in plasma reacts with the capture antibody coated and dried on a microtiter plate. Any unbound PAI-1 is washed away and an anti-PAI-1 primary antibody is added. Excess primary antibody is washed away and bound antibody, which is proportional to the total PAI-1 present in the samples, is then reacted with an HRP-labeled secondary antibody. Following an additional washing step, TMB is then used for color development at 450 nm. The amount of color development is directly proportional to the concentration of total PAI-1 in the sample.

3-Marker Panel: Syndecan-1, Heparan Sulfate, and Hyaluronidase

In some embodiments, the biomarker panel can include a three-marker test for endothelial glycocalyx health that detects syndecan-1 (SDC1), heparan sulfate (HS), and hyaluronidase (HAD). These markers are aimed at assessing glycocalyx integrity.

Syndecans are transmembrane domain proteins that carry three to five heparan sulfate and chondroitin sulfate chains, which harbor a variety of important ligands including fibroblast growth factors, vascular endothelial growth factor, transforming growth factor-beta, fibronectin, and antithrombin-1. Syndecan-1 (SDC1) is a cell-surface heparan sulfate proteoglycan, which is an important component of the protective endothelial glycocalyx lining the luminal surface of blood vessels. Key roles for SDC1 is in endothelial mechano-sensing and regulation of endothelial integrity and function. Shedding of syndecan-1 and heparan sulfate into the circulation is associated with inflammatory disease and atherosclerosis. Test kits for syndecan, for example, a test kit precoated with monoclonal antibody specific for SDC1, are available commercially. Samples are added to the appropriate microtiter plate wells with a biotin-conjugated polyclonal antibody preparation specific for SDC1. Next, avidin conjugated to HRP is added to each microplate well and incubated. Then a TMB substrate solution is added to each well. Only those wells that contain SDC1, biotin-conjugated antibody and enzyme-conjugated avidin will exhibit a change in color. The enzyme-substrate reaction is terminated by the addition of a sulphuric acid solution and the color change is measured spectrophotometrically at a wavelength of 450 nm±10 nm. The concentration of SDC1 in the samples is then determined by comparing the O.D. of the samples to the standard curve.

Heparan sulfates (HSs) are highly negatively charged polysaccharides with 1→4-linked sulfated glucosamine and uronic acid repeating disaccharide units. HSs are present on the cell surface as well as in the extracellular matrix and bind to proteins involved in anticoagulation, angiogenesis, microbial infection, and monocyte adhesion. HSs are glycoproteins with the common characteristic of containing one or more covalently attached chains, including syndecans and glycosylphosphatidylinositol-anchored proteoglycans (glypicans), the secreted extracellular matrix HSPGs (agrin, perlecan, type XVIII collagen), and the secretory vesicle proteoglycan, serglycin. HSs are implicated in the pathogenesis of atherosclerosis by their ability to trap plasma lipoproteins in the arterial wall and by their influence on cellular migration, adhesion and proliferation. Intact HS chains are anti-atherogenic. ELISA test kits for heparan sulfate are available commercially. The test includes pretreatment of serum with proteinase (actinase E) to digest serum proteins. One volume of dissolved actinase E (20 mg/mL in actinase E dissolution buffer) can be added against ten volumes of serum and then mixed. Proteins can be digested at 55° C. for 16-20 hours in a water bath. After digestion, the mixture can be boiled for 5 minutes to stop digestion. After boiling, the mixture can be brought to room temperature (15-25° C.) and then centrifuged 3,000 rpm, for 10 minutes. After centrifugation, the supernatant can be taken and mixed well. The supernatant can then be Heparan Sulfate ELISA kit. HS values can be calculated in pretreated samples according to the Heparan Sulfate ELISA kit procedure. The calculated HS values must be multiplied dilution factors as below to determine the HS concentration in serum. HS concentration=calculated HS value×dilution factor×1.1.

Hyaluronic acid (HA, also called hyaluronan or hyaluronate) is a negatively charged, nonsulfated large linear glycosaminoglycan (a class of negatively charged polysaccharides) of repeating disaccharide structure D-Glucuronic acid (UDP-GlcA) and N-acetylglucosamine (UDP-GlcNac), which is a principal component of endothelial glycocalyx. HA is distributed widely throughout connective, epithelial, and neural tissues. HA is the simplest glycosaminoglycan that provides compression strength, lubrication and hydration. A disturbed HA is atherogenic. The removal of HA-rich glycocalyx with hyaluronidase is associated with increased vascular permeability leading to atherogenic insults. Increased plasma HA and hyaluronidase (HAD) levels are found associated with endothelial glycocalyx damage, presence of microvascular diseases and carotid intima-media thickness. In an illustrative assay, coated-well immunoenzymatic assay for the quantitative measurement of hyaluronidase (HAD) utilizes a polyclonal anti-HAD antibody and an HAD-HRP conjugate. The assay sample and buffer are incubated together with HAD-HRP conjugate in pre-coated plate for one hour. After the incubation period, the wells are decanted and washed five times. The wells are then incubated with a substrate for HRP enzyme. The product of the enzyme-substrate reaction forms a blue colored complex. Finally, a stop solution is added to stop the reaction, which will then turn the solution yellow. The intensity of color is measured spectrophotometrically at 450 nm in a microplate reader. The intensity of the color is inversely proportional to the HAD concentration since HAD from samples and HAD-HRP conjugate compete for the anti-HAD antibody binding site. Since the number of sites is limited, as more sites are occupied by HAD from the sample, fewer sites are left to bind HAD-HRP conjugate. Standards of known HAD concentrations are run concurrently with the samples being assayed and a standard curve is plotted relating the intensity of the color (O.D.) to the concentration of HAD. The HAD concentration in each sample is interpolated from this standard curve.

3-4-Marker Panels: Hyaluronan Synthase-1, Heparan Sulfate, Plasminogen Activator Inhibitor, and Optionally Syndecan-1

The biomarker panel can also include any combination of the above-described biomarkers, i.e. they are not limited to being used in combination in just the three-marker test and four-pan test. For example, another preferred combination can include a panel of hyaluronan synthase-1 (HAS-1), heparan sulfate (HS), and plasminogen activator inhibitor (PAI-1) as a blood test that defines vascular leakage and clot onset to correlate with plaque formation. As shown in the examples below, these three biomarkers are highly correlative with plaque formation. In certain embodiments, syndecan-1 (SDC-1) is added to these biomarkers to produce a 4-marker panel.

Additional Biomarkers

In addition to the above, three other biomarkers associated with cell disruption are useful in the methods described herein and, in some embodiments, can be combined with any of the biomarkers and panels described above to complement the diagnosis of a wider range of chronic diseases: gamma (γ') fibrinogen (GF), growth differentiation factor-15) (GDF-15), and pregnancy associated plasma protein-A (PAPP-A).

Gamma Fibrinogen

Plasma fibrinogen is a coagulation factor and an acute-phase inflammatory marker that has been implicated in the pathophysiology of cardiovascular disease (CVD) (2005. JAMA. 294:1799-1809). Fibrinogen is a key component of the hemostatic system, playing a role in both primary and secondary response. Fibrinogen is composed of three pairs of non-identical polypeptide chains. "Gamma (γ')" fibrinogen (GF) refers to the gamma chain. Thrombin-catalyzed cleavage of fibrinopeptides (Fp) A and B converts fibrinogen into fibrin, which spontaneously polymerizes and forms double-stranded protofibrils that assemble into branched fibrin fibers, forming the fibrin clot (2008. Cardiovasc Hematol Agents Med Chem 6:181-189). GF is a biomarker for early clotting. GF was demonstrated to be significantly associated with coronary artery disease and myocardial infarction in the Stockholm Coronary Artery Risk Factor Study and the Framingham Heart Study. (2007.J Thromb Haemost 5:766-73) and is significantly associated with stroke, as seen in the Erasmus Stroke Study and others (2012. Thrombosis Research 129:807-809). GF increases during inflammation and is differentially regulated from total fibrinogen under pathologic conditions, as demonstrated in the Periodontitis and Vascular Events Study (2011. Thromb Haemost 105:605-9).

Elevated Human Levels of GF have been Reported in a Variety of Studies:

Study of 133 patients diagnosed with coronary artery disease (CAD): diseased, 0.413 g/L versus 0.299 g/L in the controls (1996. J Biol Chem 271(38):23121-23125.

Epidemiologic study on myocardial infarction (MI) in the Stockholm Coronary Artery Risk Factor cohort: diseased 0.28 g/L higher than controls (2007. J Thromb Haemost 5:766-73).

Study of patients with a history of CVD and periodontal disease: highly elevated compared to controls, 0.622 g/L (2010 Clin Chem 2010; 56:781-8).

Study validating GF as an independent predictor of CAD: hypertensive participants 433.36 versus 405.70 mg/dL in controls (2017.Rev Esp Cardiol. 70:34-41).

Study showing GF is positively associated with deaths due to peripheral artery disease (PAD), heart failure (HF), and CVD deaths: lowest quartile 8.0-24.34 mg/dl; highest quartile ≥35.19 mg/dl (2015. Arterioscler Thromb Vasc Biol. 35(12): 2700-2706).

Study on 3,042 participants of the Framingham Heart Study Offspring Cohort: individuals with prevalent CVD, 0.278 mg/ml vs. 0.258 mg/ml without (2011. Arterioscler Thromb Vasc Biol. October; 31(10): 2345-2352).

Physicians Health Study of 14,916 subjects: levels of 343 mg/dL, twofold increase in the risk of a myocardial infarction (2013. University Heart Journal 9:40-46).

Study reporting GF is significantly higher in patients with ischemic stroke, 0.37 g/L versus 0.32 g/L in controls (2011.Thromb Haemost, 105:430-4).

Growth Differentiation Factor-15

Growth differentiation factor-15 (GDF-15) is a protein belonging to the transforming growth factor beta superfamily, which functions in regulating inflammatory pathways, apoptosis, and cell repair and cell growth associated in cardiovascular and neoplastic disorders (2000. Molecular and Cellular Biology. 20 (10): 3742-51). GDF-15 serves as a prognostic protein in patients with different diseases such as heart diseases and cancer, expressed in low concentrations in most organs and upregulated because of injury of organs such as such as liver, kidney, heart and lung (2005. Shock. 23 (6): 543-8). GDF-15 is a stress-responsive cytokine, which increases during tissue injury and inflammatory states and is associated with cardiometabolic risk. Increased GDF-15 levels are associated with cardiovascular diseases such as hypertrophy, heart failure, atherosclerosis, endothelial dysfunction, obesity, insulin resistance, diabetes, and chronic kidney diseases in diabetes. GDF-15 is an inflammatory marker associated with increased cardiovascular and noncardiovascular mortality and plays pivotal role in development and progression of cardiovascular diseases, such as heart failure, coronary artery diseases, atrial fibrillation, diabetes, cancer, and cognitive impairment (2013. Clinical Chemistry 59:1550-1552 2014. Circulation 130:1847-1858). Increased GDF-15 level is linked with the progression and prognosis of the disease condition.

Elevated Human Levels of GDF-15 have been Reported in a Variety of Studies:

- One study stratified the blood GDF-15 levels into three categories, that is, normal (<1200 μg/mL), moderately elevated (1200-1800 μg/mL), and highly elevated (>1800 μg/mL). (2010. Aging Cell, 9:1057-1064).
- Elevated levels of GDF-15 of >1800 ng/L have been reported to be associated with high risk for mortality within one year (2008.BMC Public Health, 8:148).
- Another studied showed that GDF-15 concentrations ≥1800 ng/L correlated with increased risk for all-cause and cardiovascular death compared to those with <1200 ng/L. (2012. Clinical Chemistry 58:172-182).
- Elevated GDF-15 levels been reported to be associated with reduced endothelium-dependent vasodilation in resistance vessels from <948 ng/L (1st quartile)–>1390 ng/L 4th quartile) (2009. Eur Heart J. 30:2346-2353).
- Another study found, given a median concentration of 1253 ng/L at baseline: hazard ratio (HR) for the highest compared to the lowest quartile for CV death, 2.63; for sudden death, 3.06; for heart failure (HF) death, 4.3; for cancer death, 2.5; for hospitalization for HF, 5.8 (3.2-10) for MI 1.4; and 1.8 for stroke (2017.Clinical Chemistry 63:1 140-151) (2017).

Pregnancy Associated Plasma Protein-A

Pregnancy-associated plasma protein-A (PAPP-A) level is an independent predictor of acute cardiovascular event occurrence. PAPP-A is associated with thin-cap plaque leakage and a higher burden of coronary thin-cap fibroatheroma (TCFA). PAPPP-A is elevated in patients with acute coronary syndromes and patients with risk factors, such as obesity, hypertension, and/or diabetes, relative to healthy subjects (2015. Biomark Med. 9:731-741). PAPP-A is highly expressed in vulnerable atheromatous plaques (2016. Medicine (Baltimore) 95:e2563; 2004. Circulation 109:1724-1728; 2005. Clin Chem 52:1096-1103).

Elevated Human Levels of PAPP-A have been Reported in a Variety of Studies:

PAPP-A level is an independent predictor of acute cardiovascular event occurrence, associated with thin cap plaque leakage and a higher burden of coronary thin-cap fibroatheroma (TCFA); it is elevated in patients with acute coronary syndromes and patients with risk factors, such as obesity, hypertension, and/or diabetes relative to healthy subjects (2015. Biomark Med. 9:731-741); also, it is highly expressed in vulnerable atheromatous plaques (2016. Medicine (Baltimore) 95: e2563). Patients with ≥3 VH (virtual histology)-TCFAs have been reported to have a higher PAPP-A level than patients with 1 to 3 VH-TCFAs or without any VH-TCFA (13.3±11.8 versus 7.8±4.7 versus 7.4±4.7 mIU/L, P<0.001, respectively). (2016. Medicine (Baltimore).95 (3): e2563).

PAPP-A levels in Acute Coronary Syndrome: PAPP-A levels have been reported to be significantly elevated in patients with acute myocardial infarction (AMI) and in patients with unstable angina (UA), with mean levels of 64.26 and 36.23 ng/ml respectively, whereas mean PAPP-A levels in controls were 10.68±1.04 ng/ml. (2015. Indian J Clin Biochem. 30(2): 150-154).

PAPP-A reportedly correlates with cardiovascular events in diabetic hemodialysis patients, with a median PAPP-A concentration of 17 mIU/patients in the 4th PAPP-A quartile (≤20.9 mIU/L) had an adjusted 2.6-fold increased risk of sudden death and 2.8-fold increased risk of stroke as compared to the patients in the 1st quartile (≤13:4 mIU/L) (2014. Atherosclerosis.236:263-269).

3-Marker Panel: Gamma Fibrinogen, Growth Differentiation Factor-15, And Pregnancy-Associated Plasma Protein-A In some embodiments, a biomarker panel useful in any of the methods described herein includes gamma fibrinogen (GF), growth differentiation factor-15 (GDF-15), and pregnancy-associated plasma protein-A (PAPP-A).

7-Marker Panel: Hyaluronan Synthase-1, Heparan Sulfate, Plasminogen Activator Inhibitor, Syndecan-1, Gamma Fibrinogen, Growth Differentiation Factor-15, and Pregnancy-Associated Plasma Protein-A In certain embodiments, a biomarker panel useful in any of the methods described herein includes hyaluronan synthase-1 (HAS-1), heparan sulfate (HS), plasminogen activator inhibitor (PAI-1), syndecan-1 (SDC-1), gamma fibrinogen (GF), growth differentiation factor-15 (GDF-15), and pregnancy-associated plasma protein-A (PAPP-A).

This 7-biomarker combination is useful in determining a biomarker signature that indicates a disease type and/or a stage of disease. Accordingly, the 7-marker combination can be used in making a differential diagnosis between at least two diseases and/or two stages of disease, allowing treatment to targeted to the particular disease and/or disease stage.

This 7-biomarker combination is also useful in associating a disease signature with a particular disease. For example, the panel can be used to detect the levels of the seven biomarkers in various diseases or disease stages and this raw data analyzed to define a disease signature for a given disease or disease stage. For a particular disease, it may be determined that a combination of two, three, four, five or six biomarkers provides a reliable biomarker signature of the disease or disease stage and/or allows discrimination between two or more possible diseases or disease stages, facilitating a differential diagnosis, and thereby facilitating treatment aimed at the particular disease or disease stage identified in a subject. The 7-biomarker panel can thus be used to determine that only a subset of these markers is needed to identify or discriminate a given disease and/or disease stage from another. In this way, the 7-biomarker panel can be used in research aimed at identifying useful biomarker panels made up of subsets of the seven biomarkers.

Biomarker Panels and Uses Thereof

In General

The biomarker panels described herein can be used alone or in combination. For example, the biomarker panels can be used individually if there is a strong correlation established for any of the biomarkers in that particular panel, or the combination of biomarker panels can be used to ensure reliability.

The biomarker panels can be used to detect the presence of a disease characterized by disruption of the glycocalyx, endothelial inflammation, and/or oxidative damage to the endothelium (e.g., vascular disease) or propensity to develop such a condition in the following method. In an illustrative embodiment, a sample is taken, or caused to be taken (preferably by a healthcare practitioner), from a subject and tested using the biomarker panel (either the four-panel test for clotting, the three-panel test for glycocalyx integrity, both as described above, or any combination of the above-described biomarkers). If any or all of the biomarkers are detected, it can be determined if the subject has, or is at risk for, a disease characterized by disruption of the glycocalyx, endothelial inflammation, and/or oxidative damage to the endothelium (e.g., vascular disease) by comparing the biomarker levels to known baseline levels for healthy individuals. In other words, if levels of two biomarkers are detected that are above the baseline level, it can be determined that the individual has, or is at risk for, a disease characterized by disruption of the glycocalyx, endothelial inflammation, and/or oxidative damage to the endothelium (e.g., vascular disease).

In some embodiments, the biomarker panel can be used to determine the stage of a disease characterized by disruption of the glycocalyx, endothelial inflammation, and/or oxidative damage to the endothelium (e.g., vascular disease) in an individual (e.g., to monitor the progression of vascular disease in the individual). The stage of a disease characterized by disruption of the glycocalyx, endothelial inflammation, and/or oxidative damage to the endothelium (e.g., vascular disease) can be determined by comparing the results to known stage levels. Based on the results of the stage of vascular disease, the individual can be proscribed medication that is appropriate for that particular stage.

In some embodiments, the biomarker panel can be used to determine a prognosis for a disease characterized by disruption of the glycocalyx, endothelial inflammation, and/or oxidative damage to the endothelium (e.g., vascular disease) in an individual. A negative prognosis, for example, enables a physician and patient to select a more aggressive form of treatment than would normally be used at that point in diagnosis and treatment.

In certain embodiments, the biomarker panel can also be used in a method of monitoring the efficacy of a drug or other therapy against a disease characterized by disruption of the glycocalyx, endothelial inflammation, and/or oxidative damage to the endothelium (e.g., cardiovascular diseases or other diseases involving inflammation, disruption of blood vessels, plaques, or clots). Such monitoring can be carried out during drug development (e.g., in an animal model such as that described herein or in human subjects) or during the treatment of actual patients. Illustrative treatments that can be monitored include, but are not limited to, anti-inflammatories (such as non-steroidal anti-inflammatory drugs (NSAIDS), steroids, or immune selective anti-inflammatory derivatives (ImSAIDs)), anticoagulants (such as alteplase, ardeparin, dalteparin, danaparoid, enoxaparin, fondaparinux, lepirudin, urokinase, or warfarin), antioxidants (such as glutathione, alpha-lipoic acid, CoQ10, resveratrol, carotenoids, astaxanthin Vitamin C, or Vitamin E), supplements, and any other suitable therapeutics.

In some embodiments, the biomarkers included in the panels of the present disclosure measure factors produced early on in the clot formation process. Therefore, each of these biomarkers are useful alone, as well as together in the panels, in predicting the initiation of the biologic processes (e.g., oxidation and immunogenic and/or inflammatory processes) that leads to the formation of the clots. The biomarker panels described herein may be useful in conjunction with that "lipid panel" devised by the American Heart Association (measuring cholesterol and triglyceride), but since the lipid panel is not reliable predictive of cardiovascular disease, it is contemplated that one or more of the biomarker panels of the present disclosure can replace this lipid panel for routine diagnostics.

As those of skill in the art will readily appreciate, the absolute levels of biomarkers can vary, depending on the biological sample tested (e.g., blood or a blood fraction) and on the particular assay used (since assays will vary with regard to sensitivity and dynamic range). It is within the level of skill in the art to select or design assays suitable for discriminating between a healthy individual and one suffering from a disease characterized by disruption of the glycocalyx, inflammation, and/or oxidative damage.

Sample Collection and Processing

The assay methods described herein are generally carried out on biological samples derived from an animal, in some embodiments a mammal, and in certain embodiments a human.

The methods described herein can be carried out using any sample relevant to the particular glycocalyx at issue (e.g., a blood or blood fraction, for atherosclerosis). Illustrative samples include, for example, blood, plasma, urine, saliva, tears, and cerebral spinal fluid, or a fraction of any of these (e.g., a liquid or tissue fraction, cell, or protein).

The sample may be pretreated as necessary by dilution in an appropriate buffer solution or concentrated, if desired. Any of a number of standard aqueous buffer solutions and/or protease inhibitors, employing any of a variety of buffers, such as phosphate, Tris, or the like, at physiological pH, can be used.

Assaying Biomarkers

The biomarkers described herein can be detected and quantified by any of a number of methods well known to those of skill in the art. These may include analytic biochemical methods such as electrophoresis, capillary electrophoresis, electrochemiluminescence, high performance liquid chromatography (HPLC), thin layer chromatography (TLC), hyperdiffusion chromatography, mass spectroscopy and the like, or various immunological methods such as, but not limited to, Western blot, immunoprecipitation, immunohistochemistry, enzyme-linked immunosorbent assay (ELISA), radioimmunassay (RIA), radioreceptor assay, proteomics methods (such as mass spectrometry), or quantitative immunostaining methods.

The sample reacts with various reagents in the panel based on the presence of the biomarkers described above. In some embodiments, the sample to be applied to the panel is sent to a lab for analysis. Any method of detection and quantification can be used. In some embodiments, the panel contains one or more reagents (such as antibodies) conjugated to a detectable label. Those of skill in the art can readily determine a suitable detection and quantification method for a given detectable label. For example, the assays described herein can provide a colorimetric result and can be read in a colorimeter.

In certain embodiments, biomarkers are detected and/or quantified in the biological sample using any of a number of well-known immunoassays (see, e.g., U.S. Pat. Nos. 4,366,241; 4,376,110; 4,517,288; and 4,837,168). For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

Conventional immunoassays often utilize a "capture agent" to specifically bind to and often immobilize the analyte on a solid phase. In preferred embodiments, the capture agent is an antibody.

Immunoassays also typically utilize a labeled detection agent to specifically bind to and label the binding complex formed by the capture agent and the analyte. The labeled detection agent may itself be one of the moieties making up the antibody/analyte complex. Alternatively, the labeled detection agent may be a third moiety, such as another antibody, that specifically binds to the capture agent/analyte complex. Other polypeptides capable of specifically binding immunoglobulin constant regions, such as polypeptide A or polypeptide G may also make up the labeled detection agent. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111:1401-1406, and Akerstrom (1985) J. Immunol., 135:2589-2542).

Immunoassays for detecting the target biomarker(s) can be either competitive or noncompetitive. Noncompetitive immunoassays are assays in which the amount of captured analyte is directly measured. In competitive assays, the amount of analyte in the sample is measured indirectly by measuring the amount of an added (exogenous) labeled analyte displaced (or competed away) from a capture agent by the analyte present in the sample. In one competitive assay, a known amount of labeled biomarker is added to the sample, and the sample is then contacted with a capture agent. The amount of labeled biomarker bound to the antibody is inversely proportional to the concentration of the biomarker present in the sample.

Biomarkers can also be measured by any available proteomics method, such as mass spectroscopy (MS), which measures the mass-to-charge ratio (m/z) of gas-phase ions. Mass spectrometers consist of an ion source that converts analyte molecules into gas-phase: ions, a mass analyzer that separates ionized analytes based on m/z ratio, and a detector that records the number of ions at each m/z value. MS is particularly suitable for the analysis of GAGs to accurately determine oligosaccharide molecular weights and their distributions within a mixture. Two approaches for MS proteomics are whole-protein analysis ("top-down") and analysis of enzymatically or chemically produced peptides ("bottom-up"). Either or both can be used to measure any of the biomarkers described herein.

Antibodies

Antibodies useful in the immunoassay methods described herein include polyclonal and monoclonal antibodies. Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies see, for example, Coligan, et al. (1991) Unit 9, Current Protocols in Immunology, Wiley Interscience.

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348:552-554; Hoogenboom et al. (1991) Nucleic Acids Res. 19:4133-4137).

Since the antibody fragments on the surface of the phage are functional, phage-bearing antigen-binding antibody fragments can be separated from non-binding phage by antigen affinity chromatography (McCafferty et al. (1990) Nature, 348:552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348:552-554). Thus, even when enrichments are low (Marks et al. (1991) J. Mol. Biol. 222:581-597), multiple rounds of affinity selection can lead to the isolation of rare phage. Since selection of the phage antibody library on antigen results in enrichment, the majority of clones bind antigen after as few as three to four rounds of selection. Thus, only a relatively small number of clones (several hundred) needs to be analyzed for binding to antigen.

As those of skill in the art readily appreciate, antibodies can be prepared by any of a number of commercial services (e.g., Berkeley antibody laboratories, Bethyl Laboratories, Anawa, Eurogenetec, etc.).

Solid Phase

For embodiments of the biomarker assay that employ a solid phase as a support for the capture agent, the solid phase can be any suitable porous material with sufficient porosity to allow access by reagents and a suitable surface affinity to bind a capture agent. Microporous structures are generally preferred, but materials with gel structure in the hydrated state may be used as well. Useful solid supports include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto, bonded, or laminated to appropriate inert carriers, such as paper, glass, plastic films, fabrics, or the like.

The porous structure of nitrocellulose has excellent absorption and adsorption qualities for a wide variety of reagents including monoclonal antibodies. Nylon also possesses similar characteristics and also is suitable.

Porous solid phases useful in the assays described herein can be in the form of sheets of thickness from about 0.01 to 0.5 mm, e.g., about 0.1 mm. The pore size may vary within wide limits and is preferably from about 0.025 to about 15 microns, especially from about 0.15 to about 15 microns.

Preferred solid phase materials for flow-through assay devices include filter paper such as a porous fiberglass material or other fiber matrix materials. The thickness of such material is not critical and will be a matter of choice, largely based upon the properties of the sample or analyte being assayed, such as the fluidity of the biological sample.

Alternatively, the solid phase can constitute microparticles. Microparticles useful in the assays described herein can be selected by one skilled in the art from any suitable type of particulate material and include those composed of polystyrene, polymethylacrylate, polypropylene, latex, polytetrafluoroethylene, polyacrylonitrile, polycarbonate, or similar materials.

Microparticles can be suspended in the mixture of soluble reagents and biological sample or can be retained and immobilized by a support material. In the latter case, the microparticles on or in the support material are not capable of substantial movement to positions elsewhere within the support material.

The methods of the present disclosure can be adapted for use in systems that utilize microparticle technology including automated and semi-automated systems wherein the solid phase comprises a microparticle. Such systems include those described in pending U.S. App. No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. Capture agent(s) can be affixed, directly or indirectly, to the electrode(s). In one embodiment, for example, capture agents can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). The basic method is described further below with respect to electrochemical detection.

The capture agent can be attached to the solid phase by adsorption on the porous material, where it is retained by hydrophobic forces. Alternatively, the surface of the solid phase can be activated by chemical processes that cause covalent linkage of the capture agent to the support.

To change or enhance the intrinsic charge of the solid phase, a charged substance can be coated directly onto the solid phase material or onto microparticles which then are retained by a solid phase material. Ion capture procedures for immobilizing an immobilizable reaction complex with a negatively charged polymer, described in U.S. App. No. 150,278, corresponding to EP Publication No. 0326100, and U.S. App. No. 375,029 (EP Publication No. 0406473), can be employed to affect a fast solution-phase immunochemical reaction. In these procedures, an immobilizable immune complex is separated from the rest of the reaction mixture by ionic interactions between the negatively charged polyanion/immune complex and the previously treated, positively charged porous matrix and detected by using any of a number of signal-generating systems, including, e.g., chemiluminescent systems, as described in U.S. App. No. 921,979, corresponding to EPO Publication No. 0 273,115.

If the solid phase is silicon or glass, the surface must generally be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis (succinimidyl) suberate, SPPD 9 succinimidyl 3-[2-pyridyldithio] propionate), SMCC (succinimidyl-4-[Nmaleimidomethyl] cyclohexane-1-carboxylate), SIAB (succinimidyl [4iodoacetyl]aminobenzoate), and SMPB (succinimidyl 4-[1 maleimidophenyl] butyrate) to separate the capture agent from the surface. Vinyl groups can be oxidized to provide a means for covalent attachment. Vinyl groups can also be used as an anchor for the polymerization of various polymers such as poly-acrylic acid, which can provide multiple attachment points for specific capture agents. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific capture agent on a solid phase using techniques and chemistries described U.S. App. No. 150,278, filed Jan. 29, 1988, and U.S. App. No. 375,029, filed Jul. 7, 1989, each of which is incorporated herein by reference.

Other considerations affecting the choice of solid phase include the ability to minimize non-specific binding of labeled entities and compatibility with the labeling system employed. For, example, solid phases used with fluorescent labels should have sufficiently low background fluorescence to allow signal detection.

Following attachment of a specific capture agent, the surface of the solid support may be further treated with materials such as serum, proteins, or other blocking agents to minimize non-specific binding.

Labeling Systems

As discussed above, many immunoassays employ a labeled detection agent.

The label can be attached to the detection agent prior to, or during, or after contact with the biological sample. So-called "direct labels" are detectable labels that are directly attached to or incorporated into detection agents prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. Such polypeptides can thus be labeled and added to the assay mixture, where they will bind to the detection antibody.

Some labels useful in the assays described herein may require the use of an indicator reagent to produce a detectable signal. In an ELISA, for example, an enzyme label (e.g., beta-galactosidase) will require the addition of a substrate (e.g., X-gal) to produce a detectable signal.

In some embodiments, the biomarker panel can use a support structure such as a flat microwell plate (such as an ELISA plate) that has multiple wells to hold samples. Various enzymes or antibodies can be applied to the wells as needed for each test, such as those described above. A housing can enclose the biomarker panel to prevent contamination or unwanted spread of samples, and it can be formed from plastic or another suitable material.

Kits

The biomarker panels described herein can be included in a kit. Kits include one or more reagents useful for practicing one or more assays described herein. The kit can include the biomarker panels (the four-panel or three-panels or any combination of the above-described biomarkers), instructions for use, materials to take and apply samples to the panel (such as, but not limited to, swabs, syringes, or vials), and descriptions of biomarker levels and their meaning (such as normal values). The kit can include various antibodies as needed to detect the biomarkers.

In some embodiments, a kit includes a package with one or more containers holding the reagents, as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits useful in the assays described herein preferably include instructions for carrying out one or more of the assays. Instructions included in kits of the invention can be affixed to packaging material or can be included as a package insert. While the instructions are typically written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term “instructions” can include the address of an internet site that provides the instructions.

Using Biomarker Signatures in Differential Diagnosis and Treatment

The biomarkers described herein have been found to have different absolute and/or relative levels that correlate with different disease types. FIG. 13 demonstrates that the 7-biomarker panel described above provides different biomarker signatures or “fingerprints” for each of three types of cardiovascular disease, namely coronary heart disease (CHD), hypertension (HTN), and heart failure (HF). The levels of the blood markers were obtained from published clinical data; individual markers were associated to some degree with any of the three diseases, but as a panel, become more specific and precise.

Biomarker signatures can be composed of individual biomarker levels and/or parameters derived therefrom (e.g., the ratio of one biomarker level to that of another). Biomarker signatures can be derived from the use of an algorithm, pattern recognition, dot matrix, and the like.

Arterial Plaque Animal Model

The knockout ApoE mice (apoE*3-Leiden, apoE−/−) are the standard model for atherosclerosis but do not represent clinical settings: (1) there are no studies yet showing plaques in this modal that become disrupted spontaneously (2005. Circ Res. 96:667-674); and (2) fatal human plaques are fibrous lesions without necrotic cores (1996. Circulation. 93:1354-1363), but no appropriate animal model of this had been available (2001. J Pathol. 195:257-263; 2001.Arterioscler Thromb Vasc Biol.21: 1470-1476).

Incidental rat models have been used to assess glycocalyx disruption (shedding of syndecan-1 and heparan sulfate) in hyperglycemia (2011.Anesth Analg. 112(6): 1289-1295), haemorrhagic shock (2013. J Trauma Acute Care Surg. 75(5): 759-66), inflammation and ischaemia-reperfusion injury (2004. Am J Physiol Heart Circ Physiol. 286(5): H1672-80), and coagulation function after hemorrhagic shock (2013.J Trauma Acute Care Surg. 75(5): 759-66). But there has been no animal model that represents glycocalyx disruption in relation to cardiovascular disease (CVD).

To develop the biomarkers described herein evaluate the FTX drug leads discussed above, we developed the first mouse model that mimics CVD and the thromboembolic cascade, called the Tunac Arterial Plaque (TAP) Mouse™ model, (2017. J Clin Exp Cardiolog Suppl 8:1). To generate this model, mice are fed a high-fat diet and administered a xenobiotic and a pathogen. This process is illustrated in Example 1, in which mice fed a diet that was 60% fat (by weight) and treated with the bacterium *Porphyromonas gingivalis* and a polychlorinated biphenyl resulted in a mouse that produced well-formed subendothelial plaques (FIGS. 10A-10C).

In various embodiments, the animal can be any of the typical experimental animals (e.g., mammals, such as mice, rats, dogs, cats, non-human primates).

In some embodiments, the high-fat diet is at least 21%, 30%, 35%, 40%, 45%, 50%, 55%, 60%, 65% or 70% fat by weight. In various embodiments, the percentage of fat in the diet falls within a range bounded by any of these values, e.g., 30%-70%, 35%-69%, 40%-68%, 45%-67%, 50%-65%, 55%-65% fat by weight.

The xenobiotic used is typically one that contributes to disruption of the glycocalyx, endothelial inflammation, oxidative damage to the endothelium, or any combination thereof. Illustrative xenobiotics include, but are not limited to, polychlorinated biphenyls, heavy metals (e.g., lead, arsenic, cadmium, mercury, nickel), phytoestrogens (e.g., resveratrol, caffeine), dioxins (e.g., chlorinated wastes), phthalates (e.g., plasticizers), fire retardants (e.g., halocarbons), phenols, polyaromatic hydrocarbons, pesticides/insecticides/herbicides, microorganisms, drugs (e.g, those containing aromatic sulphonic acids, alkyl benzene sulphonates, polychlorination, and diazo bonds), smoke, and other particulate matter, and the like. Without being limited to any particular mechanism of action, it is believed that most xenobiotics act, in this context, to disrupt electronic bonding of molecules, e.g, stealing electrons. Thus, the molecule that loses an electron is oxidized, and an oxidized molecule can become antigenic and/or elicit inflammation and inflammatory cytokines.

The pathogen can be any pathogen capable of infecting the animal used for the model. Examples of pathogens that can be used with typical experimental animals (e.g., mammals, such as mice, rats, dogs, cats, non-human primates) include, but are not limited to, gut microbes (*Chlamydia* sp., *H. pylori, Enterobacter* sp., Cytomegalovirus); dental microbes (*Porphyromonas gingivalis, Prevotella* sp., *Tannerella* sp., *Aggregatibacter* sp.), and the like.

The treatment regimen may vary, depending on the particular high-fat diet, xenobiotic, and pathogen used, and a suitable regimen for a particular case can be determined by those of skill in the art in light of the guidance provided herein (see, e.g., Example 1).

Glycocalyx-Restoring and -Maintaining Compositions

The present disclosure provides for a composition for treating multiple disease characterized by disruption of the glycocalyx. This composition includes at least one glycocalyx-restoring and -maintaining compound. The composition preferably treats disruption of the glycocalyx, inflammation, and oxidative damage. The composition can also treat any one of these issues individually. The glycocalyx-restoring and -maintaining compound can be any suitable compound that is able to perform one or more of these functions in the body.

For example, the glycocalyx-restoring and -maintaining compound can be a peptide and homolog of the glycopeptides in the glycocalyx that acts to stimulate glycoprotein synthesis. During glycoprotein synthesis, the peptide portion of the molecule is synthesized first, then the sugar moieties are incorporated. Attachment of the peptide portion to the surface appears to be by association between a region of repeated amino acids and components of the glycocalyx.

In some embodiments, the glycocalyx-restoring and -maintaining compound can be any of the compounds FTX-214, FTX-218, FTX-219, FTX 216-4, FTX 224-2, FTX 226-4, FTX 229, FTX 230, or FTX 231 (described below), alone or in combination. Each compound can be effective on its own for the indications described below and for restoring the glycocalyx (and as such they can be used individually in the methods herein), but in combination they can synergistically be used to restore and maintain the glycocalyx, and reverse inflammation, and oxidative damage that can contribute to damaging and disrupting the glycocalyx. In an illustrative embodiment, the glycocalyx-restoring and -maintaining compounds can be used in a combination of the compounds FTX-214, FTX-218, and FTX-219.

FTX-214

FTX-214 (indole acetamide) is an antioxidant and increases the antioxidative capacity to prevent build-up of reactive oxygen species that damage glycocalyx by boosting the antioxidant enzymes GSH, SOD, and CAT. FTX-214 is shown in FORMULA I. FTX-214 is shown as a salt in combination with trifluoroacetic acid in FORMULA IA, which is the form of FTX-214 used in Example 2. Other salts of FTX-214 are contemplated and are described below in "Derivatives of FTX compounds." As those of skill in the art appreciate compounds are formed as salts to increase water solubility, which can reduce toxicity.

(FORMULA I)

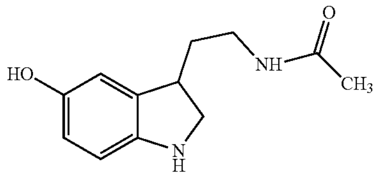

(FORMULA IA)

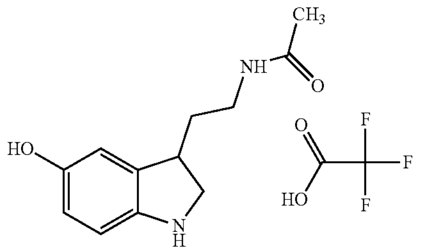

The IUPAC numbering and nomenclature for FORMULA I are shown below.

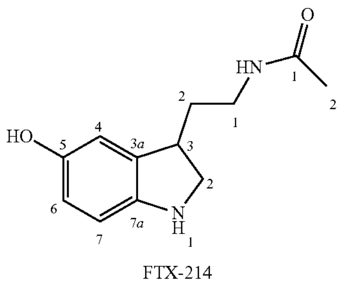

FTX-214
MW:334.30
*N*-(2-(5-hydroxyindolin-3-yl)ethyl)acetamide

FTX-218

FTX-218 (lipoate choline) is an anti-inflammatory, neutralizes cytokines, and promotes glycocalyx synthesis. FTX-218 is shown in FORMULA II.

(FORMULA II)

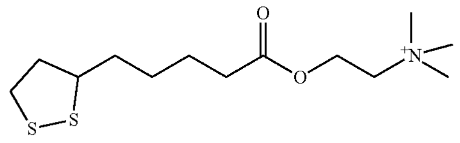

The IUPAC numbering and nomenclature for FORMULA II are shown below.

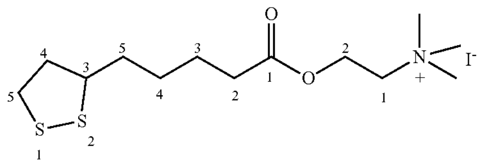

FTX-218
Molecular Weight: 419.38
2-((5-(1,2-dithiolan-3-yl)pentanoyl)oxy)-*N*,*N*,*N*-trimethylethan-1-aminium iodide

FTX-219

FTX-219 (lipoate-cysteine-glutamic tripeptide) repairs the glycocalyx and restores component building block parts and boosts synthesis of glycocalyx. FTX-219 is shown in FORMULA III. FTX-219 is shown as a salt in combination with trifluoroacetic acid in FORMULA IIIA, which is the form of FTX-219 used in Example 2. Other salts of FTX-219 are contemplated and are described below in "Derivatives of FTX compounds."

(FORMULA III)

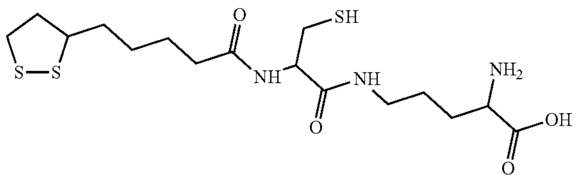

(FORMULA IIIA)

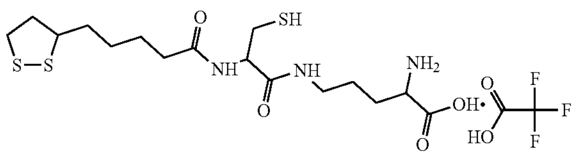

The IUPAC numbering and nomenclature for FORMULA III are shown below.

$CF_3COOH$ 2

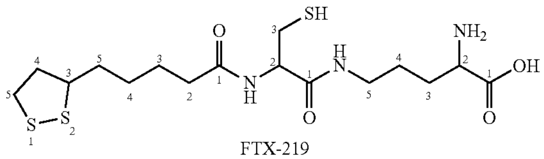

FTX-219
MW 537.63
5-(2-(5-(1,2-dithiolan-3-yl)pentanamido)-3-mercaptopropanamido)-2-aminopentanoic acid

FTX 216-4

FTX 216-4 (6-N-oxide ribose-phenazinol or myxin-1β xyloside) has the base functionality of 6-N-oxide ribose-phenazinol, as exemplified in FORMULA IV.

(FORMULA IV)

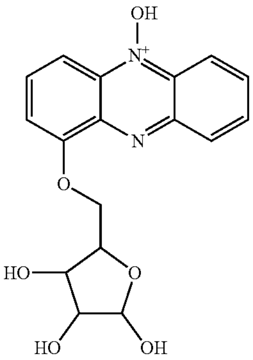

The IUPAC numbering and nomenclature for FORMULA IV are shown below.

Formula IV

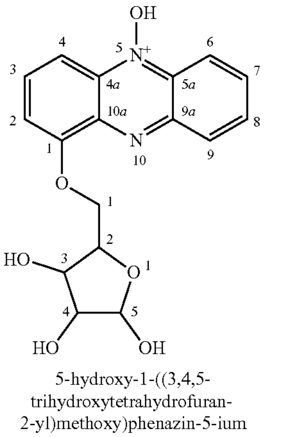

5-hydroxy-1-((3,4,5-trihydroxytetrahydrofuran-2-yl)methoxy)phenazin-5-ium

The composition in FORMULA IV stimulates chondroitin sulfate synthesis, the second-most common glycosaminoglycan (GAG) in the endothelial cell glycocalyx. ß-D-xylosides act as primers for GAG chain initiation and compete with the xylosilated core protein, which adds galactose to a xylose residue on the core protein. Xyloside activity varies with the aglycone (since primers compete with endogenous substrates and inhibit proteoglycan (PG) and glycoprotein synthesis, the type of aglycone is important). This composition is a broad-spectrum antimicrobial agent.

FTX-224-2

FTX 224-2 (dioxide isothiocyanate indole, also known as dioxide isothiocyanate pyrrole and dioxide isothiocyanate choline) was designed to inhibit blood clotting and is shown in FORMULA V. FTX 224-2 is shown as a salt in combination with trifluoroacetic acid in FORMULA VA, which is the form of FTX-224-2 used in Example 2. Other salts of FTX-224-2 are contemplated and are described below in "Derivatives of FTX compounds."

(FORMULA V)

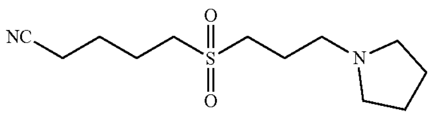

(FORMULA VA)

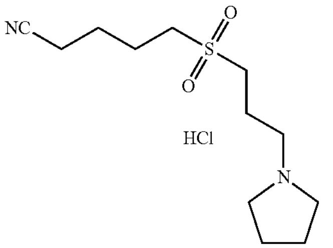

The IUPAC numbering and nomenclature for FORMULA V are shown below.

Formula V

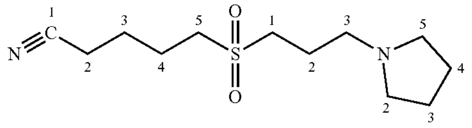

5-((3-(pyrrolidin-1-yl)propyl)sulfonyl)pentanenitrile

Also, the compound of FORMULA V acts as an anti-inflammatory agent, an antiproliferation agent, and an anti-angiogenesis agent and prevents glutathione depletion in the liver.

FTX-226-4

FTX 226-4 is a piperidine ribose, as exemplified in FORMULA VI. FTX 226-4 is shown as a salt in combination with HCl in FORMULA VIA, which is the form of FTX 226-4 used in Example 2. Other salts of FTX 226-4 are contemplated and are described below in "Derivatives of FTX compounds."

(FORMULA VI)

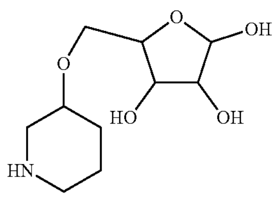

-continued (FORMULA VIA)

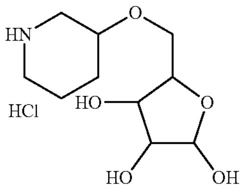

The IUPAC numbering and nomenclature for FORMULA VI are shown below.

Formula VI

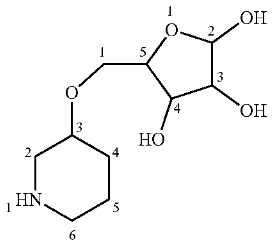

5-((piperidin-3-yloxy)methyl)tetrahydrofuran-2,3,4-triol

The compound of FORMULA VI inhibits production of two important proinflammatory mediators, IL6 and PGE2 (which triggers pain), and enhances drug bioavailability by inhibiting drug metabolism or by increasing absorption. This compound can be useful in combination treatments with other drugs by improving therapeutic effect or lowering the dose requirements of other drugs when administrated with disease-modifying antirheumatic drugs (DMARDs) as a therapeutic drug or dietary supplement. The compound is an antihypertensive, as it inhibits platelet aggregation, and stabilizes and increases activity of eNOS, which leads to decreased blood pressure.

FTX-229

FTX-229 is a nicotinyl choline, as exemplified in FORMULA VII.

(FORMULA VII)

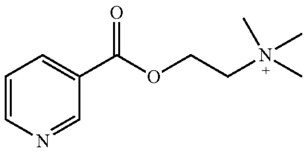

The IUPAC numbering and nomenclature for FORMULA VII are shown below.

Formula VII

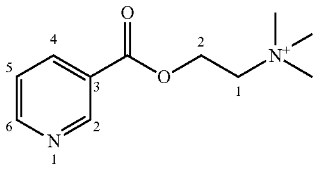

N,N,N-trimethyl-2-(nicotinoyloxy)ethan-1-aminium

After the discovery of the nicotinic acid receptor GPR109A on adipocytes and immune cells, novel direct immunomodulatory properties of nicotinic acid have been identified including the release of inflammatory mediators from adipose tissue and direct anti-inflammatory activities of nicotinic acid in other cells previously indicated as key players in atherogenesis (such as hepatocytes and endothelial and vascular cells); nicotinic acid keeps macrophages from entering the atherosclerotic vascular wall by activating its receptor, thereby halting chronic inflammation. On the other hand, choline serves various functions in mammalian bodies: in the structure of cell membranes, in protecting the liver from accumulating fat, as the precursor molecule for the neurotransmitter acetylcholine, and more. Choline, via its metabolite, trimethylglycine (betaine), is a major source for methyl groups that participate in the S-adenosylmethionine synthesis pathways, used in treating hepatitis, glaucoma, atherosclerosis, and, possible, neurological disorders.

FTX-230

FTX-230 is an ammonium lipoate, as exemplified in FORMULA VIII.

(FORMULA VIII)

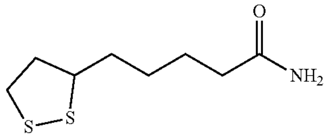

The IUPAC numbering and nomenclature for FORMULA VIII are shown below.

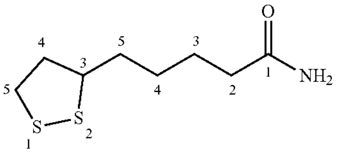

5-(1,2-dithiolan-3-yl)pentanamide

Lipoic acid is reduced to dihydrolipoic acid and serves as an antioxidant. Reduced glutathione (GSH) is the most abundant non-protein thiol in mammalian cells and the preferred substrate for several enzymes in xenobiotic metabolism and antioxidant defense, but direct use of GSH as a therapeutic agent is limited because of its unfavorable biochemical and pharmacokinetic properties.

FTX-231

FTX-231 (melatonin 6,β-D xyloside) is shown in FORMULA IX. This compound can improve the condition of the glycocalyx at least by virtue of inducing glycosaminoglycan (GAG) chain synthesis independently of a proteoglycan core protein (Thorsheim K. et al. 2016. Glycoconj J.33:245-57). The biosynthesis of GAG chains is initiated by xylose added to primer core protein followed by galactose. The enzyme xylosylprotein β1,4-galactosyltransferase 7 (β4GalT7) is an essential enzyme in the biosynthesis of GAG chains, and xylose is the optimal acceptor substrate (Siegbahn, A. et al. 2914. Chem. Sci.,5:3501-3508). Thus, the xylosilized core of GlcUA-Gal-Gal-Xyl-protein is galactosylized by β4GalT7 to produce chondroitin sulfate (CS) or heparan sulfate (HS). Alternatively, galactosyltransferase β4GalT7 transfers D-xylose from UDP-xylose to the core protein to produce heparan sulfate, heparan, chondroitin sulfate, and dermatan sulfate, depending on the tissue.

(FORMULA IX)

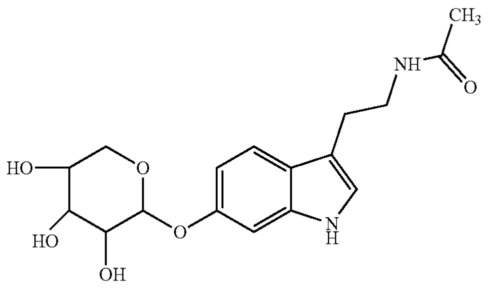

The IUPAC numbering and nomenclature for FORMULA IX are shown below.

Formula IX

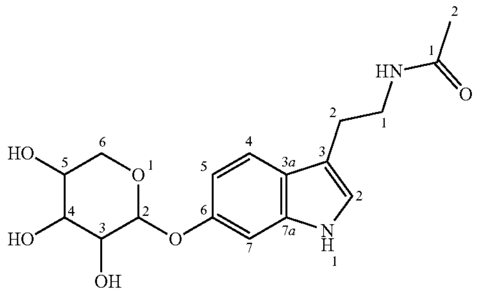

N-(2-(6-((3,4,5-trihydroxytetrahydro-2H-pyran-2-yl)oxy)-1H-indol-3-yl)ethyl)acetamide

FTX-216-1

FTX-216-1 (myxin-1beta xyloside, also known as 6-N-oxide ribose-phenazinol) generates xylose for glycosaminoglycan (GAG) maintenance and repair. GAG is linked to protein in the proteoglycans that make up the glycocalyx. FTX-216 is shown in FORMULA X.

(FORMULA X)

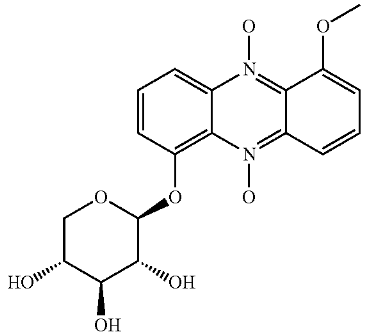

The IUPAC numbering and nomenclature for FORMULA X are shown below.

Formula X

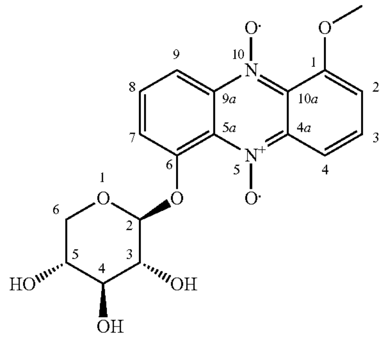

1-methoxy-6-(((2S,3R,4S,5R)-3,4,5-trihydroxytetrahydro-2H-pyran-2-yl)oxy)phenazine 5,10-dioxine

FTX-226

FTX-226 (trans-trans-trans piperine ribose) targets very low density lipoproteins (VLDL) and is shown in FORMULA XI.

(FORMULA XI)

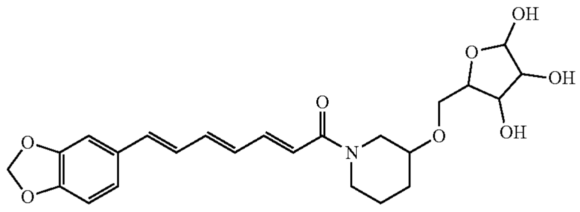

The IUPAC numbering and nomenclature for FORMULA XI are shown below.

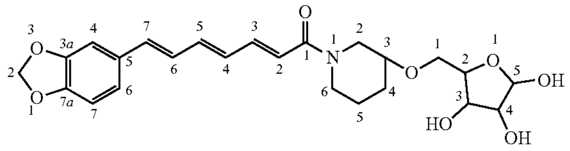

(2E,4E,6E)-7-(benzo[d][1,3]dioxol-5-yl)-1-(3-((3,4,5-trihydroxytetrahydrofuran-2-yl)methoxy)piperidin-1-yl)hepta-2,4,6-trien-1-one It should also be understood that any of the above compounds can be used individually and in any combination to achieve desired effects. Any of these compounds alone or together prevent damage or shedding of existing glycocalyx layers, as well as to provide any of the functionality described above.

Synthetic Schemes for FTX Compounds
FTX-214
FTX-214
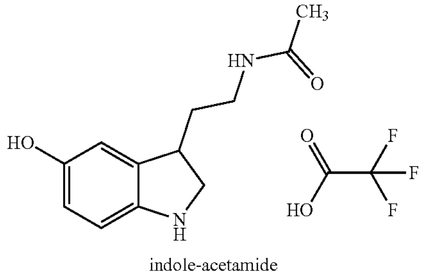
indole-acetamide
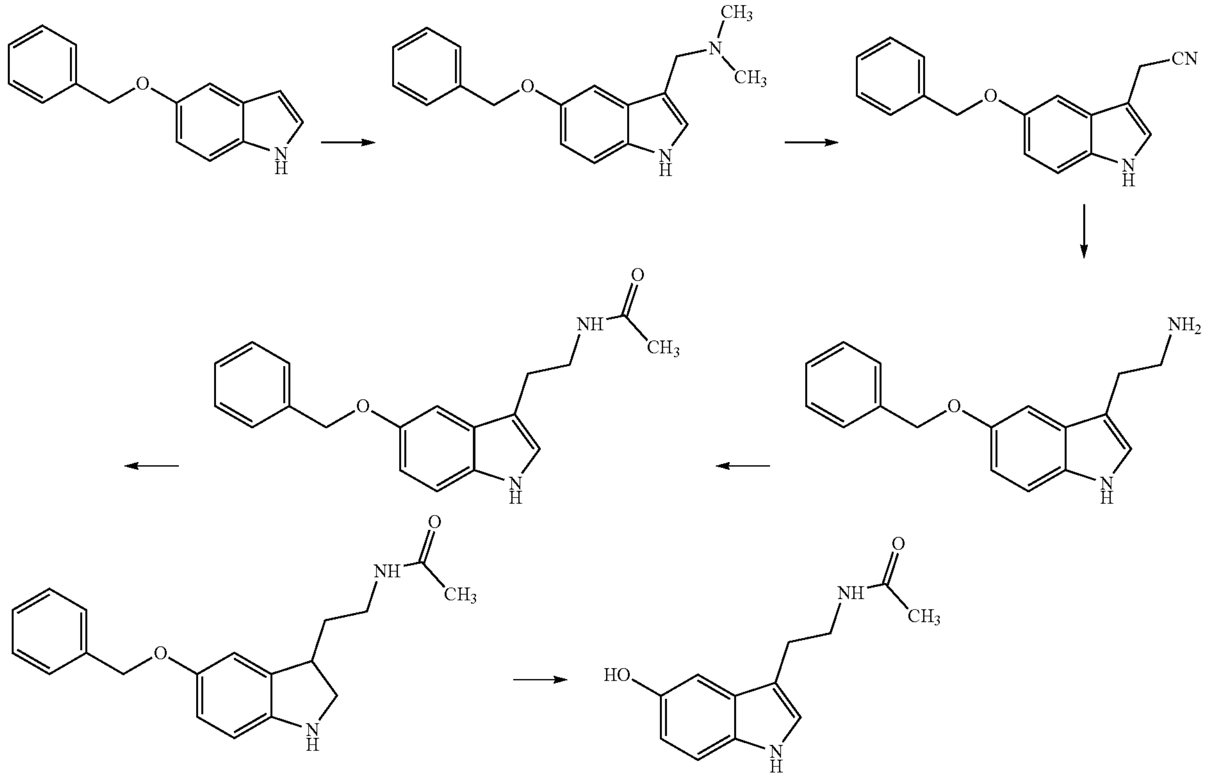
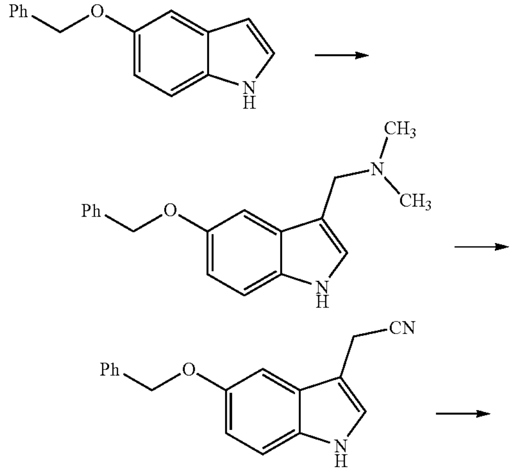

-continued

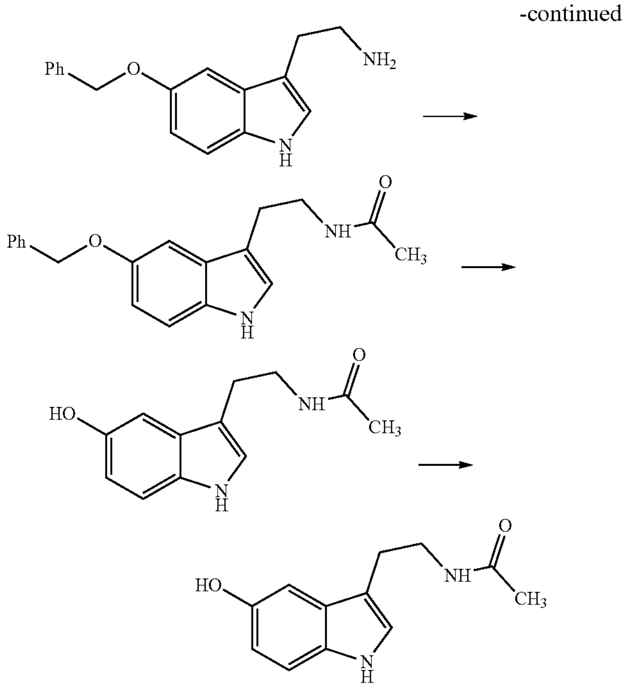

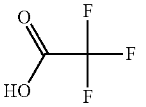

Synthetic Steps:

1. 6-(benzyloxy)-1H-indole was treated with formaldehyde, acetic acid and N,N-dimethylamine to get the Grammine.
2. Grammine converted to Cyano with NaCN, aq.DMF at 80° C.
3. Cyano reduction with $LiAlH_4$ to give amine in ether at 0° C.
4. Amine converted to N-acetyl with $Ac_2O$, $Et_3N$ in Dichloromethane.
5. Debenzyltion with Pd—C/$H_2$ in ethyl acetate.
6. Indole double bond reduction with $NaCNBH_3$ in Dichloromethane.
7. Aniline converted to TFA salt.

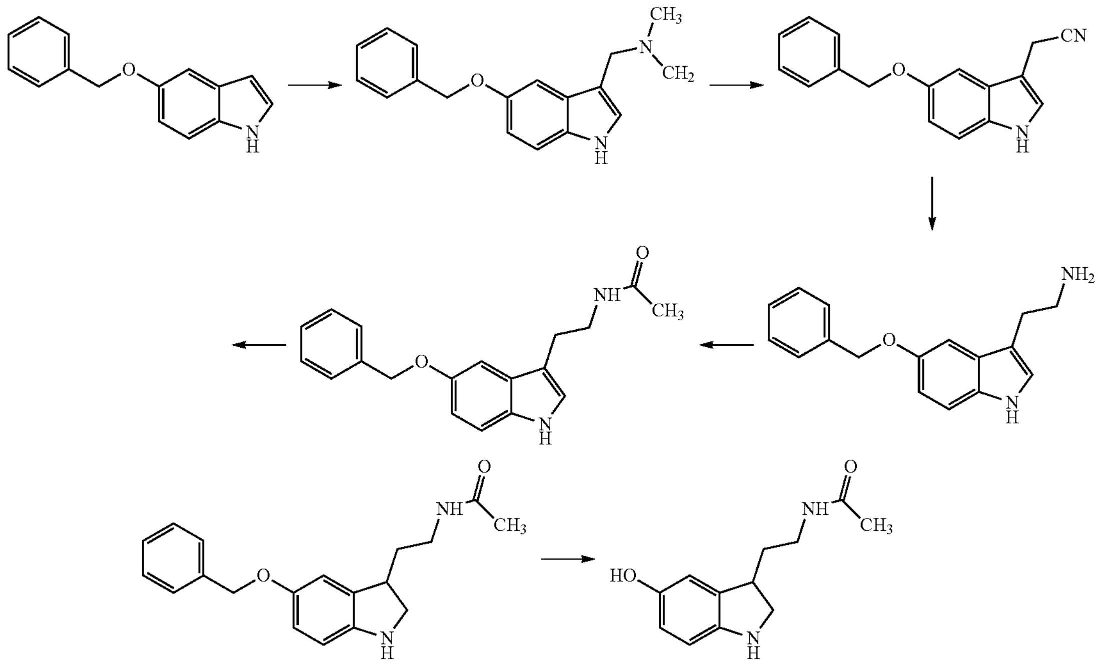

-continued

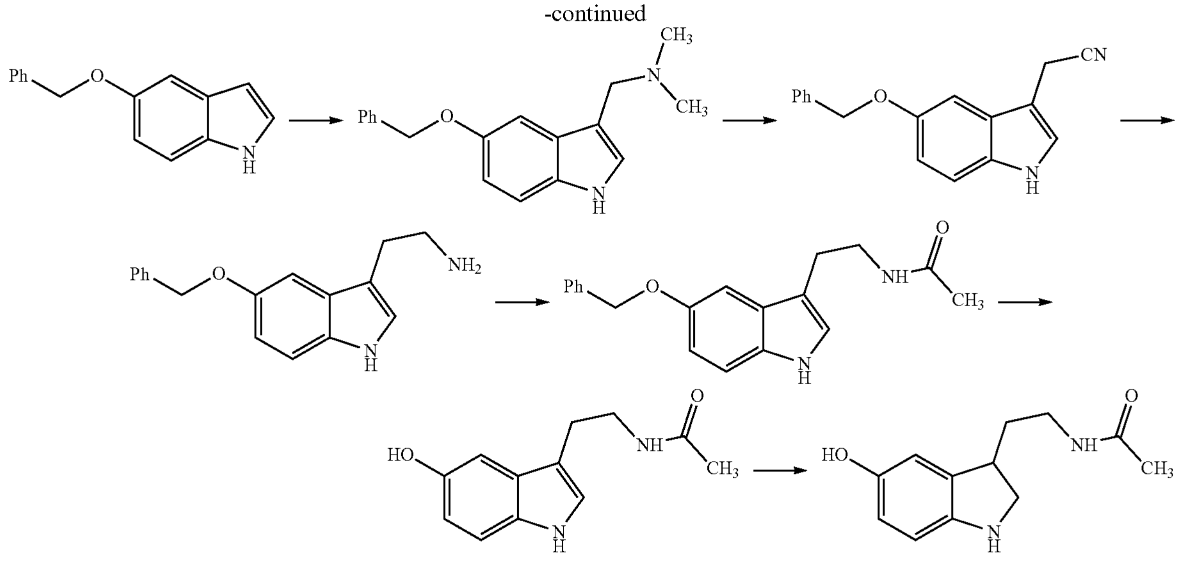

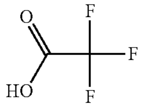

Synthetic Steps:

8. 6-(benzyloxy)-1H-indole was treated with formaldehyde, acetic acid and N,N-dimethylamine to get the Grammine.
9. Grammine converted to Cyano with NaCN, aq.DMF at 80° C.
10. Cyano reduction with $LiAlH_4$ to give amine in ether at 0° C.
11. Amine converted to N-acetyl with $Ac_2O$, $Et_3N$ in Dichloromethane.
12. Debenzyltion with Pd—C/$H_2$ in ethyl acetate.
13. Indole double bond reduction with $NaCNBH_3$ in Dichloromethane.
14. Aniline converted to TFA salt.

FTX-218

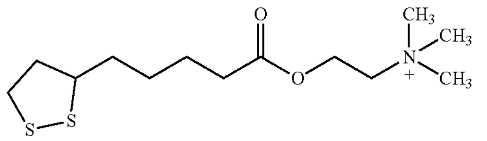

FTX-218
lipoate choline

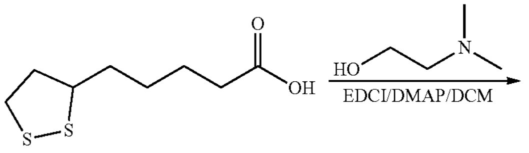

1

-continued

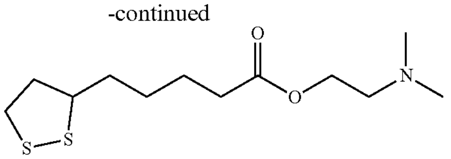

2

Synthetic steps: A solution of 1 (1.10 g, 5.34 mmol) and A (0.475 g, 5.34 mmol) in anhydrous DCM (40 mL) was added with EDCI (1.22 g, 6.41 mmol) and DMAP (65.7 mg, 0.0534 mmol) at −20° C. under $N_2$. After addition, the mixture was allowed to warm to 20° C. until no starting material was detected by TLC. Then all volatiles were removed under reduced pressure, which was purified by silica gel column chromatography to give 2 (1.20 g, yield: 81.1%) as a clear yellow oil.

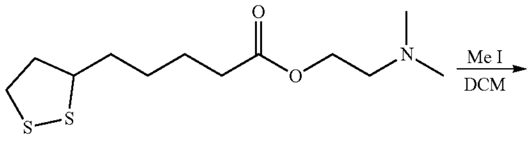

2

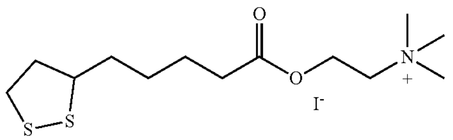

FTX-218
Name [2({5-[(3R)-1,2-dithiolan-3-yl]pentanoyl}oxy)ethyl]trimethylazanium Synthetic steps: Methyl iodide (0.681 g, 4.76 mmol) was added to a solution of the 2 (1.2 g, 4.33 mmol) in anhydrous DCM (20 mL). The reaction mixture was stirred at 20° C. overnight until no starting material was detected by TLC. The mixture was slowly poured into diethyl ether (250 mL) with vigorous stirring. The product was isolated by filtration as a yellow sold (1.40 g, yield: 77.3%).

FTX-219

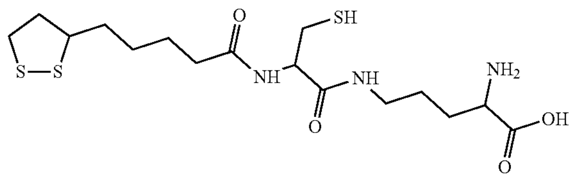

FTX-219
lipoate-cysteine-glutamate

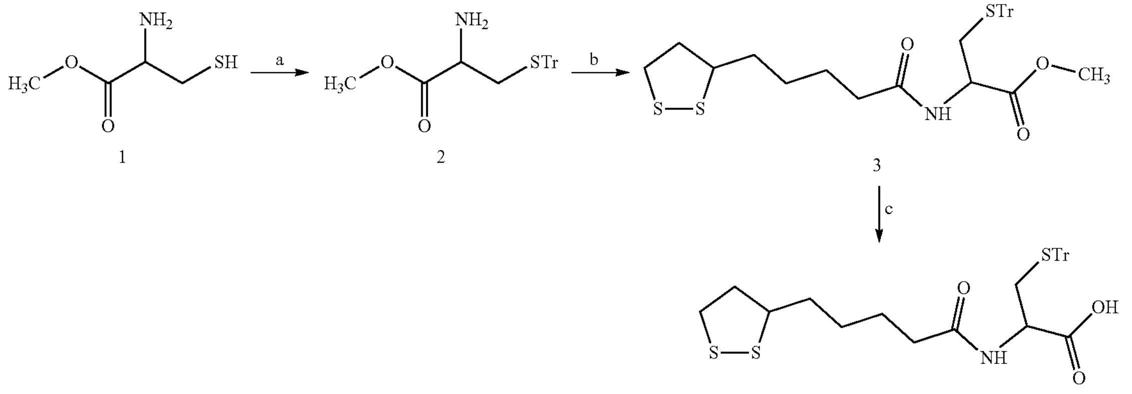

1 2 3 4

Synthetic Steps:

1. Thiol converted to trityl protection in DMF, TrCl.
2. Lipoic acid coupled with amine via EDC, HOBt, $Et_3N$, $CH_2Cl_2$.
3. Ester hydrolysis with LiOH, THF, $H_2O$, room temperature.

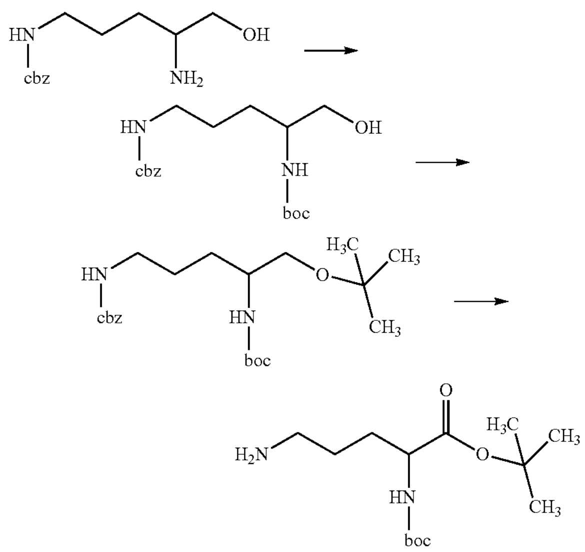

Synthetic Steps:

1. Amino acid converted to BOC-protection via $BOC_2$, THE, $H_2O$.
2. Acid converted to tert. butyl ester.
3. Cbz deprotection via Pd—C/$H_2$, ethyl acetate.

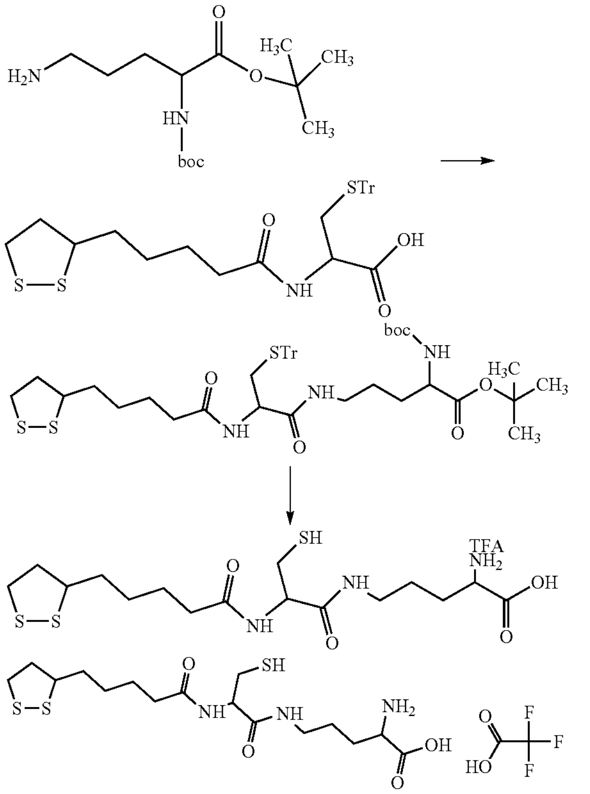

FTX-219
(lipoate-cysteine-glutamic-tripeptide) TFA salt)

Synthetic Steps:

1. Amide formation with amine and acid via EDC, HOBt, $Et_3N$, $CH_2Cl_2$.
2. Boc and trityl deprotection with TFA in $CH_2Cl_2$ to get TFA salt.

FTX-216-4

Synthetic Steps:

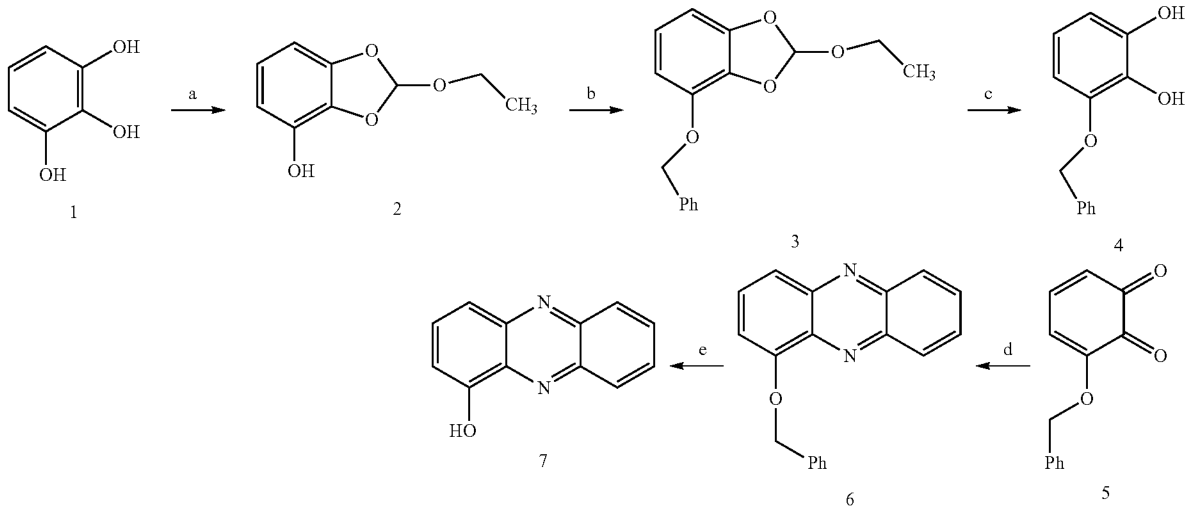

Synthetic Steps:

1. Pyrogallol converted to ketal in presence of triethoxy-formate, cat p-TSA in toluene at 100° C.
2. Free hydroxyl group converted to benzyl protection in presence of BnBr, $K_2CO_3$ in DMF.
3. Ketal deprotection with methanol, cat p-TSA.
4. Diol converted to diketone.
5. Diketone coupled with 1,2-diamino benzene gives tricyclic compound.
6. Debenzylation with Pd—C/$H_2$ in ethyl acetate gives free hydroxyl group.

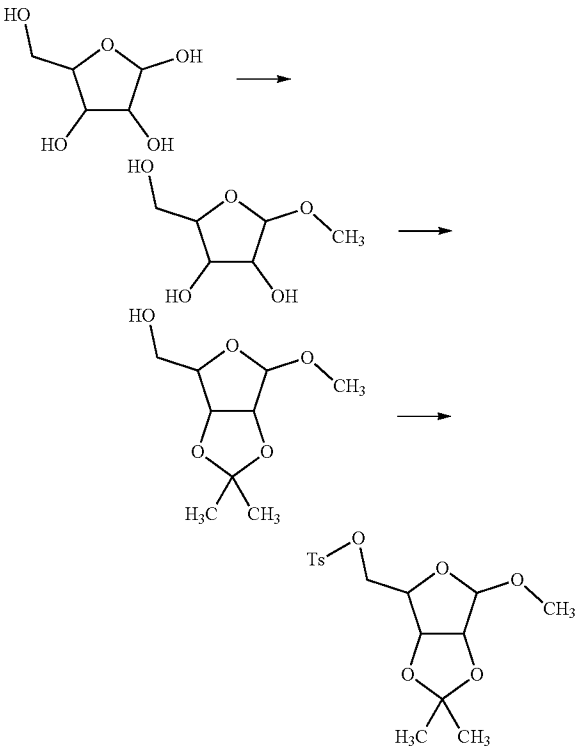

1. D-ribose converted to methyl glycoside in presence of MeOH, cat, $HaSO_4$.
2. Converted to acetal protection in presence of acetone, cat p-TSA.
3. Hydroxy converted to Tosyl in Py, TsCl.

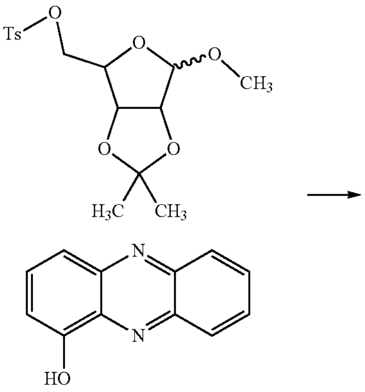

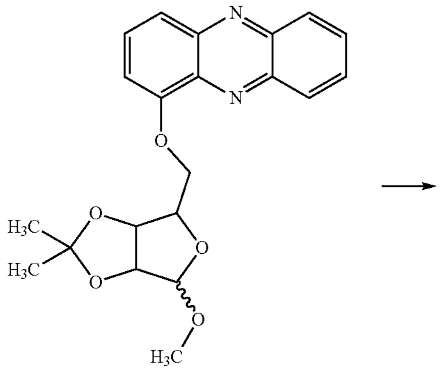

-continued

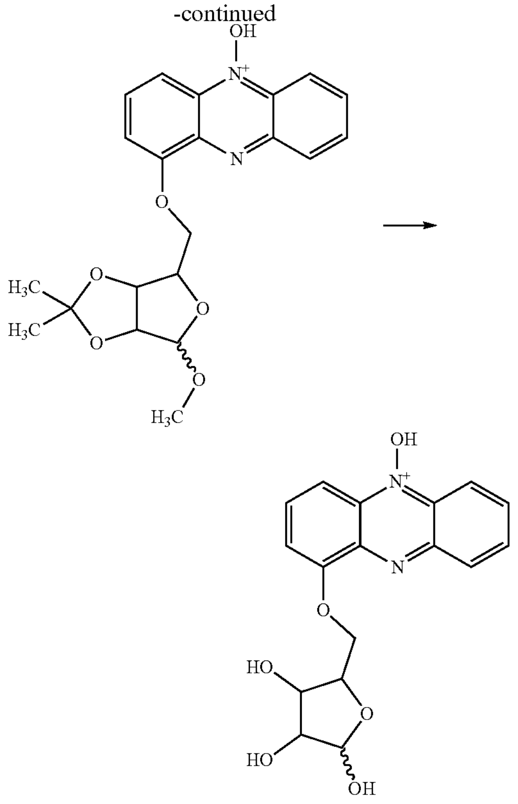

Synthetic Steps:

4. Ether coupling with tosyl give sugar attached compound.
5. N-group converted to N-Oxide.
6. Deprotection of methyl glycoside in aq. HCl.

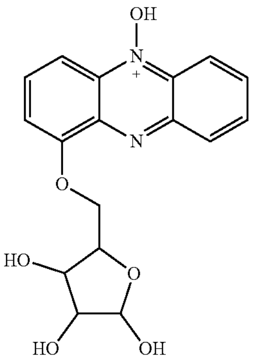

6-N-oxide ribos-phenazinol

FTX-224-2

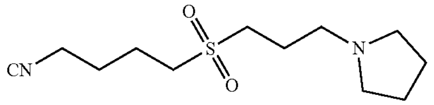

FTX-224
di-oxide isothiocyanate-pyrrole

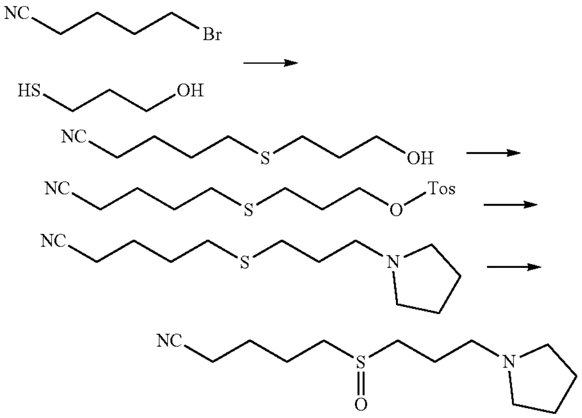

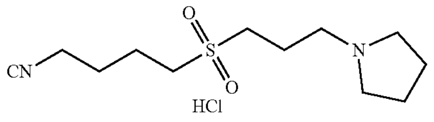

FTX-224
(dioxide isothiocyanate indole, also known as dioxide isothiocyanate choline) (HCl salt)

Synthetic Steps:

1. Thiol alkylation with TrCl.
2. Hydroxy converted to Ts group with TsCl/Py.
3. Alkylation of amine with Tosyl group.
4. Thiol group converted to S-Oxide.

FTX-226-4

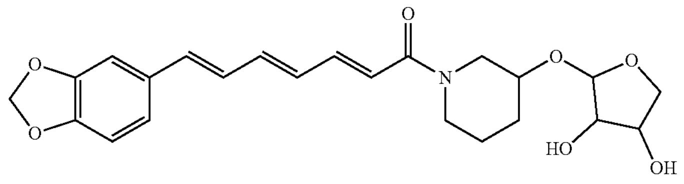

FTX-226
trans-trans-trans piperine-ribose

-continued
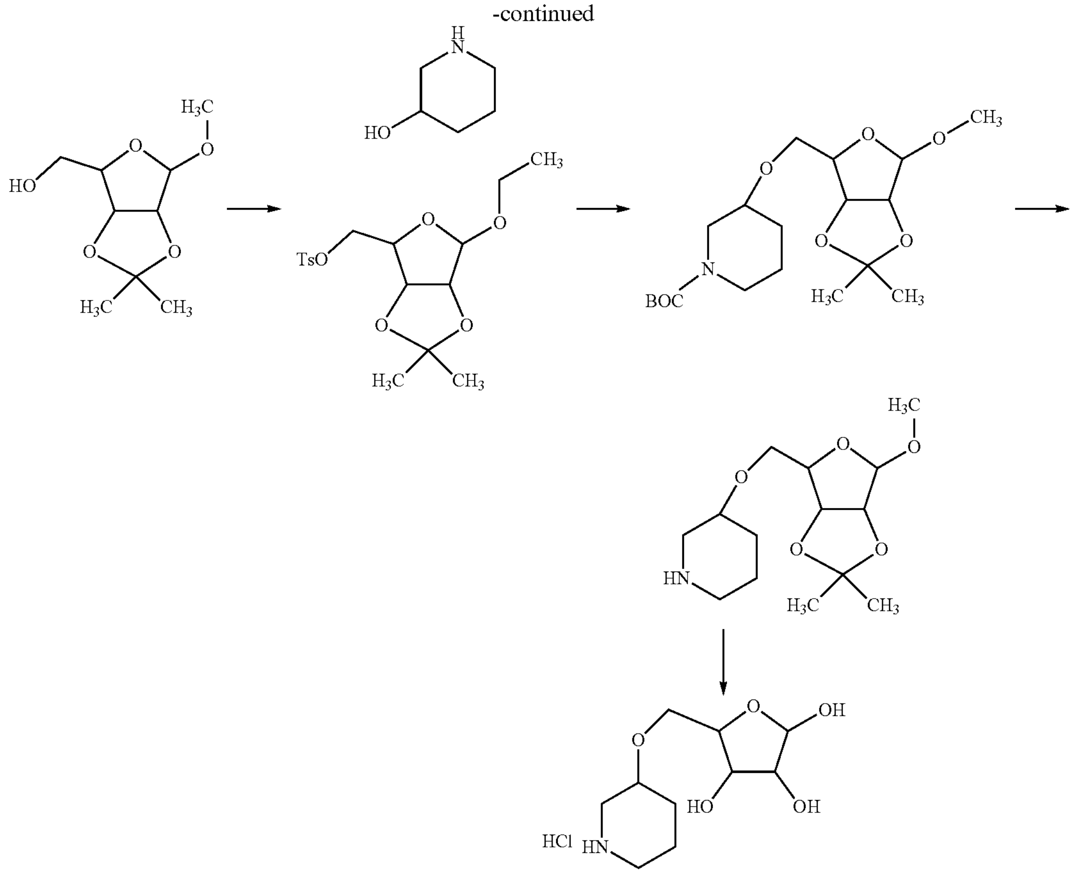
Synthetic Steps:
1. Hydroxy converted to Ts group.
2. Ts group alkylation with hydroxyl group.
3. Deprotection of Boc, acetyl and methyl glycoside.
FTX-229
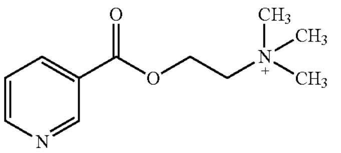
FTX-229
nicotinyl choline
1. Synthesis Route:
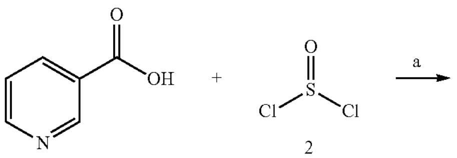
1 2
-continued
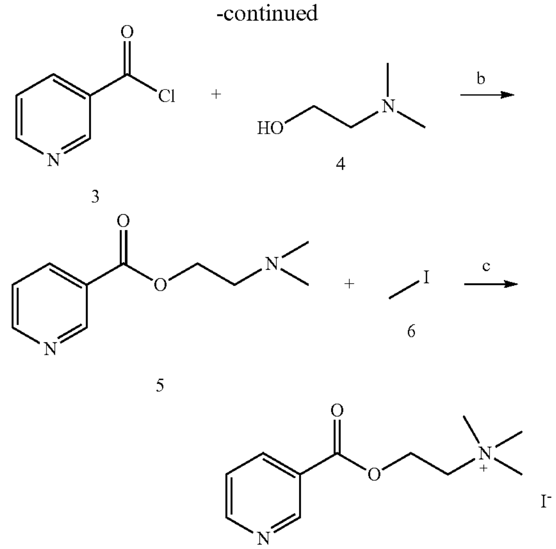
3 4 5 6 7
General Reagents and Conditions:
a. $SOCl_2$, reflux 2 h;
b. Dry $CH_2Cl_2$, r.t. 2 h, 63.5%;
c. $CH_3CH_2OH$, r.t. 2 h, 61.5%

2. Experimental Section:

2-1. The Synthesis of Compound 3:

| Sub. | Quant. | F. W. | m. mole | Equiv. |
|---|---|---|---|---|
| 1 | 2.70 g | 123 | 22 | 1 |
| 2 | 10 mL | 119 | 139 | 6.3 |

A flask with 1 (2.70 g, 22 mmol) and 2 (10 mL, 139 mmol) was heated to reflux for 2 h under $N_2$. The excess of $SOCl_2$ was removed under reduced pressure and then dissolved in dry $CH_2Cl_2$ (30 mL).

2-2. The Synthesis of Compound 5:

| Sub. | Quant. | F. W. | m. mole | Equiv. |
|---|---|---|---|---|
| 3 | | | | |
| 4 | 2.5 mL | 89 | 25 | |

The mixture of the last reaction was added drop-wise to a solution of 4 in dry $CH_2Cl_2$ (20 mL). Then the mixture was stirred for 2 h. TLC analysis showed the starting material disappeared, to the mixture was added ammonia solution until strongly alkaline. Extracted with $CH_2Cl_2$ (100 mL×3), dried over $Na_2SO_4$, and purified by flash column chromatography (eluent: $CH_2Cl/CH_3OH/TEA$=100/6/1). This protocol gave 2.972 g of product, yield 63.g %.

2-3. The Synthesis of Compound 7:

| Sub. | Quant. | F. W. | m. mole | Equiv. |
|---|---|---|---|---|
| 5 | 2.97 g | 194 | 15 | 1 |
| 6 | 4.69 g | 142 | 33 | 2.2 |

4.69 g of 6 was injected slowly in the mixture of 5 in 40 mL ethanol under $N_2$ atmosphere, and it was stirred for 2 h. The mixture was filtered, and the solid was recrystalized from hot ethanol to give 4.537 g of product, yield 61.5%.

FTX-230

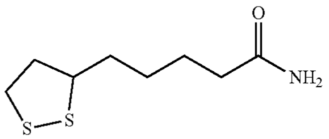 [SMILES: NC(=O)CCCCC1CCSS1]

FTX-230
ammonium lipoate

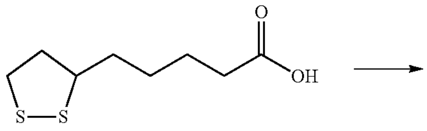

FTX-1

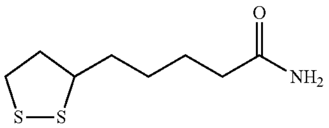

FTX-2

| | | |
|---|---|---|
| 1.0 g | $SOCl_2$, aq. $NH_3$ Fail | 0.2 g |
| 1.0 g | $SOCl_2$, $NH_3$ Fail | 0.5 g |
| 1.0 g | EDCI HoBt, aq. $NH_3$ NMR confirmed | 0.2 g |
| 5.0 g | EDCI HoBt, aq. $NH_3$ 3.4 g | 0.2 g |
| | | 0.2 g |

FTX-231

FTX-216-1

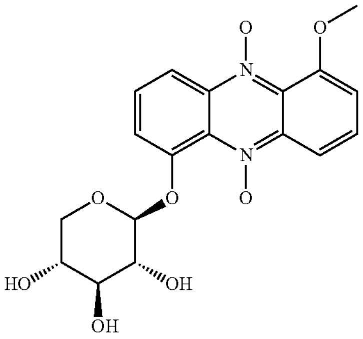

FTX-216
myxin-1β xyloside

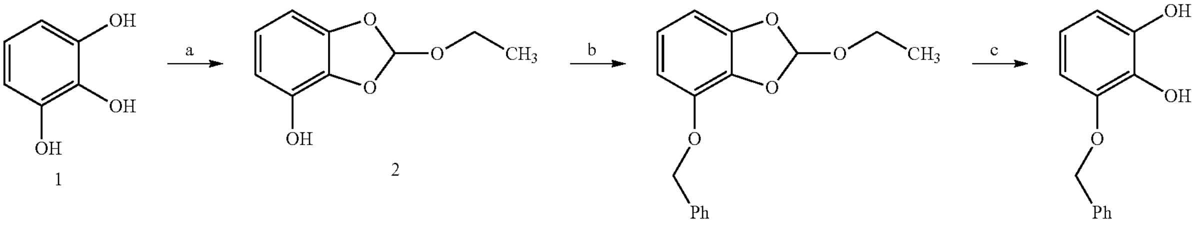

1 2 3 4

-continued

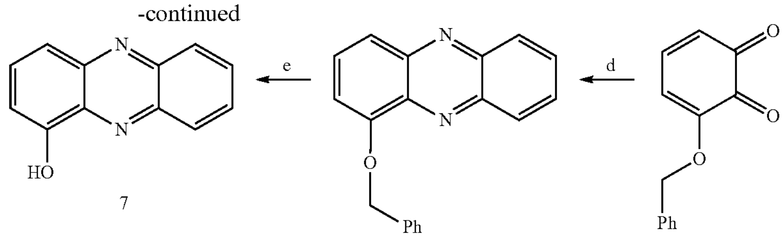

7 6 5

Synthetic Steps:

7. Pyrogallol converted to ketal in presence of triethoxyformate, cat p-TSA in toluene at 100° C.
8. Free hydroxyl group converted to Benzyl protection in presence of BnBr, $K_2CO_3$ in DMF.
9. Ketal deprotection with Methanol, cat p-TSA.
10. Diol converted to diketone.
11. Diketone coupled with 1,2-diamino benzene give tricyclic compound.
12. Debenzylation with Pd—C/$H_2$ in ethyl acetate give free hydroxyl group.

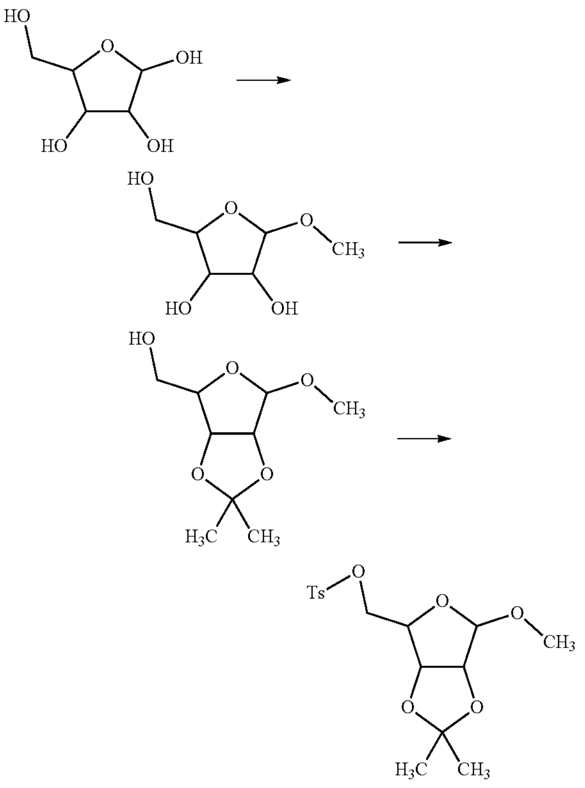

Synthetic Steps:

7. D-ribose converted to methyl glycoside in presence of MeOH, cat. $H_2SO_4$.
8. Converted to acetal protection in presence of acetone, cat p-TSA.
9. Hydroxy converted to Tosyl in Py, TsCl.

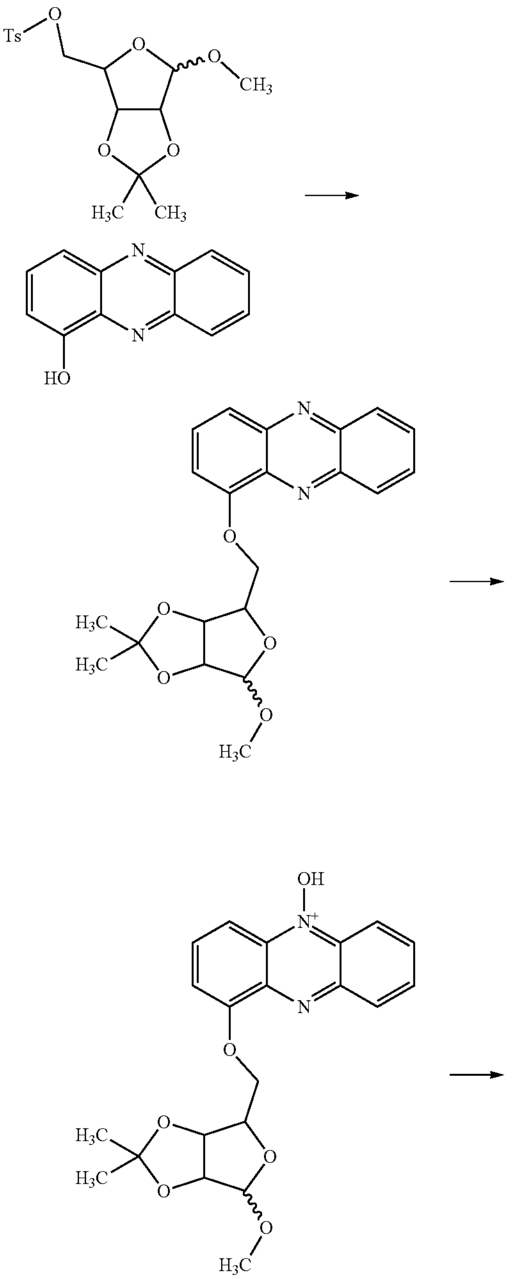

-continued

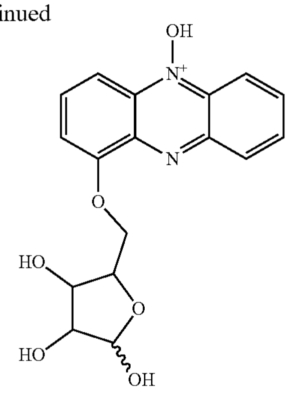

10. Ether coupling with tosyl give sugar attached compound.
11. N-group converted to N-Oxide.
12. Deprotection of methyl glycoside in aq. HCl.

Derivatives of FTX Compounds

The FTX compound(s) can be administered in the "native" form or, if desired, in the form of salts, esters, amides, prodrugs, derivatives, and the like, provided the salt, ester, amide, prodrug, or derivative is suitable pharmacologically, i.e., effective in at least one of the methods described herein. Salts, esters, amides, prodrugs, and other derivatives of the FTX compounds can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Pharmaceutically acceptable salts of the FTX compounds include those derived from pharmaceutically acceptable, inorganic and organic acids and bases. Examples of suitable acids include hydrochloric, hydrobromic, sulfuric, nitric, perchloric, fumaric, maleic, phosphoric, glycollic, lactic, salicyclic, succinic, gluconic, isethionic, glycinic, malic, mucoic, glutammic, sulphamic, ascorbic acid; toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonium. In some embodiments, one or more of the compounds described herein are used as salts of, e.g., NaCl, $NH_4F$, $MgCO_3$, and $Fe_2(HPO_4)_3$.

For example, acid addition salts are prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Illustrative acid addition salts of the FTX compounds herein are halide salts, such as may be prepared using hydrochloric or hydrobromic acids. Conversely, basic salts of the FTX compounds described herein are prepared in a similar manner using a pharmaceutically acceptable base such as sodium hydroxide, potassium hydroxide, ammonium hydroxide, calcium hydroxide, trimethylamine, or the like. Illustrative basic salts include alkali metal salts, e.g., the sodium salt, and copper salts.

Acid addition salts useful in the methods described herein include the physiologically compatible acid addition salts, most preferably the dihydrochloride. Bis-quaternary salts useful in the methods described herein include the physiologically compatible bis-quaternary salts, such as the methiodide and the dimethiodide.

Preparation of esters typically involves functionalization of hydroxyl and/or carboxyl groups and/or other reactive groups that may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

When FTX compounds (or derivatives) described herein contain chiral or prochiral centers they can exist in different stereoisomeric forms including enantiomers of (+) and (−) type or mixtures of them. The present disclosure includes in its scope both individual isomers and mixtures thereof. It will be understood that, when mixtures of optical isomers are present, they may be separated according to the classic resolution methods based on their different physicochemical properties, e.g. by fractional crystallization of their acid addition salts with a suitable optically active acid or by the chromatographic separation with a suitable mixture of solvents.

Pharmaceutical Formulations

The FTX compounds (or derivatives) described herein are typically combined with a pharmaceutically acceptable carrier (excipient), such as are described in Remington's Pharmaceutical Sciences (1980) 16th editions, Osol, ed., 1980. Pharmaceutically acceptable carriers can contain one or more physiologically acceptable compound(s) that act, for example, to stabilize the composition or to increase or decrease the absorption of the FTX compound(s) (or derivative(s)). A pharmaceutically acceptable carrier suitable for use in the methods described herein is non-toxic to cells, tissues, or subjects at the dosages employed, and can include a buffer (such as a phosphate buffer, citrate buffer, and buffers made from other organic acids), an antioxidant (e.g., ascorbic acid), a low-molecular weight (less than about 10 residues) peptide, a polypeptide (such as serum albumin, gelatin, and an immunoglobulin), a hydrophilic polymer (such as polyvinylpyrrolidone), an amino acid (such as glycine, glutamine, asparagine, arginine, and/or lysine), a monosaccharide, a disaccharide, and/or other carbohydrates (including glucose, mannose, and dextrins), a chelating agent (e.g., ethylenediaminetetraacetic acid [EDTA]), a sugar alcohol (such as mannitol and sorbitol), a salt-forming counterion (e.g., sodium), and/or an anionic surfactant (such as Tween™, Pluronics™, and PEG). In one embodiment, the pharmaceutically acceptable carrier is an aqueous pH-buffered solution.

Other pharmaceutically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the FTX compound(s) (or derivative(s)) and on their particular physio-chemical characteristics.

Suitable pharmaceutical formulations can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc. In another embodiment, one or more components of a solution can be provided as a "concentrate," e.g., in a storage container (e.g., in a premeasured volume) ready for dilution or in a soluble capsule ready for addition to a volume of water.

Pharmaceutical formulations described herein can be stored in any standard form, including, e.g., an aqueous solution or a lyophilized cake. Such compositions are typically sterile when administered to subjects. Sterilization of an aqueous solution is readily accomplished by filtration through a sterile filtration membrane. If the composition is stored in lyophilized form, the composition can be filtered before or after lyophilization and reconstitution.

In certain embodiments, the FTX compound (or derivative) may also be delivered through the skin using conventional transdermal drug delivery systems, i.e., transdermal "patches" wherein the FTX compound(s) (or derivative(s)) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir or may take some other form. The backing layer in these laminates, which serves as the upper surface of the device, preferably functions as a primary structural element of the "patch" and provides the device with much of its flexibility. The material selected for the backing layer is preferably substantially impermeable to the FTX compound(s) (or derivative(s)) and any other materials that are present.

In certain embodiments, one or more active FTX compounds (or derivatives) described herein are administered alone or in combination with other therapeutics in implantable (e.g., subcutaneous) matrices, termed "depot formulations."

A major problem with standard drug dosing is that typical delivery of drugs results in a quick burst of medication at the time of dosing, followed by a rapid loss of the drug from the body. Most of the side effects of a drug occur during the burst phase of its release into the bloodstream. Secondly, the time the drug is in the bloodstream at therapeutic levels is very short; most is used and cleared during the short burst.

Drugs (e.g., the FTX compounds or derivatives described herein) imbedded in various matrix materials for sustained release can mitigate these problems. Drugs embedded, for example, in polymer beads or in polymer wafers have several advantages. First, most systems allow slow release of the drug, thus creating a continuous dosing of the body with small levels of drug. This typically prevents side effects associated with high burst levels of normal injected or pill-based drugs. Secondly, since these polymers can be made to release over hours to months, the therapeutic span of the drug is markedly increased. Often, by mixing different ratios of the same polymer components, polymers of different degradation rates can be made, allowing remarkable flexibility depending on the agent being used. A long rate of drug release is beneficial for people who might have trouble staying on regular dosage, such as the elderly, but also represents an ease of use improvement that everyone can appreciate. Most polymers can be made to degrade and be cleared by the body over time, so they will not remain in the body after the therapeutic interval.

Another advantage of polymer-based drug delivery is that the polymers often can stabilize or solubilize proteins, peptides, and other large molecules that would otherwise be unusable as medications. Finally, many drug/polymer mixes can be placed directly in the disease area, allowing specific targeting of the medication where it is needed without losing drug to the "first pass" effect. This is certainly effective for treating the brain, which is often deprived of medicines that can't penetrate the blood/brain barrier.

A wide variety of approaches to designing depot formulations that provide sustained release of an active agent are known and are suitable for use in the methods described herein. Generally, the components of such formulations are biocompatible and may be biodegradable. Biocompatible polymeric materials have been used extensively in therapeutic drug delivery and medical implant applications to effect a localized and sustained release. See Leong et al., "Polymeric Controlled Drug Delivery," Advanced Drug Delivery Rev., 1:199-233 (1987); Langer, "New Methods of Drug Delivery," Science, 249:1527-33 (1990); Chien et al., Novel Drug Delivery Systems (1982). Such delivery systems offer the potential of enhanced therapeutic efficacy and reduced overall toxicity.

Examples of classes of synthetic polymers that have been studied as possible solid biodegradable materials include polyesters (Pitt et al., "Biodegradable Drug Delivery Systems Based on Aliphatic Polyesters: Applications to Contraceptives and Narcotic Antagonists," Controlled Release of Bioactive Materials, 19-44 (Richard Baker ed., 1980); poly (amino acids) and pseudo-poly (amino acids) (Pulapura et al. "Trends in the Development of Bioresorbable Polymers for Medical Applications," J. Biomaterials Appl., 6:1, 216-50 (1992); polyurethanes (Bruin et al., "Biodegradable Lysine Diisocyanate-based Poly (Glycolide-co-.epsilon. Caprolactone)-Urethane Network in Artificial Skin," Biomaterials, 11:4, 291-95 (1990); polyorthoesters (Heller et al., "Release of Norethindrone from Poly (Ortho Esters)," Polymer Engineering Sci., 21:11, 727-31 (1981); and polyanhydrides (Leong et al., "Polyanhydrides for Controlled Release of Bioactive Agents," Biomaterials 7:5, 364-71 (1986).

Thus, for example, the FTX compound(s) (or derivatives (s)) can be incorporated into a biocompatible polymeric composition and formed into the desired shape outside the body. This solid implant is then typically inserted into the body of the subject through an incision. Alternatively, small discrete particles composed of these polymeric compositions can be injected into the body, e.g., using a syringe. In an illustrative embodiment, the FTX compound(s) (or derivatives(s)) can be encapsulated in microspheres of poly (D,L-lactide) polymer suspended in a diluent of water, mannitol, carboxymethyl-cellulose, and polysorbate 80. The polylactide polymer is gradually metabolized to carbon dioxide and water, releasing the FTX compound(s) (or derivatives(s)) into the system.

In yet another approach, depot formulations can be injected via syringe as a liquid polymeric composition. Liquid polymeric compositions useful for biodegradable controlled release drug delivery systems are described, e.g., in U.S. Pat. Nos. 4,938,763; 5,702,716; 5,744,153; 5,990,194; and 5,324,519. After injection in a liquid state or, alternatively, as a solution, the composition coagulates into a solid.

One type of polymeric composition suitable for this application includes a nonreactive thermoplastic polymer or copolymer dissolved in a body fluid-dispersible solvent. This polymeric solution is placed into the body where the polymer congeals or precipitates and solidifies upon the dissipation or diffusion of the solvent into the surrounding body tissues. See, e.g., Dunn et al., U.S. Pat. Nos. 5,278,201; 5,278,202; and 5,340,849 (disclosing a thermoplastic drug delivery system in which a solid, linear-chain, biodegradable polymer or copolymer is dissolved in a solvent to form a liquid solution).

The FTX compound(s) (or derivative(s)) can also be adsorbed onto a membrane, such as a silastic membrane, which can be implanted, as described in International Publication No. WO 91/04014. Other illustrative implantable sustained release systems include, but are not limited to Re-Gel®, SQ2Gel®, and Oligosphere® by MacroMed, ProLease® and Medisorb® by Alkermes, Paclimer® and Gliadel® Wafer by Guilford pharmaceuticals, the Duros implant by Alza, acoustic biSpheres by Point Biomedical, the Intelsite capsule by Scintipharma, Inc., and the like.

Treatment Methods

The glycocalyx-restoring and -maintaining compounds described above can be used alone or in any combination to treat, restore, and maintain any membrane that has a glycocalyx and/or to reduce endothelial inflammation and/or oxidative damage to the endothelium. The membrane treated can be, but is not limited to, blood vessels, lungs, endometrial linings, digestive tract linings, epithelium, or any other lining in the body.

The integrity of the endothelial glycocalyx is determined by the balance between shedding and synthesis, but under pathologic conditions, the balance is disrupted, resulting in the shedding of one or more of its components (e.g., heparan sulfate, syndecan-1, or hyaluronic acid) into the blood. However, the balance can be restored and the glycalyx rebuilt by self-assembly to its native hydrodynamical thickness within as little as 5 to 7 days (2009. Circul Res 2009; 104:1318-1325.) Heparan sulfate (HS) has been demonstrated to be restored on the surface of endothelial cells in 20 h in vitro (2013. Cell Mol Bioeng 6:160-174). Example 2 below demonstrates the ability of combinations of glycocalyx-restoring and -maintaining compounds described above to prevent and/or cure arterial plaque in a proprietary animal model of atherosclerosis.

The present disclosure provides for a method of treating multiple disease causes, by administering a composition including a glycocalyx-restoring and -maintaining compound to an individual, restoring the glycocalyx, reversing inflammation, and reversing oxidative damage. The glycocalyx-restoring and -maintaining compound treats the root cause of a disease, restores the glycocalyx, and maintains the glycocalyx. The glycocalyx-restoring and -maintaining compound can be any of those described above. Normal blood flow shear is necessary for a balanced shedding and synthesis of the proteoglycan components of the glycocalyx and maintaining the residency of various enzymes and signaling molecules including the antioxidant superoxide dismutase (SOD), anti-inflammatory antithrombin (AT-III), and proteases (thrombin, plasmin, protease-3, and elastase that are important in blood clotting, immunity, and inflammation). Once the balance of these resident enzymes are disrupted, glycocalyx shedding ensues followed by a cascade of pathological events. Thus, the therapeutic approach of the present disclosure that improves the glycocalyx structure and function also can prevent the pathological processes connected with vascular inflammation. The composition is able to restore the balance of the enzymes discussed above.

More specifically, in particular embodiments, the disease being treated can be any cardiovascular disease (CVD), as CVD involves disruption of the glycocalyx, inflammation, and oxidative damage resulting in eventual clot formation and travel of the clot to small vessels, resulting in flow disruption (i.e. stroke, etc.). Therefore, the present disclosure provides for a method of treating CVD, by administering a composition including glycocalyx-restoring and -maintaining compound to an individual, restoring the glycocalyx, reversing inflammation, or reversing oxidative damage (and preferably achieving all three). The CVD being treated can be, but is not limited to, coronary heart disease, myocardial infarction, stroke, hypertension, atrial fibrillation, congestive heart failure, congenital heart condition, peripheral arterial disease, venous thrombosis, deep venous thrombosis, and pulmonary embolism.

The disease being treated with the glycocalyx-restoring and -maintaining compound can also be any disease with the indications of disrupted glycocalyx, inflammation, and/or oxidative damage. For example, a disrupted glycocalyx can be indicated in damage to the body (as the glycocalyx cushions the plasma membrane and protects it from chemical injury), impaired immunity to infection (as the glycocalyx enables the immune system to recognize and selectively attack foreign organisms), cancer (as changes in the glycocalyx of cancerous cells enable the immune system to recognize and destroy them), transplant rejection (as the glycocalyx forms the basis for compatibility of blood transfusions, tissue grafts, and organ transplants), cell adhesion issues (as the glycocalyx binds cells together so that tissues do not fall apart), inflammation regulation diseases (as the glycocalyx coating on endothelial walls in blood vessels prevents leukocytes from rolling/binding in healthy states), fertilization issues (as the glycocalyx enables sperm to recognize and bind to eggs), embryonic development issues (as the glycocalyx guides embryonic cells to their destinations), and diabetes.

Inflammation can be implicated in plasma cell leukemia, rheumatoid arthritis, multiple myeloma, Lennert syndrome, Castleman's disease, cardiac myxomas, liver cirrhosis, chronic polyarthritis, bacterial and viral meningitis, graft-versus-host reactions, intra-amniotic infections, inflammatory intestinal disease, many cancers and advanced cancers (including pancreatic cancer), encephalitis, decreased gene expression, schizophrenia, depression, bacterial, viral, fungal, parasitic infections, microbial toxin exposure, tissue necrosis, foreign body presence, immune reaction, acne vulgaris, asthma, autoimmune diseases, celiac disease, chronic prostatitis, glomerulonephritis, hypersensitivities, inflammatory bowel diseases, pelvic inflammatory disease, reperfusion injury, sarcoidosis, transplant rejection, vasculitis, interstitial cystitis, atherosclerosis, allergies, myopathies, leukocyte defects, endometriosis, and multiple sclerosis.

Oxidative damage can be implicated in cancer, Parkinson's disease, Alzheimer's disease, atherosclerosis, heart failure, myocardial infarction, fragile X syndrome, sickle cell disease, lichen planus, vitiligo, autism, infection, and chronic fatigue syndrome.

It should be understood that the glycocalyx-restoring and -maintaining compound can not only reverse the diseases listed above but can also prevent their occurrence and inhibit their progression.

In particular embodiments, the present disclosure generally provides for a method of treating multiple disease causes, by administering a combination therapeutic to an individual, and targeting multiple causes of a disease. The combination therapeutic has multiple components necessary to target each underlying cause of a disease. Many diseases (such as CVD, cancer, diabetes, or any other disease described below) have multiple mechanisms involved in their presentation. For example, the causes of the disease can include glycocalyx disruption, inflammation, and oxidative damage. In order to treat this disease, the combination therapeutic can include a component that can target glycocalyx disruption, a component that can target inflammation, and a component that can target oxidative damage. The multiple components can be in a single poly pill. One example of the combination therapeutic is the glycocalyx-restoring and -maintaining compounds of the combination of FTX-214, FTX-218, and FTX-219 described above. Previously, diseases were treated just by their symptoms and not their underlying causes, or a single composition was given to treat the underlying cause (as with antibiotics). The present disclosure allows for multiple components to be administered (preferably within a single pill) that each target a different cause of disease, making it easier for a patient to take their medicine as well as targeting the root causes of their disease.

Since the glycocalyx-restoring and -maintaining compound can treat any one of disruption of the glycocalyx, inflammation, and oxidative damage individually or in combination, the present disclosure also includes the following methods. A method of restoring the glycocalyx is provided by administering a composition including the glycocalyx-restoring and -maintaining compound to an individual and restoring the glycocalyx. A method of reversing inflammation is provided by administering a composition including the glycocalyx-restoring and -maintaining compound to an individual, reversing inflammation, and restoring the glycocalyx. In other words, by reversing inflammation which can be causing disruption and damage of the glycocalyx, the glycocalyx can be restored to normal function. A method of reversing oxidative damage is provided by administering a composition including the glycocalyx-restoring and -maintaining compound to an individual, reversing oxidative damage, and restoring the glycocalyx. In other words, by reversing oxidative damage which can be causing disruption and damage of the glycocalyx, the glycocalyx can be restored to normal function.

Route of Administration and Dose

The composition of the present disclosure is administered and dosed in accordance with good medical practice, taking into account the clinical condition of the individual patient, the site and method of administration, scheduling of administration, patient age, sex, body weight, and other factors known to medical practitioners. The pharmaceutically "effective amount" for purposes herein is thus determined by such considerations as are known in the art.

Multiple FTX compounds (or derivatives), e.g., used in any of the combination therapies described herein can be administered by the same, or different, route(s) of administration. Where possible, it is generally desirable to administer these agents by the same route of administration, preferably in the same formulation. However, differences in pharmacodynamics, pharmacokinetics, or other considerations may dictate the co-administration of selected compound and additional agent in separate formulations.

In the treatment methods of the present disclosure, the compositions of the present disclosure can be administered in various ways. It should be noted that they include one or more of the compounds and can be administered alone or as one or more active ingredients in combination with one or more pharmaceutically acceptable carriers, diluents, adjuvants and vehicles. The compounds can be administered topically, orally, buccally, subcutaneously, rectally, intravaginally, or parenterally, including intravenously, intra-arterially, intradermally, intramuscularly, intracavitarally, intracisternally, intraperitoneally, intratonsillarly, and intranasally, as well as intrathecally and by infusion. Implants of the compounds are also useful.

The subject being treated is a warm-blooded animal and, in particular, mammals, including humans. Examples of suitable subjects include, e.g., research animals or pets, such as mice, rats, guinea pigs, rabbits, cats, dogs, as well as monkeys and other primates. In certain embodiments, the subject is human. The pharmaceutically acceptable carriers, diluents, adjuvants and vehicles as well as implant carriers generally refer to inert, non-toxic solid or liquid fillers, diluents or encapsulating material not reacting with the active ingredients of the disclosure.

In various embodiments, the FTX compounds (or derivatives) described herein can be administered orally, in which case delivery can be enhanced by the use of protective excipients. This is typically accomplished either by complexing the FTX compound(s) (or derivatives(s)) with a composition to render them resistant to acidic and enzymatic hydrolysis or by packaging the agents in an appropriately resistant carrier, e.g. a liposome. Means of protecting agents for oral delivery are well known in the art (see, e.g., U.S. Pat. No. 5,391,377).

When administering a compound of the present disclosure parenterally, it will generally be formulated in a unit dosage injectable form (solution, suspension, emulsion). Pharmaceutical compositions suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles, such as cottonseed oil, sesame oil, olive oil, soybean oil, corn oil, sunflower oil, or peanut oil, and esters, such as isopropyl myristate, may also be used as solvent systems for compound compositions. Additionally, various additives that enhance the stability, sterility, and isotonicity of the compositions, including anti-microbial preservatives, antioxidants, chelating agents, and buffers, can be added. Prevention of the action of microorganisms can be ensured by various antibacterial and anti-fungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present disclosure, however, any vehicle, diluent, or additive used would have to be compatible with the compounds.

Sterile injectable solutions can be prepared by incorporating the compounds utilized in practicing the present disclosure in the required amount of the appropriate solvent with various of the other ingredients, as desired. Sterility can be ensured by using sterile components and a sterile process during formulation or by sterilizing post-formulation.

Compositions including the compounds of the present disclosure can be administered parenterally to the subject in the form of slow-release subcutaneous implants or targeted delivery systems such as monoclonal antibodies, vectored delivery, iontophoretic delivery, and/or delivery employing polymer matrices, liposomes, and/or microspheres. Examples of delivery systems useful in the present disclosure include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

In illustrative embodiments, the compounds described herein can be administered orally and preferably in a single dosage form. Doses can be administered as single doses or multiple doses over a period of several days. The treatment generally has a length that varies with the length of the disease process and drug effectiveness and the species of the subject being treated.

In therapeutic applications, one or more of the active agents described herein is/are administered to a subject in an amount sufficient to treat disruption of the glycocalyx, inflammation, and/or oxidative damage. Amounts effective for this use may depend upon disease status, the degree of improvement sought, and the general state of the subject's health. Single or multiple administrations of the active agent(s) may be administered depending on the dosage and frequency as required and tolerated by the subject.

The concentration of active agent(s) can vary widely and will be selected primarily based on fluid volumes, viscosities, body weight and the like in accordance with the particular mode of administration selected and the subject's needs. In accordance with standard practice, the clinician can titer the dosage and modify the route of administration as required to obtain the optimal therapeutic effect. Generally, the clinician begins with a low dose and increases the dosage until the desired therapeutic effect is achieved. Starting doses for a given active agent can, for example be extrapolated from in vitro and/or animal data.

In particular embodiments, concentrations of FTX compound(s) (or derivative(s)) will typically be selected to provide dosages ranging from about 10 μg/kg/day to about 200 mg/kg/day and sometimes higher. In various embodiments, dosages range from about 25 μg/kg/day to about 175 mg/kg/day, specifically from about 50 μg/kg/day to about 150 mg/kg/day, more specifically from about 75 μg/kg/day to about 125 mg/kg/day, even more specifically from about 90 μg/kg/day to about 100 mg/kg/day, e.g., about 0.1-100 mg/kg/day. It will be appreciated that such dosages may be varied to optimize a therapeutic regimen in a particular subject or group of subjects, and thus any of these values can represent the upper or lower limit of a suitable dosage range according to the invention (e.g., about 10 μg/kg/day to about 100 mg/kg/day).

When used in combination, the compounds can be used as the same or different dosages. Thus, compounds in a two-drug combination can be used in a 1:1 ratio (by weight) or in, e.g., a 1:2, 1:3, 1:4, 1:5, or other ratio. Compounds in a three-drug combination can be used in a 1:1:1 ratio (by weight) or in any of a number of possible ratios, including, but not limited to, e.g., 1:2:1, 1:3:1, 1:4:1, 1:5:1, 1:2:2, 1:2:3, 1:2:4, 1:2:5, 1:3:3, 1:3:4, 1:3:5, 1:4:4, 1:4:5, 1:5:5 and so forth, for combinations containing additional compounds. In some embodiments the effects of individual compounds are additive. In some embodiments, the effects of individual compounds are synergistic. I some embodiments, the use of a combination of compounds allows the use of a lower dose of one or more of the compounds in the combination. The determination of a suitable dose of the compound(s) for treating a particular condition in a particular subject is within the level of skill in the art in light of the guidance provided herein.

In illustrative embodiments, the dose for any of the compounds can 5 mg to 750 mg (per 70 kg average human weight). In the preferred combination, the dose can be 50 mg FTX-214, 50 mg FTX-218, and 50 mg FTX-219 (effective dose) up to 750 mg FTX-214, 750 mg FTX-218, and 750 mg FTX-219 (maximum tolerated dose). A 50 mg dose proved to prevent or reverse the disruption of the glycocalyx as evidenced by reversion of plaque formation, as shown in FIGS. 12A-12H (B; FTX-226-4+FTX-229+FTX-214; F: FTX-224-2+FTX-216+FTX-214; I: FTX-216+FTX-214+FTX-218; and K: FTX-214+FTX-218+FTX-219).

Co-Administration with Other FTX Compounds

Compositions including the glycocalyx-restoring and -maintaining compounds described herein can be administered in combination with one or more other therapeutic agents to treat specific diseases and conditions. The therapeutic agents can include, but are not limited to, non-steroidal anti-inflammatory drugs (NSAIDS) such as, but not limited to, acetaminophen, salicylates (e.g., aspirin, diflunisal, salsalate), acetic acid derivatives (e.g., indomethacin, ketorolac, sulindac etodolac, diclofenac, nabumetone), propionic acid derivatives (e.g., ibuprofen, naproxen, flurbiprofen, ketoprofen, oxaprozin, fenoprofen, loxoprofen), fenamic acid derivatives (e.g., meclofenamic acid, mefenamic acid, flufenamic acid, tolfenamic acid), oxicam (e.g., enolic acid) derivatives (e.g., piroxicam, meloxicam, tenoxicam, droxicam, lornoxicam, isoxicam), arylalkanoic acid derivatives (e.g., tolmetin); or selective COX-2 inhibitors (e.g., celecoxib, rofecoxib, valdecoxib, parecoxib, lumiracoxib, etoricoxib, firocoxib), as well as narcotic analgesics (e.g., morphine, codeine, oxycodone, and other opiates). The therapeutic agent can also be generally from the one or more of the following classes: antihistamines, anti-infective agents, antineoplastic agents, autonomic drugs, blood derivatives, blood formation agents, coagulation agents, thrombosis agents, cardiovascular drugs, cellular therapy, central nervous system agents, contraceptives, dental agents, diagnostic agents, disinfectants, electrolytic, caloric, and water balance agents, enzymes, respiratory tract agents, eye, ear, nose, and throat preparations, gold compounds, heavy metal antagonists, hormones and synthetic substitutes thereof, oxytocics, radioFTX compounds, serums, toxoids, vaccines, skin and mucous membrane agents, smooth muscle relaxants, and vitamins. These therapeutic agents can be administered at the same time, before, or after the glycocalyx-restoring and -maintaining compound, they can be in separate or the same dosage form, and they can have different or the same release profiles.

The compositions disclosed herein offer the advantage over conventional therapies that they treat the underlying causes of disease and not simply the symptoms. In some cases, however, it may be advantageous to do both. Accordingly, the present disclosure provides a method that entails co-administering a composition including a glycocalyx-restoring and -maintaining compound and one or more symptom-targeted drugs. There is an array of symptom-targeted drugs currently marketed against cardiovascular disease including cholesterol-lowering drugs such as statins and fibrates for CHD; diuretics, ACE inhibitors, ARBs, calcium inhibitors, and B-blockers for hypertension; and anti-clotting drugs, such as anti-coagulants (e.g. heparan, rivaroxaban, low molecular weight heparan, dabigatran etexilate mesylate, bivalirudin, coumadin, abciximab, eprifibatide, tirofiban), anti-platelet drugs (e.g. clopidogrel bisulfate, prasugrel, ticagrelor, cilostazol, aspirin, terutroban, dipyridamole), and fibrinolytics (e.g. tissue plasminogen activator (tPA), streptokinase) for stroke.

Receptor Function

Receptors are imbedded in and pass through the glycocalyx: transmembrane glycoprotein receptors account for a significant number of membrane-bound receptors, and the disruption of the glycocalyx, can render dysfunctional and structurally disrupt these membrane-bound receptors. The glycocalyx-restoring and -maintaining compound can restore the glycocalyx and restore structural integrity and function to those receptors. Therefore, the present disclosure provides for a method of restoring the structural and functional integrity of receptors in the glycocalyx by administering the glycocalyx restoring and maintaining compound to an individual and restoring structural integrity and function of receptors imbedded in and passing through the glycocalyx.

The receptors in the glycocalyx can be for various antigens and antibodies, both polyclonal and monoclonal. By restoring the receptor integrity, the total systemic effect of the ligand for the receptor (e.g., antigen or antibody) can be restored to a healthy condition and effectively increased. The activity can be metabolic, immunologic, or any other activity that is receptor-controlled. The response of antibodies can be potentiated with administration of the glycocalyx-restoring and -maintaining compound because the receptors they bind to are restored.

Therefore, the present disclosure provides for a method of restoring the glycocalyx and receptors therein and potentiating drug response, by administering a composition including a glycocalyx-restoring and -maintaining compound and co-administering an antibody to an individual suffering from disease, restoring the glycocalyx, restoring receptors in the glycocalyx, and potentiating the response to the antibody. The present disclosure also provides for a composition for treating diseases including the glycocalyx-restoring and -maintaining compound and an antibody. The components of this combination can be in the same dosage form or in different dosage forms and can be administered with different or with the same release profiles.

The disease being treated by co-administration of a glycocalyx-restoring and -maintaining compound and an antibody can be any disease or condition for which an antibody can be used to treat, such as, but not limited to, autoimmune diseases, cancers, metabolic disorders, or infectious diseases. The receptor being restored can be any receptor that the particular antibody binds to or otherwise interacts with.

The antibody can generally be any suitable monoclonal or polyclonal antibody, such as, but not limited to, 3F8, 8H9, abagovomab, abciximad, abrilumab, actoxumab, adalimumab, adecatumumab, aducanumab, afelimomab, afutuzumab, alacizumab pegol, ALD518, alemtuzumab, alirocumab, altumomab pentetate, amatuximab, anatumomab mafenatox, anifrolumab, anrukinzumab, apolizumab, arcitumomab, aselizumab, atinumab, atlizumab, atorolumumab, bapineuzumab, basiliximab, bavituximab, bectumomab, belimumab, benralizumab, bertilimumab, besilesomab, bevacizumab, beziotoxumab, biciromab, bimagrumab, bivatuzumab mertansine, blinatumomab, blosozumab, brentuximab vedotin, briakinumab, brodalumab, canakinumab, cantuzumab mertansine, cantuzumab ravtansine, caplacizumab, capromab pendetide, carlumab, catumaxomab, cBR96-doxorubicin immunoconjugate, CC49, cedelizumab, certolizumab pegol, cetuximab, Ch.14.18, citatuzumab bogatox, cixutumumab, clazakizumab, clenoliximab, clivatuzumab tetraxetan, cnatumumab, concizumab, CR6261, crenezumab, dacetuzumab, daclizumab, dalotuzumab, daratumumab, demcizumab, denosumab, detumomab, dinutuximab, diridavumab, dorlimomab aritox, drozitumab, duligotumab, dupilumab, durvalumab, dusigitumab, ecromeximab, eculizumab, edobacomab, edrecolomab, efalizumab, efungumab, eldelumab, elotuzumab, elsilimomab, emibetuzumab, enavatuzumab, enfortumab vedotin, enlimomab pegol, enokizumab, enoticumab, ensituximab, epitumomab cituxetan, epratuzumab, erlizumab, ertumaxomab, etaracizumab, etrolizumab, evinacumab, evolocumab, exbivirumab, fanolesomab, faralimomab, farletuzumab, fasinumab, FBTA05, felvizumab, fezakinumab, ficlatuzumab, figitumumab, flanvotumab, fletikumab, fontolizumab, foralumab, forvirumab, fresolimumab, fluranumab, futuximab, galiximab, ganitumab, gantenerumab, gavilimomab, gemtuzumab ozogamicin, gevokizumab, girentuximab, glembatumumab vedotin, golimumab, gomiliximab, guselkumab, ibalizumab, ibritumomab tiuxetan, icrucumab, igovomab, IMAB362, imciromab, imgatuzumab, inclacumab, indatuximab ravtansine, infliximab, inolimomab, inotuzumab ozogamicin, intetumumab, ipilimumab, iratumumab, itolizumab, ixekizumab, keliximab, labetuzumab, lambrolizumab, lampalizumab, lebrikizumab, lemalesomab, lerdelimumab, lexatumumab, libivirumab, lifastuzumab vedotin, ligelizumab, lintuzumab, lirilumab, lodelcizumab, lorvotuzumab, lorvotuzumab mertansine, lucatumumab, lulizumab pegol, lumiliximab, mapatumumab, margetuximab, maslimomab, matuzumab, mavrilimumab, mepolizumab, metelimumab, milatuzumab, minretumomam, mitumomab, mogamulizumab, morolimumab, motavizumab, moxetumomab pasudotox, muromonab-CD3, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, obiltoxaximab, ocaratuzumab, ocrelizumab, odulimomab, ofatumumab, olaratumab, olokizumab, omalizumab, onartuzumab, ontuxizumab, oportuzumab monatox, oregovomab, orticumab, otelixizumab, otlertuzumab, oxelumab, ozanezumab, ozoralizumab, pagibaximab, palivizumab, panitumumab, pankomab, panobacumab, parsatuzumab, pascolizumab, pateclizumab, patritumab, pembrolizumab, pemtumomab, perakizumab, pertuzumab, pexelizumab, pidilizumab, pinatuzumab vedotin, pintumomab, placulumab, polatuzumab vedotin, ponezumab, priliximab, pritoxaximab, pritumumab, PRO 140, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, ruplizumab, samilizumab, sarilumab, satumomab pendetide, secukinumab, seribantumab, setoxaximab, sevirumab, SGN-CD19A, SGN-CD33A, sibrotuzumab, sifalimumab, siltuximab, simtuzumab, siplizumab, sirukumab, sofitzumab vedotin, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tarextumab, tefibazumab, telimomab aritox, tenatumomab, teneliximab, teplizumab, teprotumumab, TGN1412, ticilimumab, tigatuzumab, tildrakizumab, TNX-650, tocilizumab, toralizumab, tositumomab, tovetumab, tralokinumab, trastuzumab, TRBS07, tregalizumab, tremelimumab, tucotuzumab celmoleukin, tuvirumab, ublituximab, urelumab, urtoxazumab, ustekinumab, vantictumab, vapaliximab, varlilumab, vatelizumab, vedolizumab, veltuzumab, vepalimomab, vesencumab, volociximab, vorsetuzumab mafodotin, votumumab, zalutumumab, zanolimumab, zatuximab, ziralimumab, or zolimimab aritox.

One particular receptor whose integrity can be restored by the glycocalyx-restoring and -maintaining compound is the LDL receptor, which mediates LDL endocytosis in the liver, the major route of LDL clearance from circulation. It is desired to reduce LDL levels in individuals with high cholesterol and atherosclerosis and other cardiovascular diseases. Proprotein convertase subtilisin/kexin type 9 (PCSK9) plays a critical role in cholesterol metabolism by controlling the levels of LDL particles that circulate in the bloodstream. PCSK9 increases plasma LDL cholesterol by promoting degradation of the LDL receptor. Monoclonal antibody (MAb) anti-PCSK9 (U.S. Pat. No. 8,062,640 to Sleeman, et al., U.S. Pat. Nos. 8,030,457, 8,168,762, U.S. Patent Application Publication Nos. 2011/0027287, 2012/0020975, 2012/0027765, 2012/0213797, and 2012/0251544 to Jackson, et al., WO2011/027257 to Champion, et al. describe various MAb anti-PCSK9's) is used to bind with PCSK9, or a portion(s) thereof, in order to block its mechanism of action. However, the effectiveness of MAb anti-PCSK9 is diminished when there has been disruption of the glycocalyx and in turn disruption of the receptors therein, including the LDL receptor. By administering the glycocalyx-restoring and -maintaining compound and restoring the glycocalyx, the LDL receptor can be restored as well, increasing receptor binding, and thereby increasing the efficacy of MAb anti-PCSK9 in a patient suffering from cardiovascular disease and lowering LDL levels.

Therefore, the present disclosure provides for a method of restoring the glycocalyx and receptors therein and potentiating drug response, by administering the a composition comprising the glycocalyx restoring and maintaining compound and MAb anti-PCSK9 to an individual suffering from cardiovascular disease, restoring the glycocalyx, restoring LDL receptors in the glycocalyx, and potentiating the response of the MAb anti-PCSK9. The MAb anti-PCSK9 can be any of those described above, as well as bococizumab (Pfizer RN316, described in U.S. Pat. No. 8,080,243 to Liang, et al.). The present disclosure also provides for a composition for treating cardiovascular diseases including the glycocalyx-restoring and -maintaining compound and a MAb anti-PCSK9. The components of this combination can be in the same dosage form or in different dosage forms and can be administered with different or the same release profiles.

Assessment of Efficacy of Treatment

Any means of assessing the efficacy of treatment with a glycocalyx-restoring and -maintaining composition (or other therapeutic intervention) can be used in connection with the methods and compounds described herein. Conventional methods of monitoring glycocalyx disruption include: (1) direct microscopy, which entails optical measurement of the distance between the endothelium and erythrocytes; (2) an indirect method wherein two different sizes of dextran sulfate are infused into the bloodstream (dextran-40 and dextran-70) and the relative distribution of these dextrans are measured (in theory, the difference reflects the volume of the glycocalyx); and (3) imaging via a digital camera places under the tongue to measure red blood cells as they travel through a perfused boundary region (PBR; uninterrupted blood flow indicates a healthy glycocalyx).

Example 2 illustrates one method of assessing the efficacy of treatments to restore the glycocalyx and/or reduce endothelial inflammation and/or oxidative damage to the endothelium that uses a proprietary animal model of atherosclerosis (also described more generally above). Such an assessment can be carried out in the context of drug development using non-human animals.

These methods are either cumbersome or cannot be performed on human patients. However, the biomarkers described herein provide a convenient means of assessing treatment efficacy in a subject. To this end, a sample relevant to the particular glycocalyx at issue (e.g., a blood or blood fraction, for atherosclerosis) is taken and assayed for one, two, three, four, five, six, or seven or more biomarkers (e.g., including, but not limited to, those described above). As noted above, a reduction in a formerly elevated biomarker, such as those described herein, indicate a positive therapeutic effect.

Example 1—Arterial Plaque Animal Model and Biomarkers Correlated with Plaque Formation or Vascular Inflammation A novel model of atherosclerosis in mice was developed, using a high-fat diet and administration of a polychlorinated biphenyl (3,3',4,4'-Tetrachlorobiphenyl; PCB-77) that promotes both obesity and atherosclerosis and the additional oral administration of bacteria responsible for tooth decay, *Porphyromonas gingivalis* 381 (ATCC 33277). The objective of this study was to examine the association of biomarkers in a murine model of atherosclerosis.

Materials and Methods

Mice

For a pilot study, forty-eight 10-week old male C57/Bl6 mice were obtained from Jackson Laboratories. Three mice were raised from 6 weeks on a regular diet and served as controls, and the remaining 45 were raised on a 60% fat diet (D12451, DIO series diet, Opensource Diets). For a bacterial dosage test, sixteen 10-week old male C57/Bl6 mice were divided into four treatment groups and maintained on a normal diet.

Treatments 3,3',4,4'-Tetrachlorobiphenyl (PCB-77) was obtained from Neosyn Laboratories. 100 mg of the dry chemical was suspended in 15.22 ml of corn oil to deliver 150 μmol/kg in 0.2 ml per mouse.

*Porphyromonas gingivalis* 381 (ATCC 33277) was obtained from ATCC. The bacteria were stored frozen prior to use. The bacteria were cultured in multiple sterile tubes in 40 ml of supplemented tryptic soy broth at 37° C. under anaerobic conditions. The cultures were centrifuged, the medium removed, and the samples combined. A 100-μl sample of the bacteria was mixed with 100 μl of medium and added to a 96 well plate. A microplate reader was used to measure the optical density at 600 nm to determine the concentration of bacteria. Based on the bacterial concentration, the samples were diluted to appropriate concentration with 2% carboxymethylcellulose in sterile phosphate buffered saline (PBS).

Gavage

A 20-gauge, curved feeding needle was used to administer 0.2 ml of the treatment into the stomach of each mouse. Light isoflurane gas anesthesia was utilized to facilitate introduction of the needle to the esophagus and to decrease the risk of animal injury due to movement during gavage.

The gavage schedule was carried out as listed in FIG. 1A. Sufficient bacteria were unable to be grown to produce the suggested dosage of $3\times10^{11}$ bacteria per mouse, which is much higher than the dosages used in the scientific literature, so the dosage was decreased to $5\times10^{9}$. There were 3 deaths overnight following the first bacterial gavage, so the second bacterial gavage was delayed to day 6 and the dosage reduced to $1.5\times10^{9}$.

For a dosing test, the mice received a gavage of bacteria on day 1 and day 6, to simulate the gavage schedule employed in the pilot study. FIG. 1B lists the bacterial dosages.

Sacrifice and Harvest

The mice were sacrificed on days 10, 15, or 20 according to the experimental plan (three each from groups 1-5). The animals were anesthetized by intraperitoneal injection of 90 mg/kg ketamine and 8 mg/kg xylazine, and isoflurane gas anesthesia. Blood was collected by retro-orbital bleeding or from the heart and mixed with 50 mg/ml heparan to prevent clotting. The thorax was opened to expose the heart, and saline was injected into the left ventricle, with the right atrium opened to allow the drainage of blood and saline. The heart was perfused with at least 5 ml of saline and until no blood was observed in the drainage from the atrium. The heart was carefully dissected and frozen for histological sectioning. Plasma was collected from the blood samples by centrifuging at 1000 rpm for 15 minutes and collecting the supernatant. The samples were stored at −80° C. until analysis.

Histology

The hearts were prepared as frozen sections: they were mounted in blocks, and 10 μm-thick sections were cut through the aortic valve, to yield 30 sections per mouse. Oil Red O staining was used to visualize the lipid content of the plaques. Multiple 10-μm sections at the level of the aortic sinus were analyzed for the presence of Oil Red O lipid staining, plaque size, amount of fibrous tissue, and inflammation. The percentage of the lumen occupied by the first three features was calculated using Image Pro Plus. The average percentage of each feature was used to score the three features with the following scale: For fibrous tissue, lipid staining, and plaque size: 0=<2%, 1=≥2%, 2=≥4%, 3=≥6%, 4=≥10%. The level of inflammation in each section was scored on the following scale: 0=no inflammatory cells observed, 1=few macrophages with no giant cells, 2=foam cells present, 3=foam cells with cholesterol, 4=foam cells, giant cells, and cholesterol present. The inflammation score was averaged over all the sections, then converted to an overall score: For inflammation: 0=<0.2, 1=≥0.2, 2=≥0.4, 3=≥0.6, 4=≥1.

Elisa

Six test kits were used to analyze the collected plasma samples: Thrombin-Anti-Thrombin Complex ELISA (Kamiya Biomedical Company, Thousand Oaks, California), Anti-Thrombin III ELISA (ABCam), Total Plasminogen Activation Inhibitor-1 ELISA (Molecular-Innovive), Syndecan-1 ELISA (USCN, Houston, Texas), Heparan Sulfate ELISA, and Hyaluronan Synthase 1 ELISA (antibodies-online). All tests were performed on plasma, diluted to fall within the standard curve if necessary and carried out according to the manufacturer's instructions.

Results

Pathology

Figure 2B:
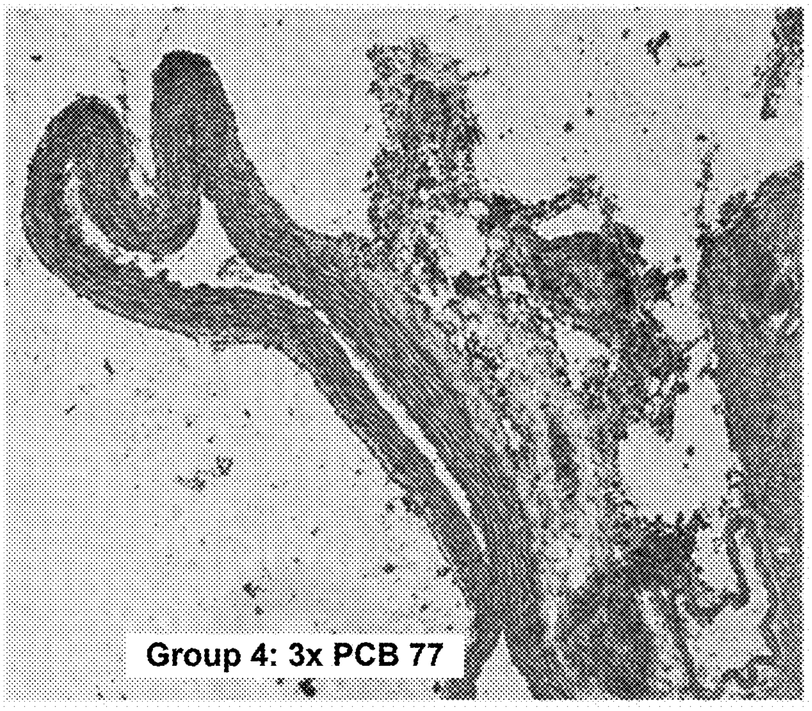

No inflammation or plaques were found in Groups 1, 2, 5 and 6; however, inflammatory cells, as indicated by general lipid staining, were observed throughout Group 3 (FIG. 2A), and well-defined atherosclerotic plaque was observed in Group 4 (FIG. 2B).

Correlation of Biomarkers with Plaque Formation or Vascular Inflammation:

Blood was drawn from the animals at various intervals and analyzed for biomarkers. Of the different markers evaluated, three showed significant levels in groups 3 and 4 animals (particularly in day 15 and 20), indicating high correlations to inflammation or plaque formation (statistically analyzed by independent T-test). These biomarkers included plasminogen (PAI-1), heparan sulfate, and hyaluronan synthase; syndecan-1 is a marginally predictive biomarker.

A. Highly Correlative Biomarkers

Figure 3:
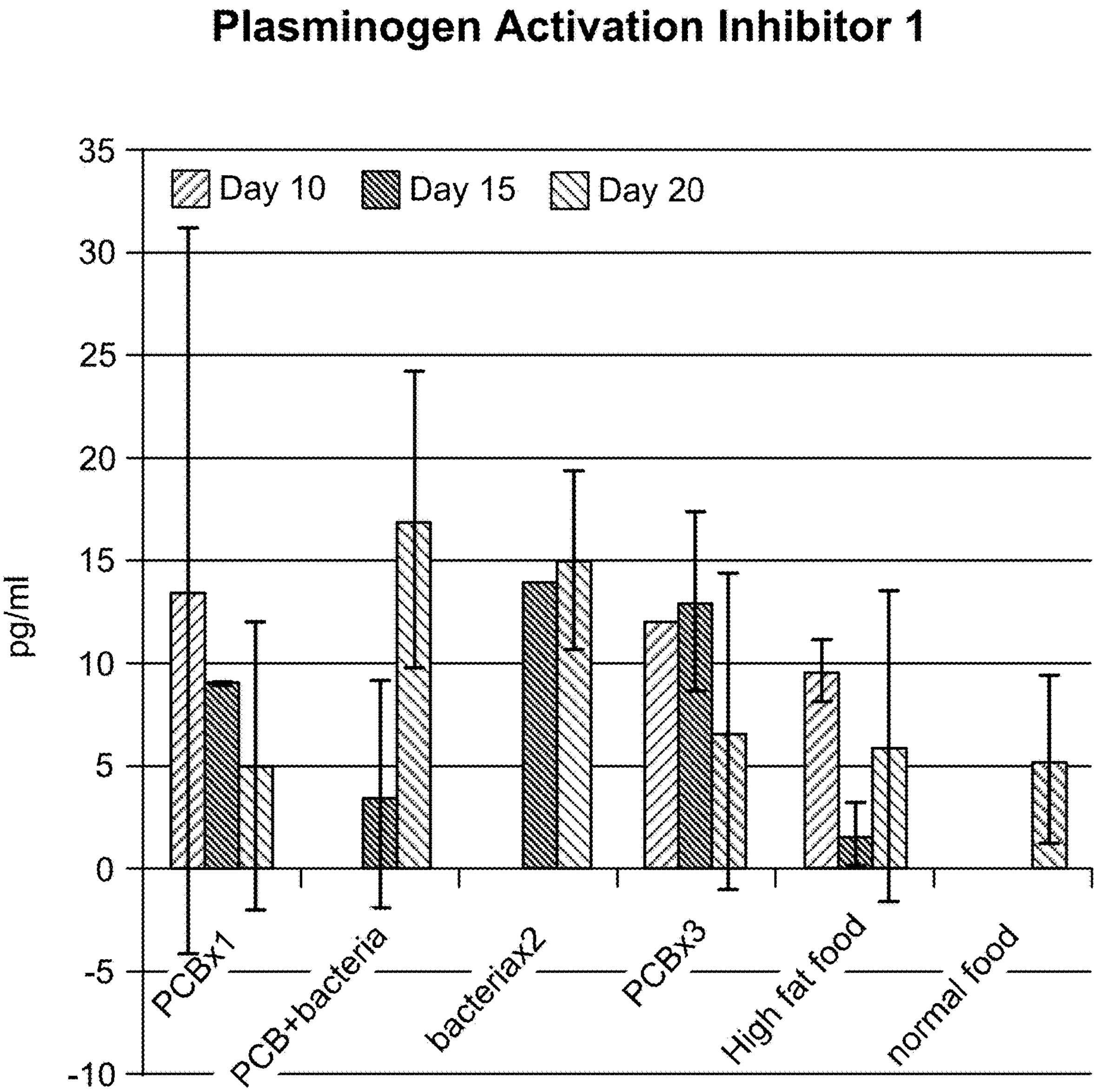
FIG. 3 is a graph of total plasminogen activation inhibitor-1 levels from Example 1.

1. Plasminogen Activator Inhibitor-1 (PAI-1):

FIG. 3 shows that PAI-1 was significantly elevated in the 20-day sacrifice, as compared to the control (group 6: normal food).

2. Heparan Sulfate (HS)

Figure 4:
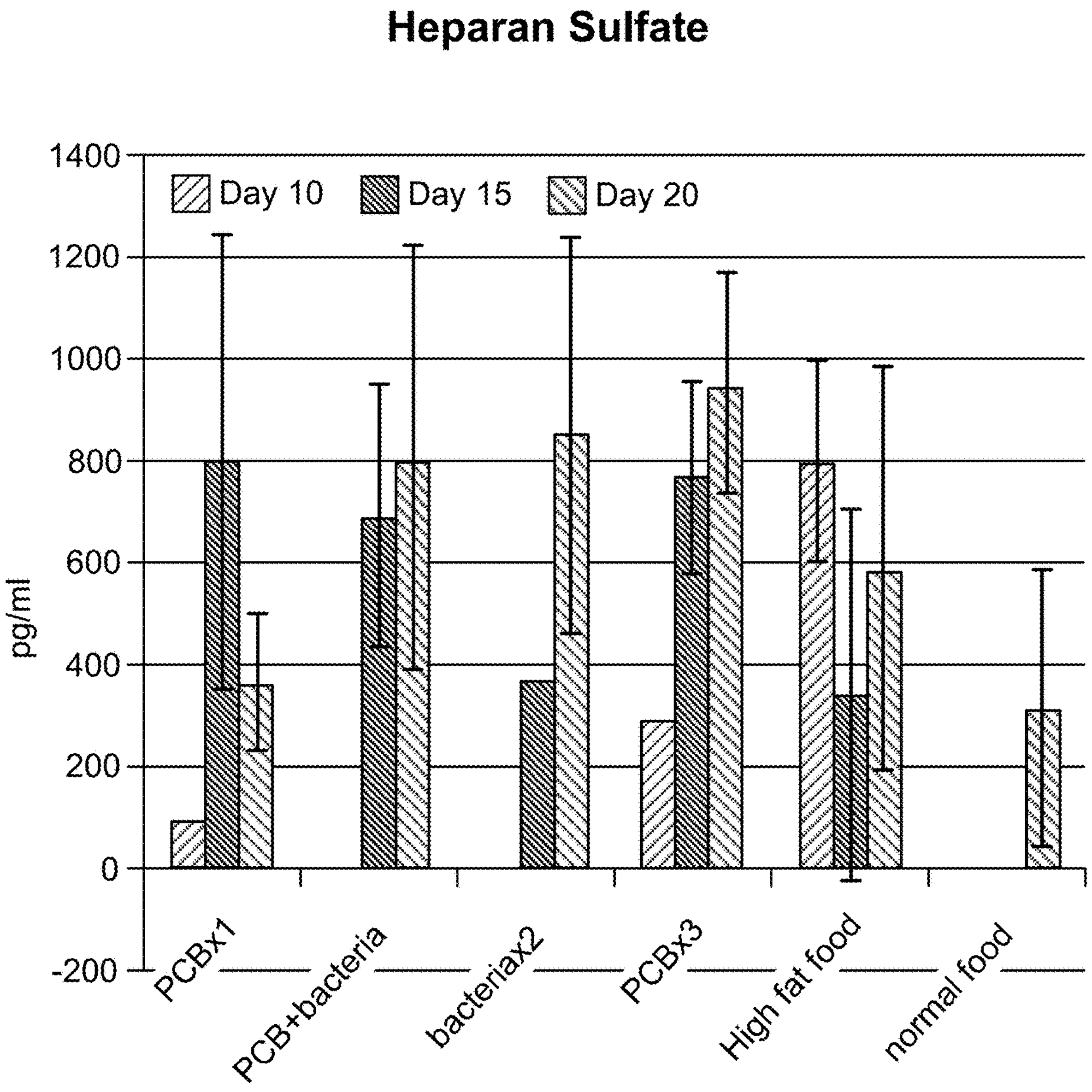
FIG. 4 is a graph of heparan sulfate levels from Example 1.

FIG. 4 shows that HS levels at 20-day sacrifice were significantly higher than in the control group.

3. Hyaluronan Synthase 1 (HAS-1)

Figure 5:
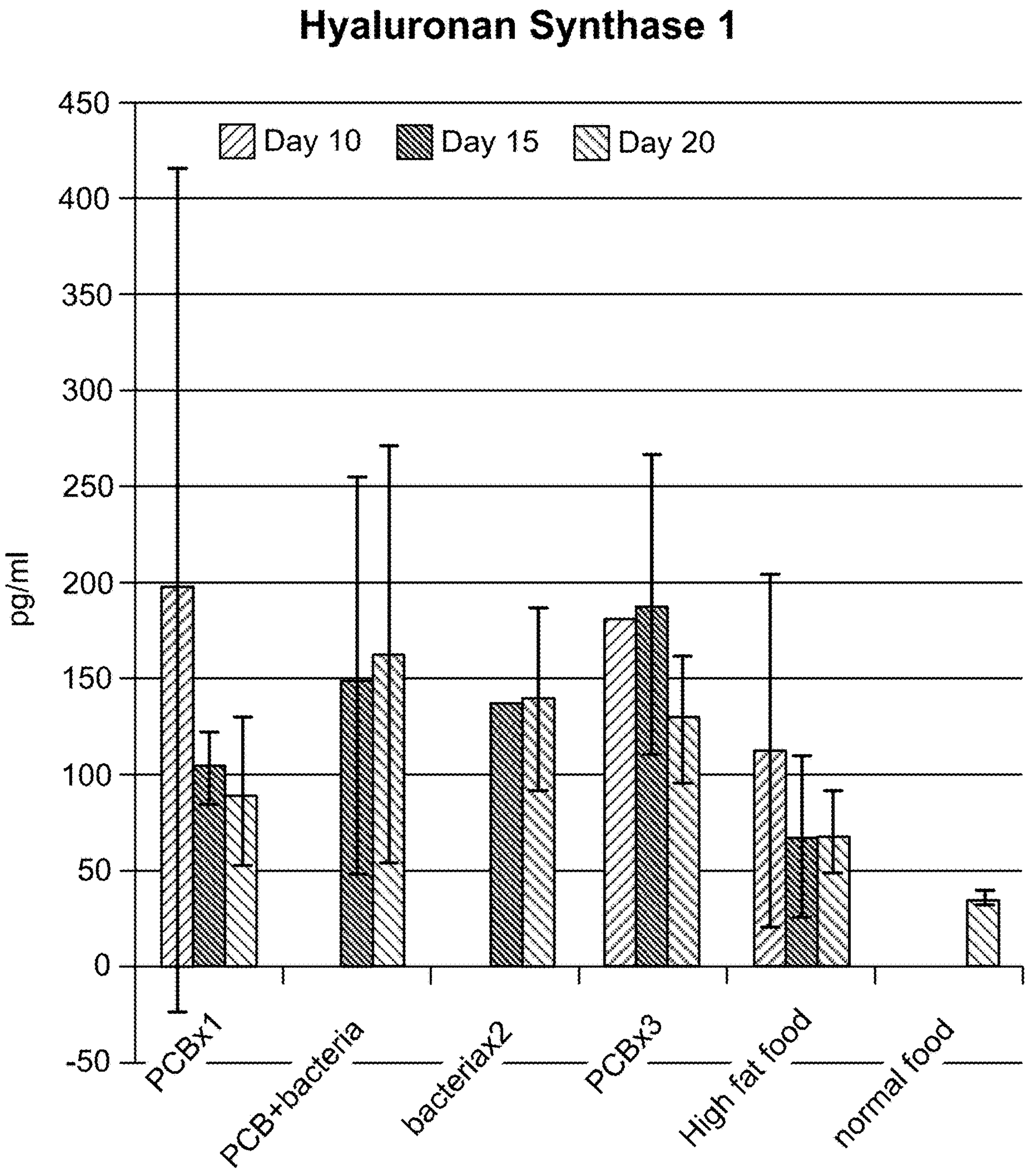
FIG. 5 is a graph of hyaluronan synthase 1 levels from Example 1.

FIG. 5 shows that hyaluronan synthase at 20 day sacrifice was significantly higher than the same time point in the control group.

B. Marginal Biomarker: 1 Syndecan-1

Figure 6:
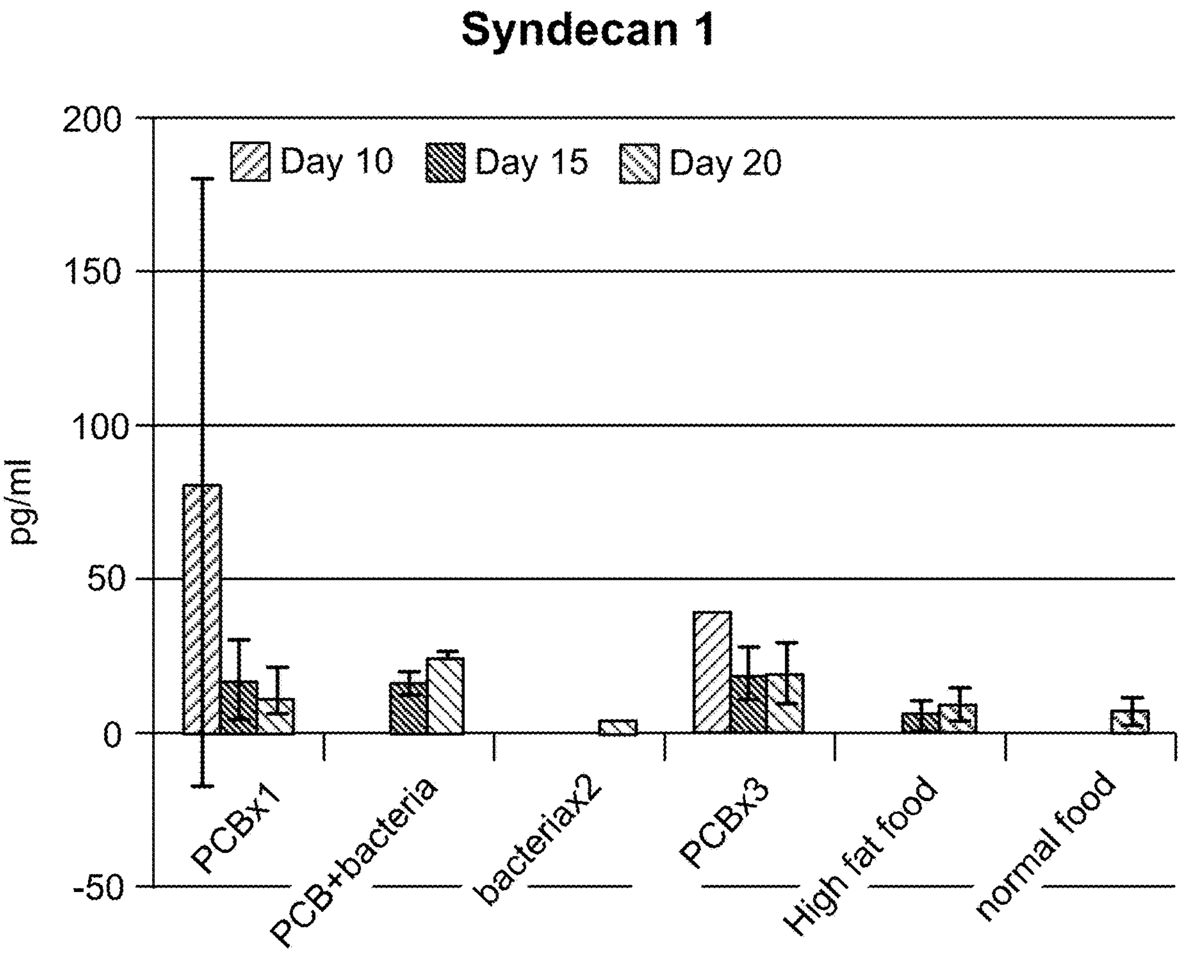
FIG. 6 is a graph of syndecan-1 levels from Example 1.

FIG. 6 shows that syndecan-1 at 10 days was significantly higher than the same time point in the control group.

C. Poorly Prognostic of Inflammation or Plaque Formation

1. Thrombin-Anti-Thrombin (TAT)

Figure 7:
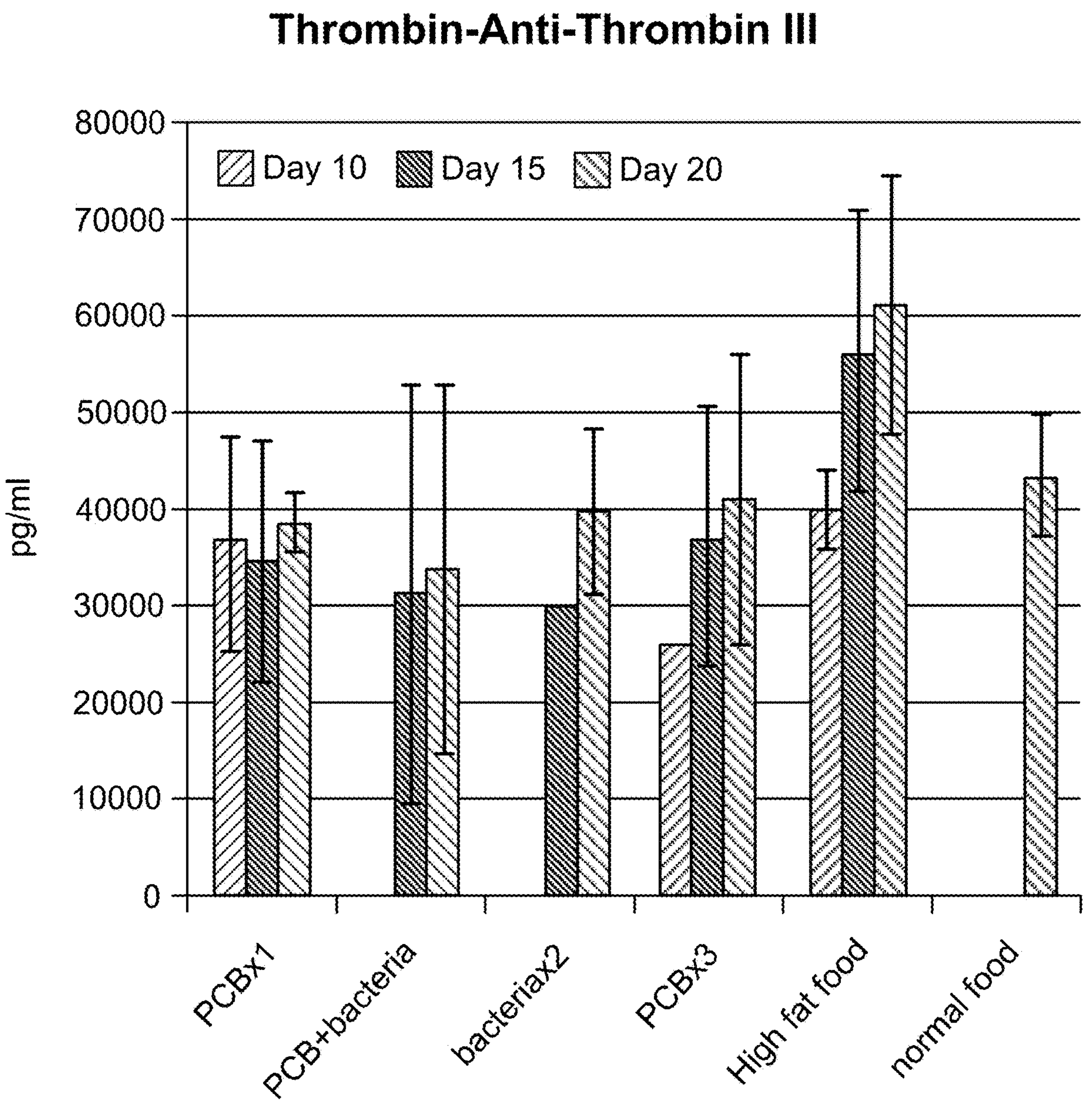
FIG. 7 is a graph of thrombin-anti-thrombin III levels from Example 1.

As shown in FIG. 7, no significant correlation was observed with TAT complexes.

2. Antithrombin III

Figure 8:
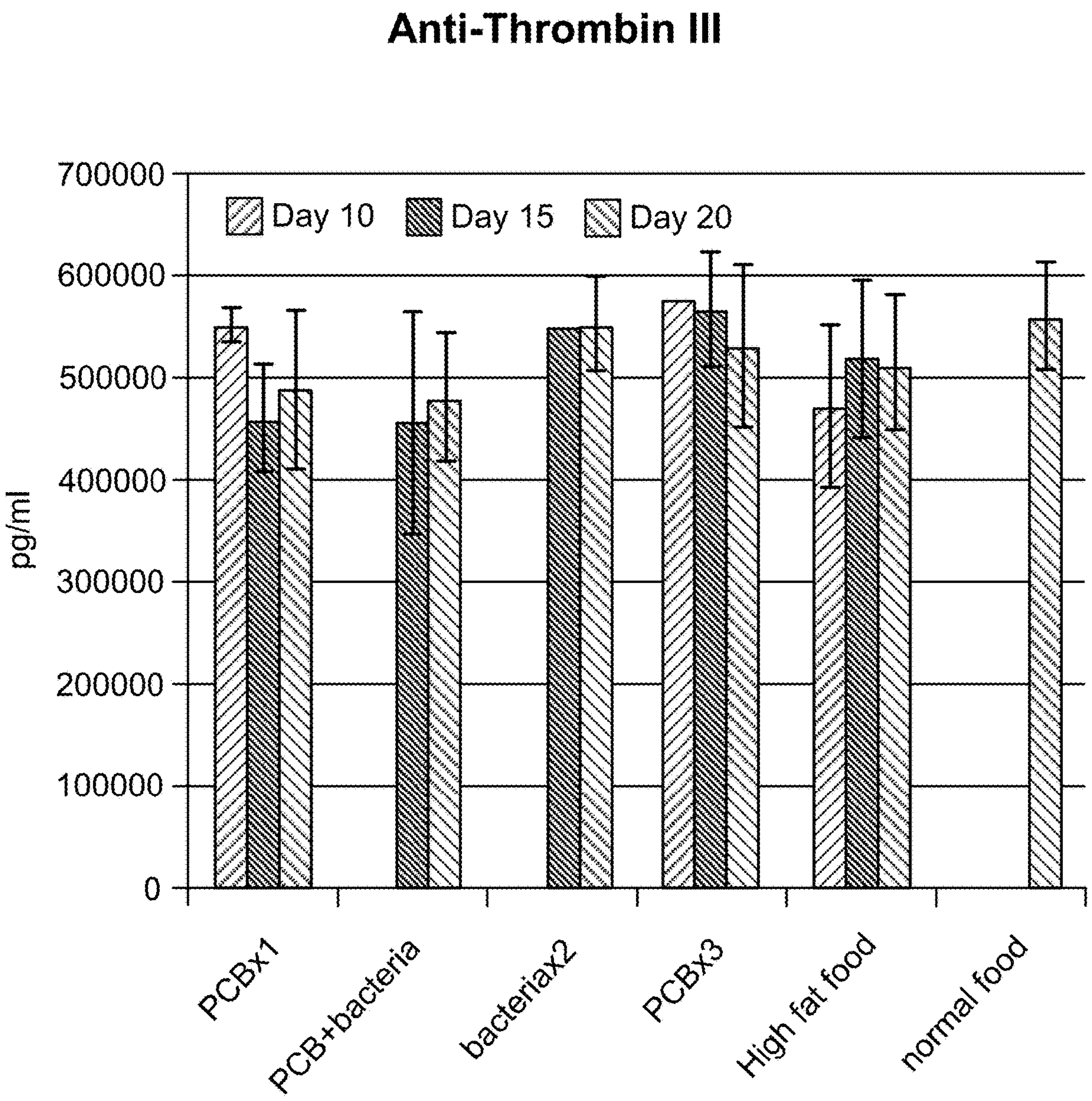
FIG. 8 is a graph of anti-thrombin levels from Example 1.

As shown in FIG. 8, there was no significant difference in the levels of anti-thrombin III between the treatment groups at any time point, or between time points within the groups, as measured by independent T-test.

Further Conclusion

Figure 9:
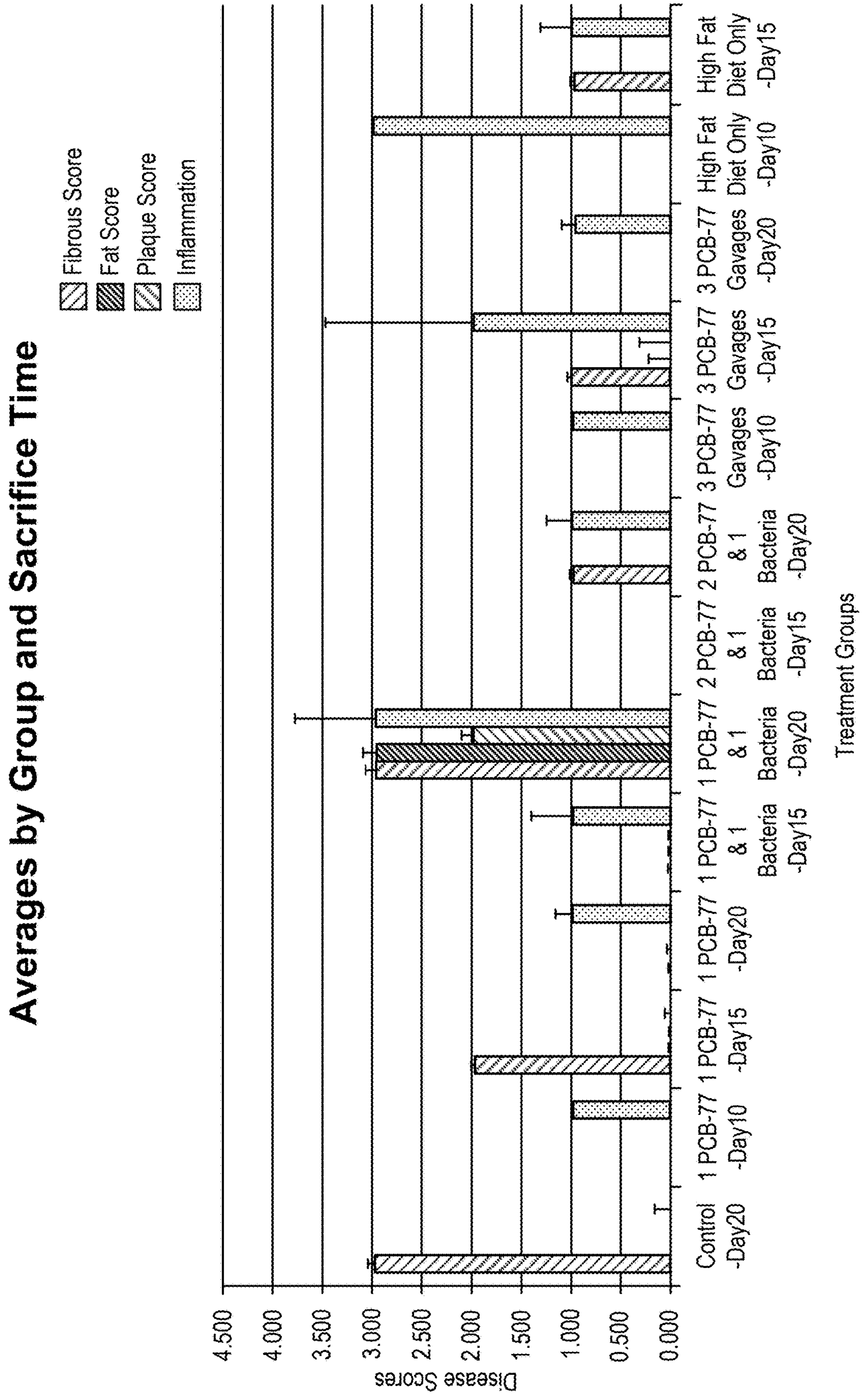
FIG. 9 is a graph of average disease scores for treatment groups and sacrifice times from Example 1.

FIG. 9 shows graphically the average scores for each group and time point, indicating PCB77 treatment as the most significant risk factor to producing inflammation and plaque.

Example 2—Efficacy of Glycocalyx-Restoring and -Maintaining Compositions Demonstrated in Arterial Plaque Animal Model The objective of this study was to examine the association of biomarkers with the murine model of atherosclerosis described in Example 1 in mice treated with a strategy to protect and repair endothelial glycocalyx.

Materials and Methods

Mice, Treatments, and Gavage

Eighty-four (84) 10-week old male C57/Bl6 mice were obtained from Jackson Laboratories. Thirty-two mice were raised from 6 weeks on a regular diet and served as controls, and the remaining mice were raised on a 60% fat diet (D12451, DIO series diet, Opensource Diets). 3,3',4,4'-Tetrachlorobiphenyl (PCB-77) was obtained from Neosyn Laboratories. The dry chemical was suspended in 15.22 ml of corn oil to deliver 200 μmol/kg in 0.2 ml by gavage per mouse. Otherwise, treatments and gavage were as described in Example 1.

Sacrifice and Harvest

The mice were sacrificed on days 4, 11, or 18 according to the experimental plan (three each from groups). The animals were anesthetized by intraperitoneal injection of 90 mg/kg ketamine and 8 mg/kg xylazine, and isoflurane gas anesthesia. Blood was collected by retro-orbital bleeding or from the heart and mixed with 50 mg/ml heparan to prevent clotting. The thorax was opened to expose the heart, and saline was injected into the left ventricle, with the right atrium opened to allow the drainage of blood and saline. The heart was perfused with at least 5 ml of saline and until no blood was observed in the drainage from the atrium. The heart was carefully dissected and frozen for histological sectioning. Plasma was collected from the blood samples by centrifuging at 1000 rpm for 15 minutes, and collecting the supernatant. The samples were stored at −80° C. until analysis.

ELISA

Four test kits were used to analyze the collected plasma samples: Heparan Sulfate ELISA and Hyaluronan Synthase 1 (HAS-1) ELISA (Antibodies-Online), Total Plasminogen Activation Inhibitor-1 (PAI-1) ELISA (Molecular-Innovive), and Syndecan-1 (SDC1) ELISA (USCN, Houston, Texas). All tests were performed on plasma, diluted to the fall within the standard curve if necessary, and carried out according to the manufacturer's instructions.

Results

Hyaluronan Synthase 1 (HAS-1)

FIG. 5 shows the results for hyaluronan synthase 1 (HAS-1). It was observed that the highest HAS-1 levels occurred in the mice on the high-fat diet treated with PCB on Day 1 and 3 and sacrificed at Day 4. Reductions in HAS-1 levels were observed in mice treated to with compounds designed to restore and repair the endothelial glycocalyx.

Heparan Sulfate (HS)

FIG. 4 shows the results for heparan sulfate. An elevation in HS was observed in mice treated PCB-77 and *Porphyromonas gingivalis.*

Total Plasminogen Activation Inhibitor-1 (PAI-1)

FIG. 3 shows the results for PAI-1. It was observed that high PAI-1 levels occurred in all mice treated with an insult designed to provoke an atherosclerosis response.

Syndecan-1 (SDC1)

FIG. 6 shows the results for SDC1. An elevation in SDC-1 was observed in mice treated PCB-77 and *Porphyromonas gingivalis*, although a high degree of variability was seen in the results for this assay.

Histology

The positive control group (high-fat diet, PCB, treatment with *Porphyromonas gingivalis*) revealed presence of a pathology consistent with plaque (FIG. 10, 10× and 40×); fibrous material loosely attached to the surface of the arterial wall was observed in this sample. In contrast, the negative control group (Normal diet, no PCB, no treatment with *Porphyromonas gingivalis*) exhibited the typical features of a normal arterial wall (10).

CONCLUSION

The three biomarkers that were found highly correlative to plaque production are hyaluronan synthase (HAS-1), heparan sulfate (HS), and plasminogen activation inhibitor-1 (PAI-1). The biochemical changes that define cardiovascular disease (CVD) have been difficult to quantitate. In this regard, simplified and predictive biomarkers have now been developed enabling the use of simple blood tests to monitor the onset of cardiovascular disease and its progression. These biomarkers have been developed to provide a reliable predictor of cardiovascular events.

The results show significantly smaller endothelial glycocalyx dimensions and amounts for two of its major constituents, heparan sulfate and hyaluronan, at the atherogenic sinus region of the carotid artery bifurcation, compared with the common carotid region; perturbed endothelial glycocalyx content at pre-lesion areas within the arterial vascular tree contributes to local loss of endothelial cell (EC) barrier properties. A possible role of the endothelial glycocalyx in control of vascular wall permeability emerged, as suggested from increased local intima-to-media ratio at sites of reduced endothelial glycocalyx dimension at atherogenic risk areas. These early changes in local intima-to-media ratio were without evidence of blood cell or monocyte accumulation within the extended intimal layer, indicating a minimal inflammatory response at this very early stage.

In conclusion, predisposed arterial vascular regions have lower amounts of carbohydrate structures such as heparan sulfate and hyaluronan present within their luminal surface endothelial glycocalyx that results in locally reduced permeability barrier properties. In the present study, we reveal the endothelial cell glycocalyx as a complex 3-D matrix, vulnerable to atherogenic risk factors, which, through preexisting differences in local architecture, results in locally predisposed vulnerable arterial sites.

As shown in FIGS. 12A-12H and 14, a reasonable number of compounds tested exhibited an influence upon the biomarkers in the murine model of atherosclerosis, with marker changes in hyaluronan synthase 1 (HAS-1) and total plasminogen activation inhibitor-1 (PAI-1) in the curative model and heparan sulfate (HS) and total plasminogen activation inhibitor-1 (PAI-1) in the preventative protocol.

What is claimed is:

1. A method of treating a subject having a disease characterized by a disruption of a glycocalyx, the method comprising:

administering to the subject a composition of Formula I, Formula II, Formula III, Formula IV, Formula V, Formula VI, Formula VII, Formula VIII, Formula IX, Formula X, or Formula XI:

(FORMULA I)

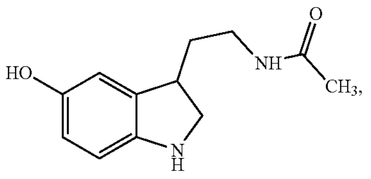

(FORMULA II)

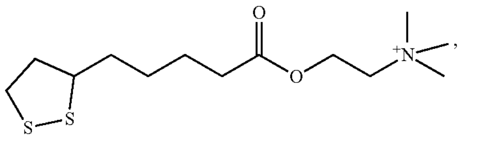

(FORMULA III)

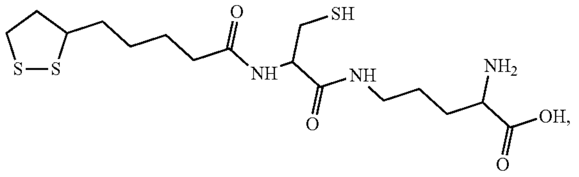

(FORMULA IV)

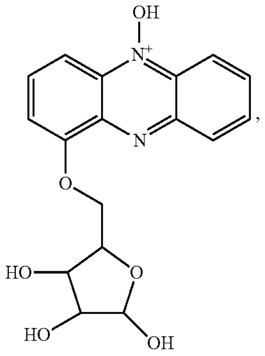

(FORMULA V)

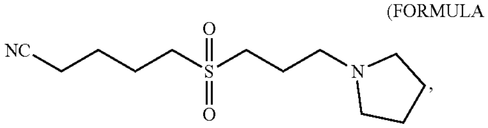

(FORMULA VI)

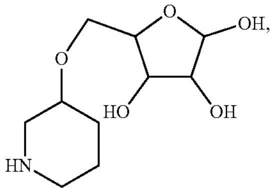

(FORMULA VII)

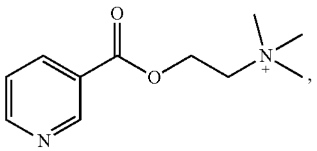

(FORMULA VIII)

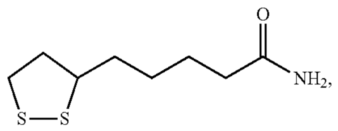

-continued (FORMULA IX)

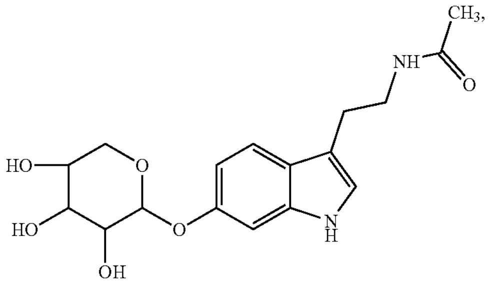

(FORMULA X)

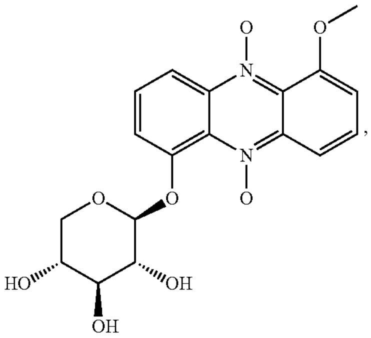

, or (FORMULA XI)

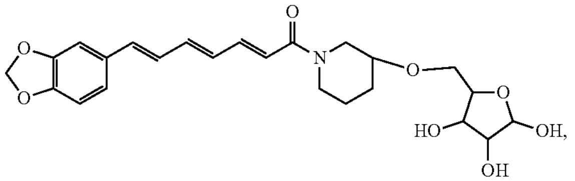

wherein the subject has been previously identified as having the disease characterized by the disruption of the glycocalyx by measuring at least three biomarkers selected from the group consisting of gamma fibrinogen (GF), growth differentiation factor 15 (GDF-15), and pregnancy-associated plasma protein (PAPP-A).

2. A method comprising:

obtaining a biological sample from a subject;

measuring a level of each biomarker of at least three biomarkers in the biological sample, wherein each biomarker of the at least three biomarkers is selected from the group consisting of gamma fibrinogen (GF), growth differentiation factor 15 (GDF-15), and pregnancy-associated plasma protein (PAPP-A); and administering to the subject a composition of Formula I, Formula II, Formula II, Formula IV, Formula V, Formula VI, Formula VII, Formula VIII, Formula IX, Formula X, or Formula XI:

(FORMULA I)

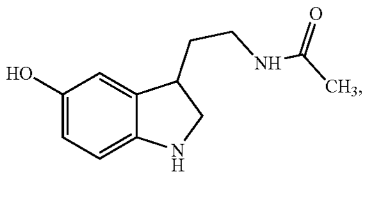

-continued (FORMULA II)

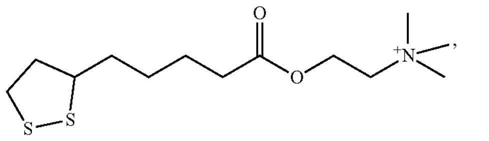

(FORMULA III)

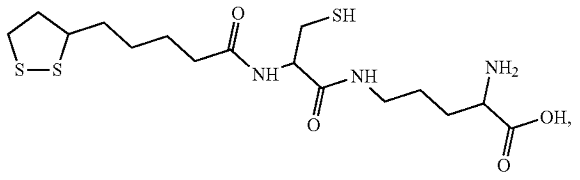

(FORMULA IV)

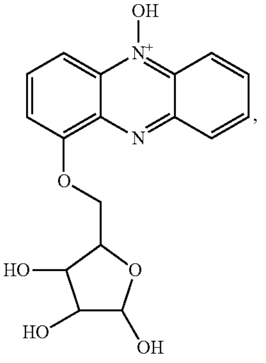

(FORMULA V)

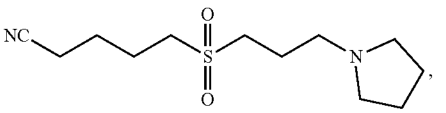

(FORMULA VI)

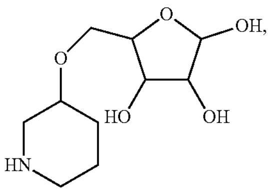

(FORMULA VII)

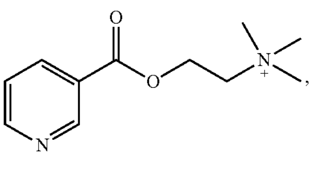

(FORMULA VIII)

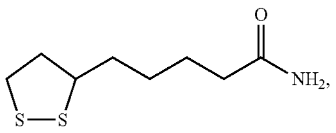

-continued (FORMULA IX)

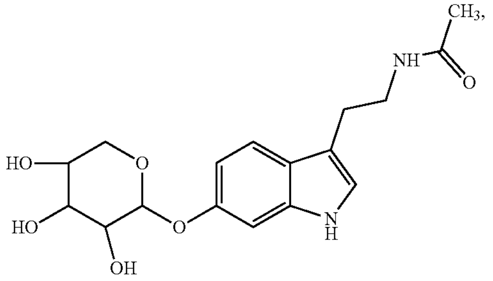

(FORMULA X)

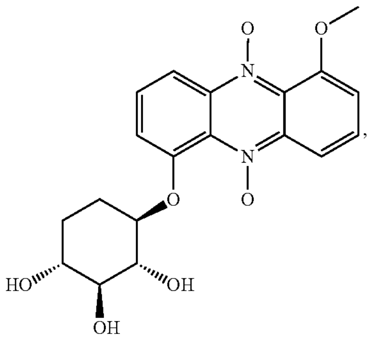

or (FORMULA XI)

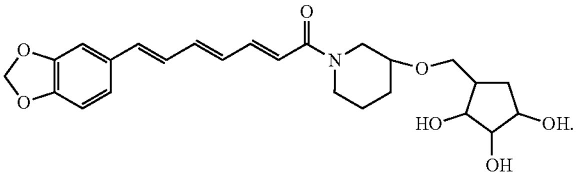

3. A method of treating a subject identified as having coronary heart disease (CHD), hypertension (HTN), or heart failure (HF), the method comprising:

obtaining a blood sample from a subject;

measuring a level of each biomarker of at least three biomarkers in the blood sample, wherein each biomarker of the at least three biomarkers is selected from the group consisting of gamma fibrinogen (GF), growth differentiation factor 15 (GDF-15), and pregnancy-associated plasma protein (PAPP-A);

determining the subject as having the CHD, the HTN, or the HF by detecting a biological signature indicative of the CHD, the HTN, or the HF from the level of each biomarker of the at least three biomarkers; and treating the subject for the CHD, the HTN, or the HF by administering to the subject a composition of Formula I, Formula II, Formula III, Formula IV, Formula V, Formula VI, Formula VII, Formula VIII, Formula IX, Formula X, or Formula XI:

(FORMULA I)

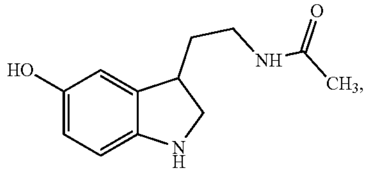

-continued (FORMULA II)

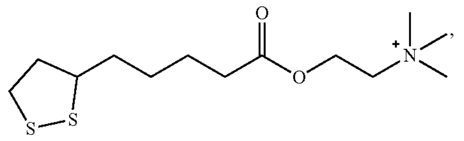

(FORMULA III)

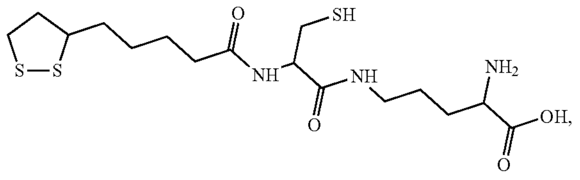

(FORMULA IV)

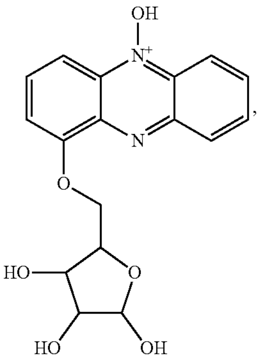

(FORMULA V)

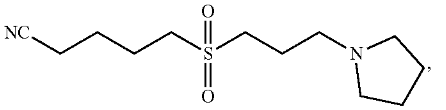

(FORMULA VI)

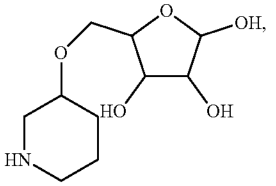

(FORMULA VII)

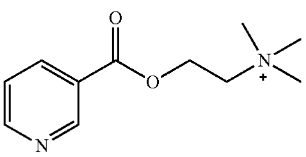

(FORMULA VIII)

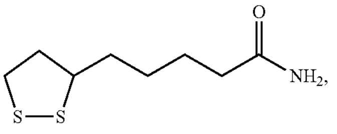

-continued (FORMULA IX)

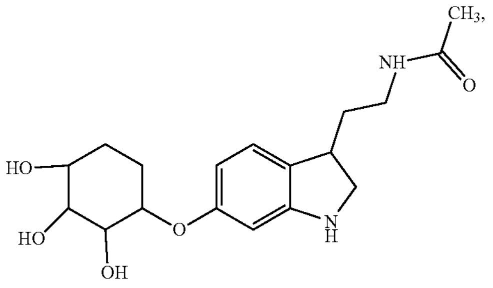

(FORMULA X)

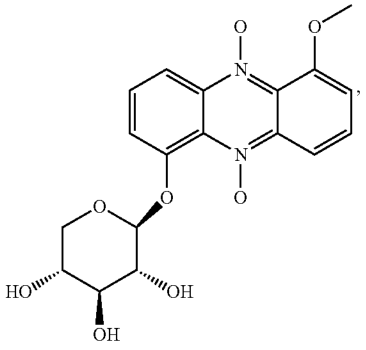

or (FORMULA XI)

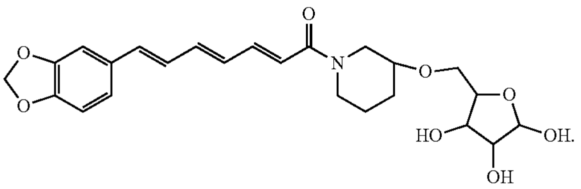

4. The method of claim 1, wherein the at least three biomarkers further comprise at least one of hyaluronan synthase-1 (HAS-1), heparan sulfate (HS), plasminogen activator inhibitor (PAI-1), and syndecan-1 (SDC-1).

5. The method of claim 2, wherein the at least three biomarkers further comprise at least one of hyaluronan synthase-1 (HAS-1), heparan sulfate (HS), plasminogen activator inhibitor (PAI-1), and syndecan-1 (SDC-1).

6. The method of claim 3, wherein the at least three biomarkers further comprise at least one of hyaluronan synthase-1 (HAS-1), heparan sulfate (HS), plasminogen activator inhibitor (PAI-1), and syndecan-1 (SDC-1).

7. The method of claim 1, further comprising:

administering to the subject at least one other composition of Formula I, Formula II, Formula III, Formula IV, Formula V, Formula VI, Formula VII, Formula VIII, Formula IX, Formula X, or Formula XI, wherein the composition differs from the at least one other composition.

8. The method of claim 7, wherein:

(a) the composition comprises Formula I and the at least one other composition comprises Formula II or Formula III, (b) the composition comprises Formula I and the at least one other composition comprises Formula VI or Formula VII, (c) the composition comprises Formula I and the at least one other composition comprises Formula IV or Formula V, or (d) the composition comprises Formula II and the at least one other composition comprises Formula VI or Formula VII.

9. The method of claim 2, further comprising:

administering to the subject at least one other composition of Formula I, Formula II, Formula III, Formula IV, Formula V, Formula VI, Formula VII, Formula VIII, Formula IX, Formula X, or Formula XI, wherein the composition differs from the at least one other composition.

10. The method of claim 9, wherein:

(a) the composition comprises Formula I and the at least one other composition comprises Formula II or Formula III, (b) the composition comprises Formula I and the at least one other composition comprises Formula VI or Formula VII, (c) the composition comprises Formula I and the at least one other composition comprises Formula IV or Formula V, or (d) the composition comprises Formula II and the at least one other composition comprises Formula VI or Formula VII.

11. The method of claim 3, further comprising:

administering to the subject at least one other composition of Formula I, Formula II, Formula III, Formula IV, Formula V, Formula VI, Formula VII, Formula VIII, Formula IX, Formula X, or Formula XI, wherein the composition differs from the at least one other composition.

12. The method of claim 11, wherein:

(a) the composition comprises Formula I and the at least one other composition comprises Formula II or Formula III, (b) the composition comprises Formula I and the at least one other composition comprises Formula VI or Formula VII, (c) the composition comprises Formula I and the at least one other composition comprises Formula IV or Formula V, or (d) the composition comprises Formula II and the at least one other composition comprises Formula VI or Formula VII.

13. The method of claim 1, wherein the composition is administered to the subject as an oral formulation.

14. The method of claim 13, wherein a dosage of the oral formulation ranges from about 0.05 mg/kg to 200.0 mg/kg.

15. The method of claim 2, wherein the composition is administered to the subject as an oral formulation.

16. The method of claim 15, wherein a dosage of the oral formulation ranges from about 0.05 mg/kg to 200.0 mg/kg.

17. The method of claim 3, wherein the composition is administered to the subject as an oral formulation.

18. The method of claim 17, wherein a dosage of the oral formulation ranges from about 0.05 mg/kg to 200.0 mg/kg.

19. The method of claim 1, further comprising:

co-administering the composition with at least one other therapeutic agent.

20. The method of claim 2, further comprising:

co-administering the composition with at least one other therapeutic agent.

21. The method of claim 3, further comprising:

co-administering the composition with at least one other therapeutic agent.

* * * * *